US012617853B2

(12) United States Patent
McAuley et al.

(10) Patent No.: US 12,617,853 B2
(45) Date of Patent: *May 5, 2026

(54) LOW pH PHARMACEUTICAL COMPOSITION COMPRISING T CELL ENGAGING ANTIBODY CONSTRUCTS

(71) Applicants: AMGEN RESEARCH (MUNCIH) GMBH, Munich (DE); AMGEN INC., Thousand Oaks, CA (US)

(72) Inventors: Arnold McAuley, Moorpark, CA (US); Pavan Ghattyvenkatakrishna, Newbury Park, CA (US); Jeff Abel, Simi Valley, CA (US); Joon Huh, Culver City, CA (US); Cornelius Pompe, Munich (DE); Sekhar Kanapuram, Thousand Oaks, CA (US); Michael Treuheit, Newbury Park, CA (US); Bharadwaj Jagannathan, Thousand Oaks, CA (US)

(73) Assignees: Amgen Research (Munich), GmbH, Munich (DE); Amgen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/482,603

(22) PCT Filed: Feb. 2, 2018

(86) PCT No.: PCT/EP2018/052665
§ 371 (c)(1),
(2) Date: Jul. 31, 2019

(87) PCT Pub. No.: WO2018/141910
PCT Pub. Date: Aug. 9, 2018

(65) Prior Publication Data
US 2020/0332000 A1      Oct. 22, 2020

Related U.S. Application Data

(60) Provisional application No. 62/453,952, filed on Feb. 2, 2017.

(51) Int. Cl.
*A61K 47/26*        (2006.01)
*C07K 16/28*        (2006.01)
*A61K 39/00*        (2006.01)

(52) U.S. Cl.
CPC .......... *C07K 16/2809* (2013.01); *A61K 47/26* (2013.01); *C07K 16/2863* (2013.01); *C07K 16/2887* (2013.01); *A61K 2039/505* (2013.01); *A61K 2039/545* (2013.01); *C07K 2317/31* (2013.01); *C07K 2317/622* (2013.01)

(58) Field of Classification Search
CPC . C07K 16/2809; C07K 16/2863; A61K 47/26
USPC ...................................................... 424/136.1
See application file for complete search history.

(56) References Cited

U.S. PATENT DOCUMENTS

| | | | |
|---|---|---|---|
| 3,691,016 A | 9/1972 | Patel | |
| 3,773,919 A | 11/1973 | Boswell et al. | |
| 3,969,287 A | 7/1976 | Jaworek et al. | |
| 4,179,337 A | 12/1979 | Davis et al. | |
| 4,195,128 A | 3/1980 | Gribnau et al. | |
| 4,229,537 A | 10/1980 | Hodgins et al. | |
| 4,247,642 A | 1/1981 | Hirohara et al. | |
| 4,301,144 A | 11/1981 | Iwashita et al. | |
| 4,330,440 A | 5/1982 | Ayers et al. | |
| 4,439,196 A | 3/1984 | Higuchi | |
| 4,447,224 A | 5/1984 | Decant et al. | |
| 4,447,233 A | 5/1984 | Mayfield | |
| 4,475,196 A | 10/1984 | La Zor | |
| 4,485,045 A | 11/1984 | Regen | |
| 4,486,194 A | 12/1984 | Ferrara | |
| 4,487,603 A | 12/1984 | Harris | |
| 4,496,689 A | 1/1985 | Mitra | |
| 4,544,545 A | 10/1985 | Ryan et al. | |
| 4,596,556 A | 6/1986 | Morrow et al. | |
| 4,640,835 A | 2/1987 | Shimizu et al. | |
| 4,670,417 A | 6/1987 | Iwasaki et al. | |
| 4,694,778 A | 9/1987 | Learn et al. | |
| 4,751,180 A | 6/1988 | Cousens et al. | |
| 4,790,824 A | 12/1988 | Morrow et al. | |

(Continued)

FOREIGN PATENT DOCUMENTS

| | | |
|---|---|---|
| EP | 0088046 A2 | 9/1983 |
| EP | 0133988 A2 | 3/1985 |

(Continued)

OTHER PUBLICATIONS

US Pharmacopeia (//www.usp.org/search?search_api_fulltext= antibody; pp. 1-7; Jun. 8, 2021).*
Goyon et al. (J Chromatogr B Analyt Technol Biomed Life Sci, 1065-1066:119-128 ( Oct. 15, 2017)).*
Thompson et al (J Chem Phys Nov. 14, 2016;145(18):185101).*
Shepard et al (PLOSOne 18(6): e0273884 (Jun. 22, 2023)).*
Zhu et al (International Journal of Cancer (1995), 62(3), 319-24).*
Altshuler et al., (Biochemistry (Moscow), 75(13): 1584-1605 (2010)).*

(Continued)

*Primary Examiner* — Lynn A Bristol
(74) *Attorney, Agent, or Firm* — Sebastian Fuchs; Wyan-Ching M. Lee

(57)        ABSTRACT

The present disclosure provides a low pH pharmaceutical composition comprising (a) an antibody constructs comprising a first domain binding to a target cell surface antigen, a second domain binding to a second antigen and preferably a third domain, which is a specific Fc modality, (b) at least one buffer agent, (c) at least one saccharide, and (d) at least one surfactant; and wherein the pH of the pharmaceutical composition is in the range of 3.5 to 6.

17 Claims, 11 Drawing Sheets

Specification includes a Sequence Listing.

(56) References Cited

U.S. PATENT DOCUMENTS

| | | | |
|---|---|---|---|
| 4,791,192 A | 12/1988 | Nakagawa et al. | |
| 4,816,397 A | 3/1989 | Boss et al. | |
| 4,816,567 A | 3/1989 | Cabilly et al. | |
| 4,935,233 A | 6/1990 | Bell et al. | |
| 4,941,880 A | 7/1990 | Burns | |
| 4,946,778 A | 8/1990 | Ladner et al. | |
| 5,013,556 A | 5/1991 | Woodle et al. | |
| 5,064,413 A | 11/1991 | McKinnon et al. | |
| 5,223,409 A | 6/1993 | Ladner et al. | |
| 5,225,639 A | 7/1993 | Winter | |
| 5,260,203 A | 11/1993 | Ladner et al. | |
| 5,292,658 A | 3/1994 | Cormier et al. | |
| 5,312,335 A | 5/1994 | McKinnon et al. | |
| 5,383,851 A | 1/1995 | McKinnon et al. | |
| 5,399,163 A | 3/1995 | Peterson et al. | |
| 5,418,155 A | 5/1995 | Cormier et al. | |
| 5,476,996 A | 12/1995 | Wilson et al. | |
| 5,545,806 A | 8/1996 | Lonberg et al. | |
| 5,545,807 A | 8/1996 | Surani et al. | |
| 5,565,332 A | 10/1996 | Hoogenboom et al. | |
| 5,585,089 A | 12/1996 | Queen et al. | |
| 5,591,669 A | 1/1997 | Krimpenfort et al. | |
| 5,612,205 A | 3/1997 | Kay et al. | |
| 5,625,126 A | 4/1997 | Lonberg et al. | |
| 5,625,825 A | 4/1997 | Rostoker et al. | |
| 5,633,425 A | 5/1997 | Lonberg et al. | |
| 5,643,763 A | 7/1997 | Dunn et al. | |
| 5,648,260 A | 7/1997 | Winter et al. | |
| 5,661,016 A | 8/1997 | Lonberg et al. | |
| 5,683,888 A | 11/1997 | Campbell | |
| 5,693,761 A | 12/1997 | Queen et al. | |
| 5,693,762 A | 12/1997 | Queen et al. | |
| 5,698,767 A | 12/1997 | Wilson et al. | |
| 5,721,367 A | 2/1998 | Kay et al. | |
| 5,741,668 A | 4/1998 | Ward et al. | |
| 5,770,429 A | 6/1998 | Lonberg et al. | |
| 5,777,079 A | 7/1998 | Tsien et al. | |
| 5,789,215 A | 8/1998 | Berns et al. | |
| 5,789,650 A | 8/1998 | Lonberg et al. | |
| 5,804,387 A | 9/1998 | Cormack et al. | |
| 5,814,318 A | 9/1998 | Lonberg et al. | |
| 5,859,206 A | 1/1999 | Adair et al. | |
| 5,874,299 A | 2/1999 | Lonberg et al. | |
| 5,876,995 A | 3/1999 | Bryan | |
| 5,877,397 A | 3/1999 | Lonberg et al. | |
| 5,925,558 A | 7/1999 | Tsien et al. | |
| 5,939,598 A | 8/1999 | Kucherlapati et al. | |
| 5,958,765 A | 9/1999 | Brams et al. | |
| 5,981,175 A | 11/1999 | Loring et al. | |
| 6,023,010 A | 2/2000 | Krimpenfort et al. | |
| 6,075,181 A | 6/2000 | Kucherlapati et al. | |
| 6,114,598 A | 9/2000 | Kucherlapati et al. | |
| 6,150,584 A | 11/2000 | Kucherlapati et al. | |
| 6,162,963 A | 12/2000 | Kucherlapati et al. | |
| 6,255,458 B1 | 7/2001 | Lonberg et al. | |
| 6,267,958 B1 | 7/2001 | Andya et al. | |
| 6,300,064 B1 | 10/2001 | Knappik et al. | |
| 6,407,213 B1 | 6/2002 | Carter et al. | |
| 6,569,825 B1 | 5/2003 | Pratley et al. | |
| 6,673,986 B1 | 1/2004 | Kucherlapati et al. | |
| 6,874,304 B2 | 4/2005 | Clauss et al. | |
| 2002/0103345 A1 | 8/2002 | Zhu | |
| 2003/0070185 A1 | 4/2003 | Jakobovits et al. | |
| 2005/0076395 A1 | 4/2005 | Kucherlapati et al. | |
| 2009/0163699 A1 | 6/2009 | Chamberlain et al. | |
| 2011/0054151 A1 | 3/2011 | Lazar et al. | |
| 2014/0302037 A1 | 10/2014 | Borges et al. | |
| 2014/0308285 A1 | 10/2014 | Yan et al. | |
| 2020/0055932 A1* | 2/2020 | Dahlhoff | C07K 16/3023 |
| 2021/0047407 A1* | 2/2021 | Christian | A61K 47/10 |
| 2021/0130465 A1* | 5/2021 | Raum | A61K 9/0019 |
| 2022/0403035 A1* | 12/2022 | Anlahr | C07K 16/2863 |
| 2023/0167175 A1* | 6/2023 | Christian | C07K 16/2875 424/136.1 |
| 2023/0192884 A1* | 6/2023 | Raum | C07K 16/28 424/136.1 |
| 2024/0209078 A1* | 6/2024 | Everts | C07K 16/2863 |
| 2024/0336685 A1* | 10/2024 | Jagannathan | A61K 9/1688 |
| 2024/0384006 A1* | 11/2024 | Panzer | C07K 16/468 |

FOREIGN PATENT DOCUMENTS

| | | | |
|---|---|---|---|
| EP | 0171496 A2 | 2/1986 | |
| EP | 0173494 A2 | 3/1986 | |
| EP | 0058481 B1 | 10/1986 | |
| EP | 0143949 B1 | 10/1988 | |
| EP | 0036676 B2 | 9/1990 | |
| EP | 0239400 B1 | 8/1994 | |
| EP | 0463151 B1 | 6/1996 | |
| EP | 0773288 A2 | 5/1997 | |
| EP | 0546073 B1 | 9/1997 | |
| EP | 0843961 A1 | 5/1998 | |
| EP | 4218821 A2 * | 8/2023 | |
| GB | 2177096 A | 1/1987 | |
| JP | 3068180 B2 | 7/2000 | |
| JP | 3068506 B2 | 7/2000 | |
| JP | 3068507 B2 | 7/2000 | |
| WO | 1987/05330 A1 | 9/1987 | |
| WO | 1988/01649 A1 | 3/1988 | |
| WO | 1988/09344 A1 | 12/1988 | |
| WO | 1992/03918 A1 | 3/1992 | |
| WO | 1992/15673 A1 | 9/1992 | |
| WO | 1992/22645 A1 | 12/1992 | |
| WO | 1992/22647 A1 | 12/1992 | |
| WO | 1992/22670 A1 | 12/1992 | |
| WO | 1993/12227 A1 | 6/1993 | |
| WO | 1993/15722 A1 | 8/1993 | |
| WO | 1994/00569 A1 | 1/1994 | |
| WO | 1994/02602 A1 | 2/1994 | |
| WO | 1994/25585 A1 | 11/1994 | |
| WO | 1995/07463 A1 | 3/1995 | |
| WO | 1996/14436 A1 | 5/1996 | |
| WO | 1996/33735 A1 | 10/1996 | |
| WO | 1996/34096 A1 | 10/1996 | |
| WO | 1997/13852 A1 | 4/1997 | |
| WO | 1997/38731 A1 | 10/1997 | |
| WO | 1998/14605 A1 | 4/1998 | |
| WO | 1998/24884 A1 | 6/1998 | |
| WO | 1998/24893 A2 | 6/1998 | |
| WO | 1998/26277 A2 | 6/1998 | |
| WO | 1998/52976 A1 | 11/1998 | |
| WO | 1999/49019 A2 | 9/1999 | |
| WO | 1999/54440 A1 | 10/1999 | |
| WO | 2000/06605 A2 | 2/2000 | |
| WO | 2000/34317 A2 | 6/2000 | |
| WO | 2000/76310 A1 | 12/2000 | |
| WO | 2003/47336 A2 | 6/2003 | |
| WO | 2005/040220 A1 | 5/2005 | |
| WO | 2006/020258 A2 | 2/2006 | |
| WO | 2006/138181 A2 | 12/2006 | |
| WO | 2007/042261 A2 | 4/2007 | |
| WO | 2008/045373 A2 | 4/2008 | |
| WO | 2008/119567 A2 | 10/2008 | |
| WO | 2009/032782 A2 | 3/2009 | |
| WO | 2009/070642 A1 | 6/2009 | |
| WO | 2010/037838 A2 | 4/2010 | |
| WO | 2013/026833 A1 | 2/2013 | |
| WO | 2013/026837 A1 | 2/2013 | |
| WO | 2014/144722 A2 | 9/2014 | |
| WO | 2014/151910 A1 | 9/2014 | |
| WO | 2015/048272 A1 | 4/2015 | |
| WO | 2016/036678 A1 | 3/2016 | |
| WO | 2022096698 * | 5/2022 | |

OTHER PUBLICATIONS

Vajda et al., (Current Opinion in Structural Biology, 67 pp. 226-231 (2021)).*

Akbar et al., (Cell Reports 34, 108856, Mar. 16, 2021).*

Lo et al., (BMC Genomics vol. 22, Article No. 116 (2021)).*

U.S. Appl. No. 19/024,641, filed Jan. 16, 2025, Mcauley; Arnold.*

U.S. Appl. No. 19/022,064, filed Jan. 15, 2025, Christian; Twinkle.*

(56)        References Cited

OTHER PUBLICATIONS

U.S. Appl. No. 16/482,603, Response to Final Office Action of Aug. 7, 2024 (pp. 1-31 (Feb. 7, 2025)).*

Altschul et al., Basic local alignment search tool, J. Mol. Biol., 215:403-410 (1990).

Altschul et al., Gapped BLAST and PSI-BLAST: a new generation of protein database search programs, Nucleic Acids Res., 25:3389-3402 (1997).

Altschul et al., Local alignment statistics, Methods in Enzymology, 266:460-480 (1996).

Aplin et al., Preparation, properties, and applications of carbohydrate conjugates of proteins and lipids, CRC Grit. Rev Biochem., 10:259-306 (1981).

Arakawa et al., Solvent interactions in pharmaceutical formulations, Pharm. Res., 8:285-291 (1991).

Artsaenko et al., Expression of a single-chain Fv antibody against abscisic acid creates a willy phenotype in transgenic tobacco, The Plant J., 8:745-750 (1995).

Bezabeh et al., Insertion of scFv into the hinge domain of full-length IgGI monoclonal antibody results in tetravalent bi specific molecule with robust properties, MABS., 9:240-256 (2016).

Bird et al., Single-chain antigen-binding proteins, Science, 242:423-426 (1988).

Bruhl et al., Depletion of CCR5-expressing cells with bispecific antibodies and chemokine toxins: a new strategy in the treatment of chronic inflammatory diseases and HIV, J. Immunol., 166:2420-2426 (2001).

Carter et al., High level *Escherichia coli* expression and production of a bivalent humanized antibody fragment, Biotechnology, 10:163-167 (1992).

Chalfie et al., Green fluorescent protein as a marker for gene expression, Science, 263:802-805 (1994).

Chames et al., Bispecific antibodies for cancer therapy: the light at the end of the tunnel?, MABS., 1:539-547 (2009).

Cheadle et al., Cloning and expression of the variable regions of mouse myeloma protein MOPC315 in *E. coli*: recovery of active FV fragments, Mol. Immunol., 29:21-30 (1992).

Chen et al., Immunoglobulin gene rearrangement in B cell deficient mice generated by targeted deletion of the JH locus, International Immunology, 5:647-656 (1993).

Cheson et al., Report of an international workshop to standardize response criteria for non-Hodgkin's lymphomas. NCI Sponsored International Working Group., J. Clin. Oncol., 17:1244 (1999).

Chi et al., Physical stability of proteins in aqueous solution: mechanism and driving forces in nonnative protein aggregation., Pharm. Res., 20:1325-1336 (2003).

Choi et al., Transgenic mice containing a human heavy chain immunoglobulin gene fragment cloned in a yeast artificial chromosome, Nature Genetics, 4:117-123 (1993).

Chothia et al., Canonical structures for the hypervariable regions of immunoglobulins, J. Mol. Biol., 196:901-917 (1987).

Chothia et al., Conformations of immunoglobulin hypervariable regions, Nature, 342:877-883 (1989).

Clackson et al., Making antibody fragments using phage display libraries, Nature, 352:624-628 (1991).

Cole et al., Monoclonal Antibodies and Cancer Therapy, Alan R. Liss, Inc., 77-96 (1985).

Cook et al., The human immunoglobulin VH repertoire, Immunol. Today, 16:237-242 (1995).

Creighton, Proteins: Structure and molecular properties, W. H. Freeman & Co., San Francisco, 79-86 (1983).

Cunningham et al., High-resolution epitope mapping of hGH-receptor interactions by alanine-scanning mutagenesis, Science, 244:1081-1085 (1989).

Dall'Acqua et al., Contribution of domain interface residues to the stability of antibody CH3 domain homodimers, Biochem., 37:9266-9273 (1998).

Devereux et al., A comprehensive set of sequence analysis programs for the VAX, Nucl. Acids Res., 12:387-395 (1984).

Duskin et al., Relationship of the structure and biological activity of the natural homologues of tunicamycin, J. Biol. Chem., 257:3105-3109 (1982).

Edge et al., Deglycosylation of glycoproteins by trifluoromethanesulfonic acid, Anal. Biochem., 118:131-137 (1981).

Eppstein et al., Biological activity of liposome-encapsulated murine interferon gamma is mediated by a cell membrane receptor, Proc. Natl. Acad. Sci. U.S.A., 82:3688-3692 (1985).

Fecker et al., Expression of single-chain antibody fragments (scFv) specific for beet necrotic yellow vein virus coat protein or 25 kDa protein in *Escherichia coli* and Nicotiana benthamiana, Plant. Mol. Biol., 32:979-986 (1996).

Feng et al., Progressive sequence alignment as a prerequisite to correct phylogenetic trees, J. Mol. Evol., 35:351-360 (1987).

Fishwild et al., High-avidity human IgGk monoclonal antibodies from a novel strain of minilocus transgenic mice, Nature Technology, 14:845-851 (1996).

Gabizon et al., Pharmacokinetics and tissue distribution of doxorubicin encapsulated in stable liposomes with long circulation times, J. National Cancer Inst., 81:1484-1488 (1989).

George et al., Macromolecular Sequencing and Synthesis, Selected Methods and Applications, 127-149, Alan R. Liss, Inc., (1988).

Graham et al., Characteristics of a human cell line transformed by DNA from human adenovirus type 5, J. Gen. Virol., 36:59-74 (1977).

Green et al., Antigen-specific human monoclonal antibodies from mice engineered with human Ig heavy and light chain YACs, Nature Genetics, 7:13-21 (1994).

Green et al., Regulation of B cell development by variable gene complexity in mice reconstituted with human immunoglobulin yeast artificial chromosomes, J. Exp. Med., 188:483-495 (1998).

Hakimuddin et al., A chemical method for the deglycosylation of proteins, Arch. Biochem. Biophys., 259:52-57 (1987).

Harlow et al., Using Antibodies: a laboratory manual, CSHL. Press, (1999).

Hawkins et al., Selection of phage antibodies by binding affinity. Mimicking affinity maturation, J. Mol. Biol., 254:889-896 (1992).

Heim et al., Engineering green fluorescent protein for improved brightness, longer wavelengths and fluorescence resonance energy transfer, Curr. Biol., 6:178-182 (1996).

Hiatt et al., Production of antibodies in transgenic plants, Nature, 342:76-78 (1989).

Higgins et al., Fast and sensitive multiple sequence alignments on a microcomputer, Comput. Appl. Biosci., 5:151-153 (1989).

Holliger et al., "Diabodies": small bivalent and bispecific antibody fragments, Proc. Natl. Acad. Sci. U. S. A., 90:6444-6448 (1993).

Holliger et al., Engineered antibody fragments and the rise of single domains, Nature Biotechnology, 23:1126-1136 (2005).

Honjo et al., Immunoglobulin Genes, Academic Press, San Diego, CA, (1995).

Huston et al., Protein engineering of antibody binding sites: recovery of specific activity in an anti-digoxin single-chain Fv analogue produced in *Escherichia coli*, Proc. Natl. Acad. Sci. USA., 85:5879-5883 (1988).

Hwang et al., Hepatic uptake and degradation of unilamellar sphingomyelin/cholesterol liposomes: a kinetic study, Proc. Natl. Acad. Sci. USA, 77:4030-4034 (1980).

Hwang et al., Immunogenicity of engineered antibodies, Methods, 36:3-10 (2005).

Ichiki et al., Regulation of the expression of human C epsilon germline transcript. Identification of a novel IL-4 responsive element, J. Immunol., 150:5408-5417 (1993).

International Preliminary Report on Patentability, PCT App. No. PCT/EP2018/052665, Aug. 15, 2019, 8 pages.

International Search Report and Written Opinion, PCT App. No. PCT/EP2018/052665, Apr. 30, 2018, 13 pages.

Jakobovits et al., US patent Application filed on Dec. 3, 1996., U.S. Appl. No. 08/759,620.

Jones et al., Replacing the complementarity-determining regions in a human antibody with those from a mouse, Nature, 321:522-525 (1986).

Kabat et al., Tabulation and analysis of amino acid and nucleic acid sequences of precursors, V-regions, C-regiohs, J-chain, T-cell recep-

(56) References Cited

OTHER PUBLICATIONS tors for antigen, T-cell surface antigens, (Beta)2-microglobulins, major histocompatibility antigens, Thy-1, Complement, C-reactive protein, thymopoietin, integrins, post-gamma globulin, (Alpha)2-macroglobulins, and other related proteins, Sequences of proteins of immunological interest, Fifth edition, 1:1 (1991).

Karlin et al., Applications and statistics for multiple high-scoring segments in molecular sequences, Proc. Natl. Acad. Sci. U.S.A., 90:5873-5787 (1993).

Kay et al., US patent Application filed on Aug. 29, 1990., U.S. Appl. No. 07/574,748.

Kendrick et al., Physical stabilization of proteins in aqueous solution, in: Rational design of stable protein formulations: theory and practice, Pharmaceutical Biotechnology, 13:61-84 (2002).

Kipriyanov et al., Bispecific tandem diabody for tumor therapy with improved antigen binding and pharmacokinetics, J. Mol. Biol., 293:41-56 (1999).

Kohler et al., Continuous cultures of fused cells secreting antibody of predefined specificity, Nature, 256:495-497 (1975).

Kontermann et al., Antibody Engineering, Springer, 2nd ed. (2010).

Kontermann, Dual targeting strategies with bispecific antibodies, MABS., 4:182-197 (2012).

Kozbor et al., The production of monoclonal antibodies from human lymphocytes, Immunology Today, 4:72-79 (1983).

Kucherlapati et al., U.S. Appl. No. 08/462,837.

Kucherlapati et al., U.S. Appl. No. 08/464,584.

Kucherlapati et al., US patent Application filed Apr. 27, 1995., U.S. Appl. No. 08/430,938.

Kucherlapati et al., US patent Application filed Apr. 28, 1994., U.S. Appl. No. 08/234,145.

Kucherlapati et al., US patent Application filed Aug. 27, 1993., U.S. Appl. No. 08/112,848.

Kucherlapati et al., US patent Application filed Jan. 12, 1990., U.S. Appl. No. 07/466,008.

Kucherlapati et al., US patent Application filed Jul. 24, 1992., U.S. Appl. No. 07/919,297.

Kucherlapati et al., US patent Application filed Jun. 5, 1995., U.S. Appl. No. 08/463,191.

Kucherlapati et al., US patent Application filed Nov. 8, 1990., U.S. Appl. No. 07/610,515.

Kufer et al., A revival of bispecific antibodies, Trends in Biotechnology, 22:238-244 (2004).

Kufer et al., Construction and biological activity of a recombinant bispecific single-chain antibody designed for therapy of minimal residual colorectal cancer, Cancer Immunol. Immunother., 45:193-197 (1997).

Langer et al., Biocompatibility of polymeric delivery systems for macromolecules, J. Biomed. Mater. Res., 5:267-277 (1981).

Langer, Controlled release of macromolecules, Chem. Tech., 12:98-105 (1982).

Little, Recombinant antibodies for immunotherapy, Cambridge University Press, (2009).

Loffler et al., A recombinant bispecific single-chain antibody, CD19 x CD3, induces rapid and high lymphoma-directed cytotoxicity by unstimulated T lymphocytes, Blood, 95:2098-2103 (2000).

Lonberg et al., Antigen-specific human antibodies from mice comprising four distinct genetic modifications, Nature, 368:856-859 (1994).

Lonberg et al., U.S. Appl. No. 08/155,301.

Lonberg et al., U.S. Appl. No. 08/161,739.

Lonberg et al., U.S. Appl. No. 08/165,699.

Lonberg et al., US patent Application filed Aug. 31, 1990., U.S. Appl. No. 07/575,962.

Lonberg et al., US patent Application filed Jul. 23, 1992., U.S. Appl. No. 07/904,068.

Lonberg et al., US patent Application filed Mar. 9, 1994., U.S. Appl. No. 08/209,741.

Lowman et al., Selecting high-affinity binding proteins by monovalent phage display, Biochemistry, 30:10832-10838 (1991).

Lu et al., A fully human recombinant IgG-like bispecific antibody to both the epidermal growth factor receptor and the insulin-like growth factor receptor for enhanced antitumor activity, J. Biol. Chem., 280:19665-19672 (2005).

MacCallum et al., Antibody-antigen interactions: contact analysis and binding site topography, J. Mol. Biol., 262:732-745 (1996).

Mack et al., A small bispecific antibody construct expressed as a functional single-chain molecule with high tumor cel cytotoxicity, Proc. Natl. Acad. Sci., 92:7021-7025 (1995).

Mack et al., Biologic properties of a bispecific single-chain antibody directed against 17-1A (EpCAM) and CD3: tumor cell-dependent T cell stimulation and cytotoxic activity, J. Immunol., 158:3965-3970 (1997).

Mahler et al., Protein aggregation: pathways, induction factors and analysis, J. Pharm. Sci., 98:2909-2934 (2009).

Malmborg et al., BIAcore as a tool in antibody engineering, J. Immunol. Methods, 183:7-13 (1995).

Marks et al., By-passing immunization. Human antibodies from V-gene libraries displayed on phage, J. Mol. Biol., 222:581-597 (1991).

Martin et al., Irreversible coupling of immunoglobulin fragments to preformed vesicles. An improved method for liposome targeting, J. Biol. Chem., 257:286-288 (1982).

Martin et al., Structural families in loops of homologous proteins: automatic classification, modelling and application to antibodies, J. Mol. Biol., 263:800-815 (1996).

Mather et al., Culture of testicular cells in hormone-supplemented serum-free medium, Annals N. Y. Acad. Sci., 83:44-68 (1982).

Mather, Establishment and characterization of two distinct mouse testicular epithelial cell lines, Biol. Reprod., 23:243-252 (1980).

Matt et al., The european medicines agency review of tegafur/gimeracil/Oteracil (Teysuno (Trademark)) for the treatment of advanced gastric cancer when given in combination with cisplatin: Summary of the scientific assessment of the committee for medicinal products for human use (CHMP), The Oncologist, 1451-1457 (2009).

Mendez et al., Functional transplant of megabase human immunoglobulin loci recapitulates human antibody response in mice, Nature Genetics, 15:146-156 (1997).

Meyer et al., Antimicrobial preservative use in parenteral products: past and present, J. Pharm. Sci., 96:3155-3167 (2007).

Michaelson et al., Anti-tumor activity of stability-engineered IgG-like bispecific antibodies targeting TRAIL-R2 and LTbetaR, MABS., 1:128-141 (2009).

Morrison et al., Chimeric human antibody molecules: mouse antigen-binding domains with human constant region domains, Proc. Natl. Acad. Sci U.S.A., 81:6851-6855 (1984).

Morrison et al., Combinatorial alanine-scanning, Cur. Opin. Chem. Biol., 5:302-307 (2001).

Morrison, Transfectomas provide novel chimeric antibodies, Science, 229:1202-1207 (1985).

Needleman et al., A general method applicable to the search for similarities in the amino acid sequence of two proteins, J. Mol. Biol., 48:443-453 (1970).

Nolan et al., Fluorescence-activated cell analysis and sorting of viable mammalian cells based on beta-D-galactosidase activity after transduction of Escherichia coli lacZ, Proc. Natl. Acad. Sci. U.S.A., 85:2603-2607 (1988).

Oi et al., Chimeric antibodies, BioTechniques, 4:214-221 (1986).

Olsson et al., Human—human monoclonal antibody-producing hybridomas: technical aspects, Meth. Enzymol., 92:3-16 (1982).

Owen et al., Synthesis of a functional anti-phytochrome single-chain Fv protein in transgenic tobacco, Biotechnology, 10:790-794 (1992).

Padlan, Anatomy of the antibody molecule, Mol. Immunol., 31:169-217 (1994).

Pearson et al., Improved tools for biological sequence comparison, Proc. Nat. Acad. Sci. U.S.A., 85:2444-2448 (1988).

Presta, Antibody Engineering, Curr. Opin. Struct. Biol., 2:593-596 (1992).

Raag et al., Single-chain Fvs, FASEB. J., 9:73-80 (1995).

Randolph et al., Surfactant-protein interactions, Pharm. Biotechnol., 13:159-175 (2002).

(56)                     References Cited

OTHER PUBLICATIONS

Reichmann et al., Reshaping human antibodies for therapy, Nature, 332:323-329 (1988).

Remington's Pharmaceutical Sciences, 22nd edition, Oslo, A., Ed., (2012).

Roberts, Therapeutic protein aggregation: mechanisms, design, and control, Trends Biotechnol., 32:372-380 (2014).

Rosenberg et al., Single chain antibodies are discussed in detail by Pluckthun in the Pharmacology of Monoclonal Antibodies, Springer-Verlag, New York, 113:269-315 (1994).

Sambrook et al., Molecular cloning: A laboratory manual, Cold Spring Harbor Laboratory Press, New York, (2001).

Schier et al., Efficient in vitro affinity maturation of phage antibodies using BIAcore guided selections, Human Antibodies Hybridomas, 7:97-105 (1996).

Schlereth et al., T-cell activation and B-cell depletion in chimpanzees treated with a bispecific anti-CD19/anti-CD3 single-chain antibody construct, Cancer Immunol. Immunother., 20:1-12 (2005).

Shen et al., Single variable domain-IgG fusion. A novel recombinant approach to Fc domain-containing bispecific antibodies, J. Biol. Chem., 281:10706-10714 (2006).

Sidman et al., Controlled release of macromolecules and pharmaceuticals from synthetic polypeptides based on glutamic acid, Biopolymers, 2:547-556 (1983).

Skerra et al., Assembly of a functional immunoglobulin Fv fragment in *Escherichia coli*, Science, 242:1038-1041 (1988).

Smith et al., Comparison of biosequences, Advances in Applied Mathematics, 2:482-489 (1981).

Smith, Filamentous fusion phage: novel expression vectors that display cloned antigens on the virion surface, Science, 228:1315-1317 (1985).

Songsivilai et al., Bispecific antibody: a tool for diagnosis and treatment of disease, Clin. Exp. Immunol., 79-815-321 (1990).

Spiess et al., Alternative molecular formats and therapeutic applications for bispecific antibodies, Mol. Immunol., 67(2 Pt A):95-106 (2015).

Spreter et al., Improving biophysical properties of a bispecific antibody scaffold to aid developability quality by molecular design, MABS, Landes Bioscience, 5:646-654 (2013).

Stauber et al., Development and applications of enhanced green fluorescent protein mutants, Biotechniques, 24:462-471 (1998).

Takeda et al., Construction of chimaeric processed immunoglobulin genes containing mouse variable and human constant region sequences, Nature, 314:452-454 (1985).

Taylor et al., A transgenic mouse that expresses a diversity of human sequence heavy and light chain immunoglobulins, Nucleic Acids Research, 20:6287-6295 (1992).

Taylor et al., Human immunoglobulin transgenes undergo rearrangement, somatic mutation and class switching in mice that lack endogenous IgM, Int. Immunology, 6:579-591 (1994).

Taylor, Engineering bispecific antibodies for targeted delivery of cytotoxin-loaded nanoparticles to tumour cells the australian institute for bioengineering and nanotechnology (AIBN), (2015).

Teng et al., Construction and testing of mouse—human heteromyelomas for human monoclonal antibody production, Proc. Natl. Acad. Sci. U S A., 80:7308-7312 (1983).

Thotakura et al., Enzymatic deglycosylation of glycoproteins, Methods Enzymol., 138:350-359 (1987).

Tomlinson et al., The repertoire of human germline VH sequences reveals about fifty groups of VH segments with different hypervariable loops, J. Mol. Biol., 227:776-798 (1992).

Tomlinson et al., The structural repertoire of the human V kappa domain, EMBO. J., 14::4628-4638 (1995).

Tuaillon et al., Analysis of direct and inverted DJH rearrangements in a human Ig heavy chain transgenic minilocus, J. Immunol., 154:6453-6465 (1995).

Tuaillon et al., Human immunoglobulin heavy-chain minilocus recombination in transgenic mice: Gene-segment use in (Mue) and (Gamma) transcripts, Proc. Natl. Acad. Sci. USA., 90:3720-3724 (1993).

U.S. Appl. No. 08/376,279.

U.S. Appl. No. 08/486,853.

U.S. Appl. No. 08/486,859.

Urlaub et al., Isolation of Chinese hamster cell mutants deficient in dihydrofolate reductase activity, Proc. Natl. Acad. Sci. U S A., 77:4216-4220 (1980).

Wang, Instability, stabilization, and formulation of liquid protein pharmaceuticals, Int. J. Pharm., 185:129-188 (1999).

Ward et al., Binding activities of a repertoire of single immunoglobulin variable domains secreted from *Escherichia coli*, Nature, 341:544-546 (1989).

Wu et al., Simultaneous targeting of multiple disease mediators by a dual-variable-domain immunoglobulin, Nat. Biotechnol., 25:1290-1297 (2007).

Zuo et al., An efficient route to the production of an IgG-like bispecific antibody, Protein Eng., 13:361-367 (2000).

\* cited by examiner a) Bispecific single chain Fc antibody construct hinge

CH2

CH3 linker $\begin{smallmatrix} C \\ C \end{smallmatrix}$ = intra chain disulfide bond X = Glycosylation site removed b) Bispecific HeteroFc antibody construct hinge

CH2

CH3

●● = Charge pairing sites c) Bispecific X-body construct

●● = Charge pairing sites d) Bispecific human albumin fusion construct

HSA

Figure 4 (a)
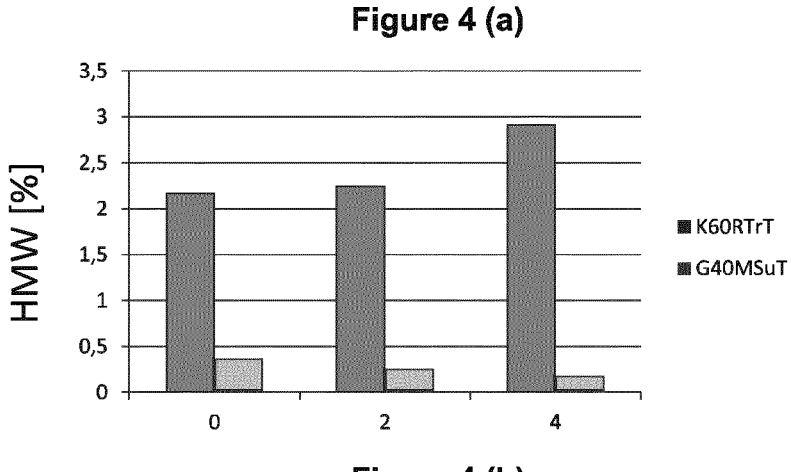
Figure 4 (b)
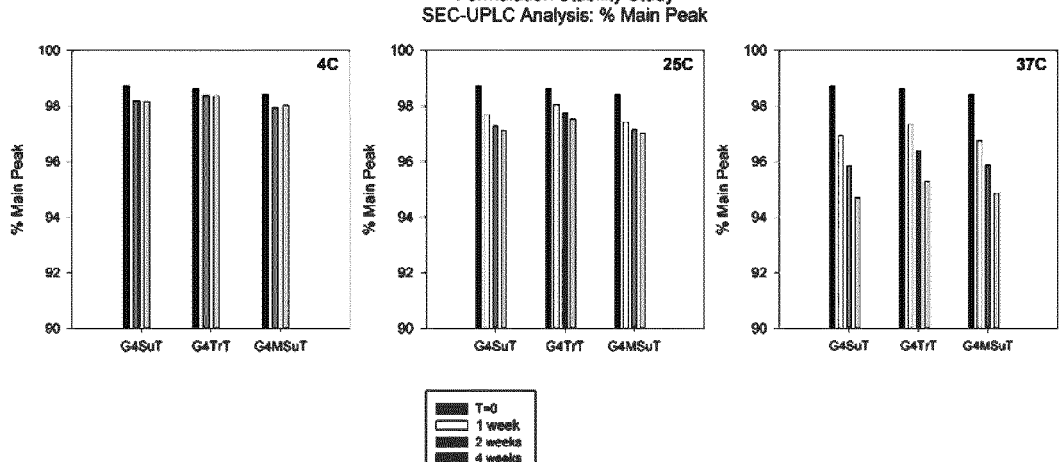
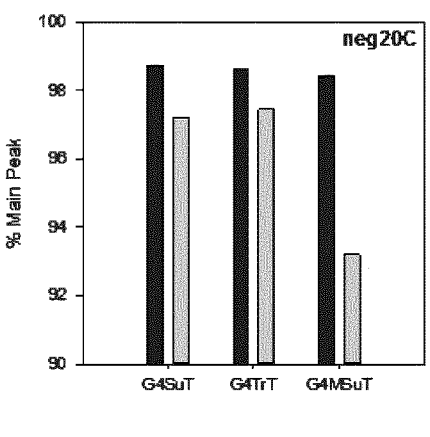
Figure 4 (c)

CDH19 scFc MA
Formulation Stability Study
SEC-UPLC Analysis: % HMW

CDH19 scFc MA
Formulation Stability Study
SEC-UPLC Analysis: % HMW

EGFRvIII main peak at various temperatures and pH conditions

LOW pH PHARMACEUTICAL COMPOSITION COMPRISING T CELL ENGAGING ANTIBODY CONSTRUCTS

BACKGROUND

Protein-based pharmaceuticals are among the fastest growing therapeutic agents in (pre)clinical development and as commercial products. In comparison with small chemical drugs, protein pharmaceuticals have high specificity and activity at relatively low concentrations, and typically provide for therapy of high impact diseases such as various cancers, auto-immune diseases, and metabolic disorders (Roberts, Trends Biotechnol. 2014 July; 32(7):372-80, Wang, *Int J Pharm.* 1999 Aug. 20; 185(2):129-88).

Protein-based pharmaceuticals, such as recombinant proteins, can now be obtained in high purity when first manufactured due to advances in commercial scale purification processes. However, proteins are only marginally stable and are highly susceptible to degradation, both chemical and physical. Chemical degradation refers to modifications involving covalent bonds, such as deamidation, oxidation, cleavage or formation of new disulfide bridges, hydrolysis, isomerization, or deglycosylation. Physical degradation includes protein unfolding, undesirable adsorption to surfaces, and aggregation. Dealing with these physical and chemical instabilities is one of the most challenging tasks in the development of protein pharmaceuticals (Chi et al., Pharm Res, Vol. 20, No. 9, September 2003, pp. 1325-1336, Roberts, Trends Biotechnol. 2014 July; 32(7):372-80).

Interesting protein-based pharmaceuticals include bispecific molecules such as BiTE®×(bispecific T cell engager) antibody constructs which are recombinant protein constructs made from two flexibly linked antibody derived binding domains. One binding domain of BiTE® antibody constructs is specific for a selected tumor-associated surface antigen on target cells; the second binding domain is specific for CD3, a subunit of the T cell receptor complex on T cells. By their particular design BiTE® antibody constructs are uniquely suited to transiently connect T cells with target cells and, at the same time, potently activate the inherent cytolytic potential of T cells against target cells. An important further development of the first generation of BiTE® antibody constructs (see WO 99/54440 and WO 2005/040220) developed into the clinic as AMG 103 and AMG 110 was the provision of bispecific antibody constructs binding to a context independent epitope at the N-terminus of the CD3E chain (WO 2008/119567). BiTE® antibody constructs binding to this elected epitope do not only show cross-species specificity for human and *Callithrix jacchus*, *Saguinus oedipus* or *Saimiri sciureus* CD3ε chain, but also, due to recognizing this specific epitope instead of previously described epitopes for CD3 binders in bispecific T cell engaging molecules, do not unspecifically activate T cells to the same degree as observed for the previous generation of T cell engaging antibodies. This reduction in T cell activation was connected with less or reduced T cell redistribution in patients, which was identified as a risk for side effects.

Antibody constructs as described in WO 2008/119567 are likely to suffer from rapid clearance from the body; thus, whilst they are able to reach most parts of the body rapidly, and are quick to produce and easier to handle, their in vivo applications may be limited by their brief persistence in vivo. Prolonged administration by continuous intravenous infusion was used to achieve therapeutic effects because of the short in vivo half life of this small, single chain molecule. However, such continuous intravenous infusions are classified as inconvenient for the patients and, thus, in case of more convenient alternative treatment approaches, hamper the election of the compound demonstrated to be more efficient in the treatment of the respective disease. Hence, Applicant has introduced bispecific therapeutics that retain similar therapeutic efficacy that have a format which is straightforward to produce, and that have favorable pharmacokinetic properties, including a longer half-life.

An increased half-life is generally useful in in vivo applications of immunoglobulins, especially antibodies and most especially antibody fragments of small size. Approaches described in the art to achieve such effect comprise the fusion of the small bispecific antibody construct to larger proteins, which preferably do not interfere with the therapeutic effect of the BiTE® antibody construct. Examples for such further developments of bispecific T cell engagers comprise bispecifc Fc-molecules e.g. described in US 2014/0302037, US 2014/0308285, WO 2014/144722, WO 2014/151910 and WO 2015/048272.

Protein aggregation represents a major event of physical instability of proteins and occurs due to the inherent tendency to minimize the thermodynamically unfavorable interaction between the solvent and hydrophobic protein residues. It is particularly problematic because it is encountered routinely during refolding, purification, sterilization, shipping, and storage processes. Aggregation can occur even under solution conditions where the protein native state is highly thermodynamically favored (e.g., neutral pH and 37° C.) and in the absence of stresses (Chi et al., Pharm Res, Vol. 20, No. 9, September 2003, pp. 1325-1336, Roberts, Trends Biotechnol. 2014 July; 32(7):372-80, Wang, Int J Pharm. 1999 Aug. 20; 185(2):129-88, Mahler J Pharm Sci. 2009 September; 98(9):2909-34).

Also half-life extended antibody constructs such as of bispecific T cell engagers comprising a half-life extending modality such as Fc-molecules have to be protected against protein aggregation and/or other degradation events. Protein aggregation is problematic because it can impair biological activity of the therapeutic proteins. Moreover, aggregation of proteins leads to undesirable aesthetics of the drug product, and decreases product yield due to elaborate purification steps that are required to remove the aggregates from the end product. More recently, there has also been growing concern and evidence that the presence of aggregated proteins (even humanized or fully human proteins) can significantly increase the risk that a patient will develop an immune response to the active protein monomer, resulting in the formation of neutralizing antibodies and drug resistance, or other adverse side effects (Mahler J Pharm Sci. 2009 September; 98(9):2909-34.

In general, several efforts have been reported in the literature to minimize protein aggregation by various mechanisms. Proteins can be stabilized and thus protected from aggregate formation and other chemical changes by modifying their primary structure, thereby increasing interior hydrophobicity and reducing outer hydrophobicity. However, genetic engineering of proteins may result in impaired functionality and/or increased immunogenicity. Another approach focuses on the dissociation of aggregates (referred to as "disaggregation") to recover functional, native monomers by using various mechanisms such as temperature, pressure, pH, and salts. Currently, protein aggregates are removed as impurities mainly in the polishing steps of downstream processing. However, in cases of high levels of high-molecular weight (HMW), removing significant amount of HMW not only results in substantial yield loss but also makes the design of a robust downstream process challenging (Chi et al., Pharm Res, Vol. 20, No. 9, September 2003, pp. 1325-1336).

Preserving protein stability and activity in biological and biotechnological applications poses serious challenges. There is a need in the art for optimized pharmaceutical compositions that provide for enhanced stabilization of therapeutic proteins and reduce aggregation and denaturation or degradation during formulation, filling, shipping, storage and administration, thereby preventing loss-of-function and adverse immunogenic reactions. It is the object of the present invention to comply with this need, especially with regard to half-life extended antibody constructs such as of bispecific T cell engagers comprising a half-life extending modality such as Fc-molecules.

SUMMARY

Protein-based pharmaceuticals including bispecific (and/or multispecific) antibodies that bind to two (or more) different antigens simultaneously, such as bispecific T cell engaging antibody constructs, are prone to protein instability. This extends to those antibody contracts comprising half-life extending formats (HLE formats) which include the single chain Fc format (designated scFc), the hetero Fc (also designated as hetFc or heterodimeric Fc, hFc) format and the fusion of human serum albumin (also designated as HSA or hALB). Protein instability, and in particular protein aggregation, is an increasing challenge in the biotechnology industry, where aggregation is encountered throughout the lifetime of a therapeutic protein, including during refolding, purification, sterilization, shipping, and storage processes. It is thus the object of the present invention to provide a stable pharmaceutical composition comprising an antibody construct, preferably half-life extending format, further preferably a T cell engaging antibody construct. In the context of the present invention, a pharmaceutical composition, which is preferably a liquid composition or may be a solid composition obtained by lyophilisation or may be a reconstituted liquid composition comprises (a) an antibody construct comprising at least three domains, wherein:

a first domain binds to a target cell surface antigen and has an isoelectric point (pl) in the range of 4 to 9, 5;
  a second domain binds to a second antigen; and has a pl in the range of 8 to 10, preferably 8.5 to 9.0; and
  preferably a third domain comprises two polypeptide monomers, each comprising a hinge, a CH2 domain and a CH3 domain, wherein said two polypeptide monomers are fused to each other via a peptide linker;

(b) at least one buffer agent;
(c) at least one saccharide; and
(d) at least one surfactant;
and wherein the pH of the pharmaceutical composition is in the range of 3.5 to 6.

It is envisaged in the context of the present invention that the pharmaceutical composition comprises an antibody construct which is a single chain antibody construct.

It is further envisaged in the context of the present invention that the said third domain comprises an amino to carboxyl order: hinge-CH2 domain-CH3 domain-linker-hinge-CH2 domain-CH3 domain.

It is especially envisaged in the context of the present invention that the antibody construct according to the present invention comprises the third domain.

It is also envisaged in the context of the present invention that the first domain has a pl in the range of about 4.0 to about 9.5, preferably of about 4.5 to 7.5, or 4.5 to 6.5.

It is envisaged in the context of the present invention that the target cell surface antigen is a tumor antigen, an antigen specific for an immunological disorder or a viral antigen.

It is further envisaged in the context of the present invention that the tumor antigen is selected from the group consisting of CDH19, MSLN, DLL3, FLT3, EGFR, EGFRvIII, BCMA, PSMA, CD33, CD19, CD20, and CD70.

It is also envisaged in the context of the present invention that the second domain is an extracellular epitope of CD3 the human and/or the *Macaca* CD3ε chain.

It is envisaged in the context of the present invention that the second domain has a pl in the range of 8.5 to 9.0.

It is further envisaged in the context of the present invention that each of said polypeptide monomers of the third domain has an amino acid sequence that is at least 90% identical to a sequence selected from the group consisting of: SEQ ID NOs: 17-24, or has an amino acid sequence selected from the group consisting of SEQ ID NOs: 17-24.

It is also envisaged in the context of the present invention that the CH2 domain comprises an intra domain cysteine disulfide bridge.

It is envisaged in the context of the present invention that the third domain has a pl in the range of 5.5 to 7.5, preferably 6.0 to 7.0.

It is further envisaged in the context of the present invention that (i) the first domain comprises two antibody variable domains and the second domain comprises two antibody variable domains;
(ii) the first domain comprises one antibody variable domain and the second domain comprises two antibody variable domains;
(iii) the first domain comprises two antibody variable domains and the second domain comprises one antibody variable domain; or
(iv) the first domain comprises one antibody variable domain and the second domain comprises one antibody variable domain.

It is envisaged in the context of the present invention that the antibody construct preferably comprises in an amino to carboxyl order:

(a) the first domain;
(b) a peptide linker having an amino acid sequence selected from the group consisting of SEQ ID NOs: 1-3;
(c) the second domain;
(d) a peptide linker having an amino acid sequence selected from the group consisting of SEQ ID NOs: 1, 2, 3, 9, 10, 11 and 12;
(e) the first polypeptide monomer of the third domain;
(f) a peptide linker having an amino acid sequence selected from the group consisting of SEQ ID NOs: 5, 6, 7 and 8; and
(g) the second polypeptide monomer of the third domain.

It is also envisaged in the context of the present invention that the at least one buffer agent is an acid selected from the group consisting of acetate, glutamate, citrate, succinate, tartrate, fumarate, maleate, histidine, phosphate, 2-(N-morpholino)ethanesulfonate or a combination thereof.

It is further envisaged in the context of the present invention that the at least one buffer agent is present at a concentration range of 5 to 200 mM, more preferably at a concentration range of 10 to 50 mM.

It is envisaged in the context of the present invention that the at least one saccharide is selected from the group consisting of monosaccharide, disaccharide, cyclic polysaccharide, sugar alcohol, linear branched dextran or linear non-branched dextran.

It is also envisaged in the context of the present invention that the disacchade is selected from the group consisting of sucrose, trehalose and mannitol, sorbitol, and combinations thereof.

It is further envisaged in the context of the present invention that the sugar alcohol is sorbitol.

It is envisaged in the context of the present invention that the at least one saccharide is present at a concentration in the range of 1 to 15% (m/V), preferably in a concentration range of 9 to 12% (m/V).

It is also envisaged in the context of the present invention that the at least one surfactant is selected from the group consisting of polysorbate 20, polysorbate 40, polysorbate 60, polysorbate 80, poloxamer 188, Pluronic® F68, Polyethylene glycol p-(1,1,3,3-tetramethylbutyl)-phenyl ether, polyoxyethylen, PEG 3350, PEG 4000 and combinations thereof.

It is further envisaged in the context of the present invention that the at least one surfactant is present at a concentration in the range of 0.004 to 0.5% (m/V), preferably in the range of 0.001 to 0.01% (m/V).

It is envisaged in the context of the present invention that the pH of the composition is in the range of 4.0 to 5.0, preferably 4.2.

It is also envisaged in the context of the present invention that the pharmaceutical composition has an osmolarity in the range of 150 to 500 mOsm.

It is further envisaged in the context of the present invention that the pharmaceutical composition further comprises an excipient selected from the group consisting of, one or more polyol and one or more amino acid.

It is envisaged in the context of the present invention that said one or more excipient is present in the concentration range of 0.1 to 15% (w/V).

It is also envisaged in the context of the present invention that the pharmaceutical composition comprises (a) the antibody construct of any one of the preceding claims, (b) 10 mM glutamate or acetate, (c) 9% (m/V) sucrose or 6% (m/V) sucrose and 6% (m/V) hydroxypropyl-β-cyclodextrin, (d) 0.01% (m/V) polysorbate 80 and wherein the pH of the liquid pharmaceutical composition is 4.2.

It is further envisaged in the context of the present invention that the antibody construct is present in a concentration range of 0.1 to 8 mg/ml, preferably of 0.2-2.5 mg/ml, more preferably of 0.25-1.0 mg/ml.

It is envisaged in the context of the present invention that the pharmaceutical composition of the present invention is liquid.

It is also envisaged in the context of the present invention that the pharmaceutical composition is a solid pharmaceutical composition, obtainable by lyophilisation of the liquid pharmaceutical composition of any one of the preceding claims.

It is further envisaged in the context of the present invention that the pharmaceutical composition is a liquid pharmaceutical composition obtainable by reconstituting the solid pharmaceutical composition obtainable by lyphilisation with a pharmaceutically acceptable liquid.

It is envisaged in the context of the pharmaceutical composition is for use in the treatment of a disease, preferably of a proliferative disease, an immunological disease or a viral disease.

It is also envisaged in the context of the present invention that the composition is administrated parenterally, preferably i.v. by infusion or injection.

It is further envisaged in the context of the present invention that the composition is administrated 1, 2, 3, 4, 5, 6 or 7 times per week, or 1, 2, 3, 4, 5 or 6 times every two weeks, or 1 or 2 times per month, or 1 or 2 times every two months, most preferably 1 time per week.

DESCRIPTION OF THE FIGURES

FIG. 1a shows a diagram of one embodiment of an antibody construct of the invention. FIG. 1b shows a heterodimeric Fc antibody construct and Ic a X-body construct described in the art. The indicated charged pairs are introduced in order to enforce the heterodimerization. FIG. 1d shows the fusion of an antibody construct with a human serum albumin (HSA or hALB).

DETAILED DESCRIPTION

Despite the high quality of current therapeutic biotech products and the resemblance of recombinant human proteins and antibodies to endogenous human proteins, protein instability remains an important concern. In addition to the quality-related consequences of protein aggregation such as possible loss of protein activity and undesirable aesthetics of drug product, soluble protein aggregates have been reported to have significant cytotoxic effects, and, importantly, are a potential risk factor for the development of an the immune response to protein products. Protein aggregation can occur during at various points throughout the lifetime of a protein, including fermentation, refolding, purification, filling, shipment, storage or administration and is strongly dependent on various environmental factors. There is a critical need in the art to increase stability and reduce aggregation of therapeutic proteins; and optimized pharmaceutical formulations can aid in doing so.

Specific protein-based pharmaceuticals such as BiTE® antibody constructs molecules are not stable in liquid formulations over a longer period of time and especially not at accelerated temperatures, e.g. refrigeration temperature 4° C. and above. Initial examination of BiTE® antibody constructs, both non-HLE and HLE variants, by differential scanning calorimetry typically exhibit a higher thermal stability at neutral than at acid pH values, e.g. showing a lower stability at pH 4 versus pH 6 or pH 7. Thus, a person skilled in the art would suggest that the solution stability of such antibody constructs should decrease. Consequently, a person skilled in the art would avoid low pH formulations for antibody constructs according to the present invention as he or she would assume destabilized scFv which is generally to be avoided. Hence, it was a very surprising finding that to the contrary antibody constructs according to the present invention are even more stable in a liquid pharmaceutical composition having a low pH value.

Figure 2:
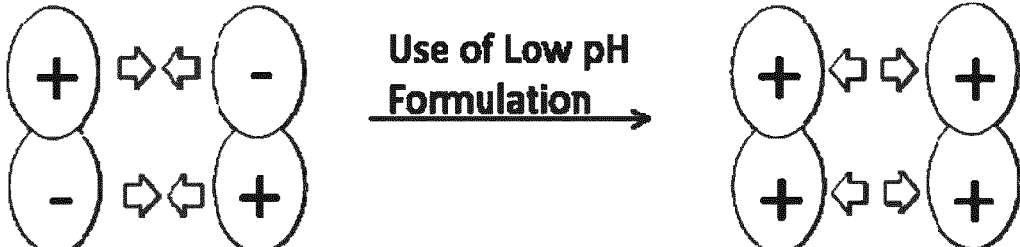
FIG. 2: Schematic representation of antibody construct domains being differently charged at about neutral pH and similarly positively charged at lower pH.

A general concept underlying the present invention is the finding that colloidal stability of a liquid pharmaceutical composition comprising an antibody constructs according to the present invention is improved at low pH. The antibody constructs of the present invention typically have different isoelectric point (pI) values for their first and second domain. In addition, also the pI of the third domain typically differs from the pI of the second domain. Under physiological conditions, the first and/or the third domain may normally be negatively charged as the pI is more to the acid side, e.g. having a pI of about 4.0, 4.5, 5.0, 5.5, 6.0, or 6, 5. Even if the first domain had a pI above 6, 5, e.g. about 7.0, 7.5, 8.0 or 8.5, this pI would typically be lower than that of the second domain, which normally has a pI of 8.0 to 10.0, more typically of about 8.5 to 9.5, preferably about 9.2. In addition, the third domain normally has a slightly acidic pI pf 6.0 to 7.0, which means that even if the pI of the first domain is slightly basic, there remains a difference in pI between the second and the third domain. In consequence, any pI difference wherein at least one domain has an acidic pI and another domain as a basic pI, a dipole will result under physiologic conditions because the different domains are differently, i.e. oppositely charged. Said opposite charges may lead to intra-nad intermolecular electrostatic attractions which in turn may lead to aggregation and, thus, to the formation of undesired high molecular weight (HMW) species. Said formation may crucially impact the stability of the solution or the colloidal stability of the dispersion. However, if the pH of the medium is lowered, all domains get protonated and electrostatic repulsion takes place (see FIG. 2).

For example, it was found that at pH 7 an antibody construct comprising a first domain against CD19 and a second domain against CD3 forms a dipole due to the positive charge on the T-cell engaging domain and negative charge on the CD19 domain. This leads to attractive forces and consequently aggregation which leads to colloidal instability. At about pH 4 both domains are positively charged and charge repulsion improves colloidal stability.

In addition, even if the pI of the first and the second domain are close to each other, respectively, e.g. about 8.0 of the first domain and about 8.5 or 9.0 or 9.5 of the second domain, both domains are already positively charged at a pH value lower than 8. At an even lower pH of, e.g., about 4 the two domains, e.g. the target and T-cell engaging domain, are heavily positively charged. This leads to an even increased charge-charge repulsion and, in consequence, to demonstrably higher colloidal stability. This effect is supplemented in case of the presence of the third domain typically having a pI in the slightly acidic range and, thus, being always different from the second domain with regard to the pI. In summary, an antibody construct according to the present invention always takes benefit from having generally protonated domains in a medium having a low pH such as 6.0 or lower, or 5.5 or lower, or 5.0 or lower, or 4.5 or lower such as 4.2.

The first domain of an antibody construct according to the present invention, which is typically a scFv domain for an oncology target, normally has a different pI than the second domain, which is typically anti-CD3 domain.

Typically the second domain, e.g. an anti-CD3 domain, has a pI in the range of 8 to 10, preferably about 8.5 to 9.5, most preferably about 9.2.

The first domain may have a pI of about 4.9 to 5.3 if the first domain is an anti-CD19 or anti-CD33 domain. The first domain may have a pI of about 6 to 8 or about 9.0 if the first domain is an anti-DLL3 or anti-EGFRvIII domain. The first domain may have a pI of about 8.0 to 8.5 if the first domain is an anti-CD70 domain. The first domain may have a pI of about 7.0 to 7.5 if the first domain is an anti-CDH19 domain. The first domain may have a pI of about 7.0 to 7.5 if the first domain is an anti-PSMA domain. The first domain may have a pI of about 9.0 to 9.5 if the first domain is an anti-MSLN domain. The first domain may have a pI of about 8.5 to 9.5 if the first domain is an anti-Flt3 domain.

It is envisaged in the context of the present invention that the concept of a formulation which stabilizes domains of different pI may be applied to any antibody construct. In the context of the present invention, bispecific antibody constructs comprising a third domain as described herein are especially suitable to be stabilized by a formulation as described herein. However, also other bispecific antibody constructs, e.g. without such a third domain, may be efficiently stabilized according to the present invention. For example, it is envisaged that an antibody construct according to the present invention may have a first domain comprising HCDRs of SEQ ID NOs 1954-1956 and LCDRs of SEQ ID NOs 1958-1960. It is also envisaged that an antibody construct according to the present invention may have a first domain comprising VH of SEQ ID NO 1957 and VL of SEQ ID NOs 1961. It is even more envisaged that the first domain of an antibody construct according to the present invention may have a first domain according to SEQ ID NO 1962. It is also envisaged that an antibody construct according to the present invention may have a sequence according to SEQ ID NO 1963.

However, in the context of the present invention, the stabilizing effect of the pharmaceutical composition is not restricted to antibody constructs having (binding) domains of different pl. Accordingly, it is also envisaged that the present pharmaceutical composition provides a stabilizing formulation to antibody constructs which are provided with moieties of different pl which may, thus, be stabilized by the formulations as described herein. Such moieties may comprise masking moieties which mask binding domains of such antibody constructs, even where the binding domains themselves to not differ in pl in such a way that they would require additional stabilization as provided according to a pharmaceutical composition in the context of the present invention. Typically, such antibody constructs comprising masking moieties are activatable antibody constructs. In the context of the present invention, such an activatable antibody construct my bind to any target cell surface antigen such as a tumor antigen, preferably selected from the group consisting of CDH19, MSLN, DLL3, FLT3, EGFR, EGFRvIII, BCMA, PSMA, CD33, CD19, CD20, and CD70.

Such an activatable antibody construct may be an antibody or an antigen binding fragment thereof that typically comprises (i) at least two binding domains each comprising a heavy chain amino acid sequence and a light chain amino acid sequence, (ii) a masking moiety that inhibits the binding of each binding domain in an uncleaved state to the respective binding partner such as a target cell surface, and (iii) a cleavable moiety positioned between (i) and (ii), wherein the cleavable moiety is a polypeptide that functions as a substrate e.g. for a protease. Typically, the activatable antibody in the uncleaved state has the structural arrangement from N-terminus to C-terminus as follows: masking moiety—cleavable moiety—binding domain or binding domain—cleavable moiety—masking moiety. A pharmaceutical composition according to the present invention may be especially beneficial in conferring stability to the activatable antibody construct where the pl of the at least two masking moieties of the at least two binding domains differ. For example, the pl of one masking moiety may be in the range of 3 to 5, preferably 3.5 to 4.5, more preferably 3.9 to 4.5, while the pl of the other masking moiety is in the range of 5.0 to 7.0, preferably 5.5 to 6.0. In such a case, it is typically found that formulating such an antibody construct in a pharmaceutical composition according to the present invention, the aggregation of said antibody construct can be significantly reduced. Typically, the aggregation in terms of percentile high molecular weight (HMW) species can be significantly reduced, e.g. from about 10% to about 6, 5, 4 or even below 4% due to the same protonation at a low pH and the supplemental stabilizing function of the excipients in a pharmaceutical composition according to the present invention. Percentile HMW species below 4% are typically found in a pharmaceutical composition according to the present invention with a pH of about 4.2 to 4.8.

Preferably, the (solution) pH of a pharmaceutical composition according to the present invention should be lower than the pl of any of the two or three domains of the antibody construct according to the present invention to create a net positive charge for both domains to create both inter and intra domain repulsion. Preferred is a pH value of about 4.0 to 5.5, more preferred 4.2 to 4.8.

It was also surprisingly found that a pharmaceutical composition according to the present invention may comprise an antibody construct according to the present invention at a higher concertation than expected. Normally, antibody constructs as described herein are stored and/or employed in a liquid pharmaceutical composition only at a concentration of about 1 mg/ml. At higher concentrations, aggregation tendencies are observed. However, as explained herein, a lower pH contributes to electrostatic inter and intramolecular repulsion which reduces the risk for aggregation and may allow for a higher antibody construct concentration such as 1.5, 2.0, 2.5, 3.0, 3.5, 4.0, 4.5, 5.0, 5.5, 6.0, 6.5, 7.0, 7.5 or 8.0 mg/ml without (colloidal) instability.

It was further found that pharmaceutical compositions of the present invention are preferred which are free of anorganic anions or salts comprising inorganic anions such as sodium chloride. Tonicity of the pharmaceutical composition of the present invention is preferably adjusted by non-ionic excipients (e.g. sucrose) within the stock keeping unit (SKU). Without wanting to be bound by theory, the reason is that protein formulations can be physically stabilized by selecting formulation pH values that are sufficiently different from the isoelectric point of the molecule in order to favor electrostatic repulsion as described herein. However, these repulsive forces can be weakened through the interaction with ions present in the formulation. Ions, in particular inorganic anions, may minimize or neutralize charges at the surface of the protein and give rise to hydrophobic interactions due to reduction of intramolecular repulsion forces. Accordingly, a pharmaceutical composition according to the present invention is preferably free of inorganic anions. Required buffer compounds preferably only comprise organic anions such as glutamate and/or acetate. Hence, a pharmaceutical composition according to the present invention is preferably free of inorganic anions such as $F^-$, $C^-$, $I^-$ and $Br^-$. In particular, a pharmaceutical composition according to the present invention is preferably free of NaCl.

The increased stability of the antibody construct in a liquid formulation according to the present invention may contribute to save the expensive and laborious step of lyophilisation to obtain a storable solid, i.e. dry pharmaceutical composition. Also, the low pH pharmaceutical composition may be suitable for i.v. administration. However, if e.g. s.c. or i.m. administration is required or if the low pH is not acceptable for other medical reasons, a solid pharmaceutical composition may still be obtained from the liquid pharmaceutical composition according to the present invention. The thus obtained lyophilisate may be reconstituted in an pharmaceutically acceptable medium suitable for the required form of administration or individual medical need. In addition, further stabilizing agents such as Captisol® may be saved by the employment of the present pharmaceutical composition at low pH.

The pharmaceutical composition as presented herein enables the stability of the formulated bispecific antibody constructs. Evaluation of the impact of formulation parameters on different bispecific antibody constructs shows that formulation can be optimized dependent on molecular characteristics including but not limited to the presence of a half-life extending moiety, the IEP or a cys-clamp in target binder. Careful selection of pH optimum and salt content as described herein are critical. As far as stability is concerned, it is possible to correlate isothermal long-term stability study at accelerated storage conditions and stability predicting methods for investigated bispecific antibody constructs, as it also has been shown for monoclonal antibodies before. Bispecific antibody constructs as described herein are overall stable during long-term storage at 30° C. as well as during stability predicting methods, so that part of the investigated parameters remained quite robust, making it challenging to find correlations including e.g. DLS hydrodynamic radius. This phenomenon is compensated by varying formulation conditions in pH and ionic strength, inducing different response of the bispecific antibodies to storage and temperature stress. However, there are stability predicting methods, especially temperature-ramped nanoDSF and temperature-ramped DLS as well as hydrophobic interaction chromatography whose parameters show quite strong and comprehensible correlation to some parameters assessed during isothermal stability study e.g. subvisible particle count, IF ratio 350 nm/330 nm and amount of acidic charge variants. Nevertheless, prediction of aggregation faces challenges as application of linear degradation kinetics to long-term stability was difficult, therefore not excluding stochastic kinetics with lag time and primary accelerated degradation induced by freezing and thawing. Stability predicting techniques as used herein give useful forecast on stability of bispecific antibody constructs in pharmaceutical compositions according to the present invention.

Within the present invention, the term "stability" or "stabilization" relates to the stability of the pharmaceutical composition in total and in particular to the stability of the active ingredient (e.g. the bispecific single chain antibody construct) itself, specifically during formulation, filling, shipment, storage and administration. The terms "stability" or "stable" in the context of the pharmaceutical composition of the invention and the bispecific single chain antibody construct particularly refers to the reduction or prevention of the formation of protein aggregates (HMWS). Specifically, the term "stability" also relates to the colloidal stability of the bispecific single chain antibody constructs comprised within the pharmaceutical composition described herein. "Colloidal stability" is the ability of colloidal particles (such as proteins) to remain dispersed in liquids for a prolonged period of time (days to years).

The term "(protein) aggregate" as used herein generally encompasses protein species of higher molecular weight such as "oligomers" or "multimers" instead of the desired defined species (e.g., a monomer). The term is used interchangeably herein with the terms "high molecular weight species" and "HMWS". Protein aggregates may generally differ in size (ranging from small (dimers) to large assemblies (subvisible or even visible particles) and from the nanometer to micrometer range in diameter), morphology (approximately spherical to fibrillar), protein structure (native vs. non-native/denatured), type of intermolecular bonding (covalent vs. non-covalent), reversibility and solubility. Soluble aggregates cover the size range of roughly 1 to 100 nm, and protein particulates cover subvisible (~0.1–100 .m) and visible (>100 .m) ranges. All of the aforementioned types protein aggregates are generally encompassed by the term. The term "(protein) aggregate" thus refers to all kinds physically-associated or chemically linked non-native species of two or more protein monomers.

The term "protein aggregation" or "non-native aggregation" thus denotes the process(es) by which protein molecules assemble into complexes composed of two or more proteins, with the individual proteins denoted as the monomer. There are multiple pathways leading to protein aggregation that can be induced by a wide variety of conditions, including temperature, mechanical stress such as shaking and stirring, pumping, freezing and/or thawing and formulation.

An increase in temperature accelerates chemical reactions such as oxidation and deamidation of proteins, which can in turn promote aggregation. Higher temperature also directly influences conformation of proteins on the quaternary, tertiary, and secondary structure level, and can lead to temperature-induced unfolding that can promote aggregation. Temperatures referred to in the present application typically are deep freezing temperature for long term storage of delicate protein-based pharmaceuticals (−70° C.), regular freezing temperature (−20° C.), refrigeration temperature (4° C.), room temperature (25° C.) and physiologic temperature (37° C.).

Protein denaturation and aggregation can occur during freeze/thawing due to complex physical and chemical changes such as creation of new ice/solution interfaces, adsorption to container surfaces, cryoconcentration of the protein and solutes, and pH changes due to crystallization of buffer components.

An increase in protein concentration can also enhance the formation of protein aggregates. At high protein concentrations, macromolecular crowding occurs, a term used to describe the effect of high total volume occupancy by macromolecular solutes upon the behavior of each macromolecular species in that solution. According to this excluded volume theory, self-assembly and thus potentially aggregation may be favored.

Antimicrobial preservatives, such as benzyl alcohol and phenol, are often needed in protein liquid formulations to ensure sterility during its shelf life, and in addition required in multidose formulations and certain drug delivery systems, e.g., injection pens, minipumps and topical applications. Many preservatives have been reported to induce protein aggregation, although the underlying mechanism is not well understood. It has been proposed that preservatives bind to and populate unfolded protein states that are prone to aggregation.

Advantageously, the pharmaceutical compositions of the invention are envisaged to be stable, i.e. to remain free or substantially free from protein aggregates even when subjected to stress, in particular thermal stress, storage, surface-induced stress (such as freeze/thaw cycles, foaming), concentration (by ultra- and diafiltration) or being mixed with organic compounds such as antimicrobial preservatives. Preferably, the pharmaceutical compositions may have similar or even improved characteristics as compared to the compositions having a low pH that have been evaluated in the appended Examples. Pharmaceutical compositions of the invention are preferably homogenous solutions of protein-based pharmaceuticals such as dispersed and preferably monomeric bispecific bispecific antibody constructs.

It is envisaged in the context of the present invention to provide a formulation suitable for bispecific (and/or multispecific) antibodies that bind to two (or more) different antigens simultaneously. In certain embodiments the bispecific antibody binds a first target antigen while the second antigen is a cell surface molecule present on an effector cell, i.e., a leukocyte which expresses one or more FcRs (e.g., FcγRIII) and performs one or more effector functions attributable to the Fc region of an antibody. Examples of effector functions include, but are not limited to, C1q binding and complement dependent cytotoxicity (CDC), Fc receptor binding, antibody-dependent cell-mediated cytotoxicity (ADCC), phagocytosis, down regulation of cell surface receptors, and B cell activation. Examples of effector cells involved in ADCC include, but are not limited to, cytotoxic T cells, peripheral blood mononuclear cells (PBMC), natural killer (NK) cells, monocytes, and neutrophils.

The skilled person will appreciate that even though the pharmaceutical composition effectively provides for stabilization of the active ingredient (i.e. reduces or inhibits formation of protein aggregates of the bispecific antibody construct), some aggregates or conformers may occasionally form, however without substantially compromising overall usability of the pharmaceutical composition. In this context "substantially free" of aggregates means that the amount of aggregates remains lower than 10%, 9%, 8%, 7%, 6%, 5%, 4%, 3%, 2% or 1% (w/v), particularly also when being subjected to environmental stress, e.g. as evaluated in the appended Examples.

Methods for determining the presence of soluble and insoluble protein aggregates have been, inter alia, reviewed by Mahler et al., *J Pharm Sci.* 2009 September; 98(9):2909-34. Formation of soluble protein aggregates can be evaluated by size exclusion ultra high performance liquid chromatography (SE-UPLC) as described in the appended Examples. SEC is one of the most used analytical methods for the detection and quantification of protein aggregates. SEC analysis allows both for sizing of aggregates, and their quantification. SEQ-UPLC allows for the selective and rapid separation of macromolecules based on their shape and size (hydrodynamic radius) in a molecular weight range of about 5-1000 kDa.

Protein solutions show an optical property, called opalescence or turbidity. The optical property of a solution is a function of the particles present to scatter and absorb light. Proteins are natural colloids and the turbidity of aqueous formulations depends on protein concentration, the presence of nondissolved particles, particle size and particle number per volume unit. Turbidity can be measured by UV-Vis spectroscopy as optical density in the 340-360 nm range and be used to detect both soluble and insoluble aggregates.

Moreover, the inspection of samples by visual means is still an important aspect of assessing protein aggregates. Visual evaluation for the absence or presence of visible aggregates is preferably performed according to Deutscher Arzneimittel Codex (DAC) Test 5.

As set out elsewhere herein, it is envisaged pharmaceutical composition of the invention—most likely by the action of a low pH and optionally further stabilizing agents comprised therein—favor an increased colloidal stability of the bispecific antibody constructs, and thus exhibit a reduced or even absent liquid-liquid phase separation (LLPS). LLPS is a thermodynamically driven event, in which a homogenous protein solution separates into a protein-poor phase (usually the top layer) and a protein-rich phase (usually the bottom layer) with decreasing temperatures. LLPS is typically fully reversible simply by mixing the two phases and raising the temperature of the solution. The occurrence of LLPS has been attributed to short-range attractive protein-protein interactions—making it a measure of strength of protein-protein attraction. Pharmaceutical compositions comprising β-cyclodextrins according to the invention have been found to comprise higher concentrations of the bispecific antibody construct in the LLPS protein-poor phase, as compared to pharmaceutical compositions not comprising β-cyclodextrins. Accordingly, pharmaceutical compositions of the invention are envisaged to exhibit reduced LLPS or no LLPS at all when compared to controls, and thus promoting an increased colloidal stability of the bispecific antibody constructs of the present invention. LLPS can be induced and the protein content of the different phases can be examined as described in the appended Examples.

Environmental stress can, in particular due to thermal and/or chemical denaturation, also lead to conformational changes, which may in turn favor aggregation. Surprisingly, the present inventors found that bispecific antibody constructs are also stabilized with regard to conformational changes as evaluated by measuring intrinsic fluorescence emission intensity of aromatic amino acids. The pharmaceutical composition of the present invention therefore preferably also reduces or inhibits the formation of conformers (i.e. non-native, abnormally folded protein species).

As explained previously, the stable pharmaceutical composition of the present invention comprises a bispecific antibody construct, binding to a target cell surface antigen via a first binding domain and to the T Cell surface antigen CD3 via a second binding domain.

The term "antibody construct" refers to a molecule in which the structure and/or function is/are based on the structure and/or function of an antibody, e.g., of a full-length or whole immunoglobulin molecule and/or is/are drawn from the variable heavy chain (VH) and/or variable light chain (VL) domains of an antibody or fragment thereof. An antibody construct is hence capable of binding to its specific target or antigen. Furthermore, the binding domain of an antibody construct according to the invention comprises the minimum structural requirements of an antibody which allow for the target binding. This minimum requirement may e.g. be defined by the presence of at least the three light chain CDRs (i.e. CDR1, CDR2 and CDR3 of the VL region) and/or the three heavy chain CDRs (i.e. CDR1, CDR2 and CDR3 of the VH region), preferably of all six CDRs. An alternative approach to define the minimal structure requirements of an antibody is the definition of the epitope of the antibody within the structure of the specific target, respectively, the protein domain of the target protein composing the epitope region (epitope cluster) or by reference to an specific antibody competing with the epitope of the defined antibody. The antibodies on which the constructs according to the invention are based include for example monoclonal, recombinant, chimeric, deimmunized, humanized and human antibodies.

The binding domain of an antibody construct according to the invention may e.g. comprise the above referred groups of CDRs. Preferably, those CDRs are comprised in the framework of an antibody light chain variable region (VL) and an antibody heavy chain variable region (VH); however, it does not have to comprise both. Fd fragments, for example, have two VH regions and often retain some antigen-binding function of the intact antigen-binding domain. Additional examples for the format of antibody fragments, antibody variants or binding domains include (1) a Fab fragment, a monovalent fragment having the VL, VH, CL and CH1 domains; (2) a F(ab')₂ fragment, a bivalent fragment having two Fab fragments linked by a disulfide bridge at the hinge region; (3) an Fd fragment having the two VH and CH1 domains; (4) an Fv fragment having the VL and VH domains of a single arm of an antibody, (5) a dAb fragment (Ward et al., (1989) Nature 341:544-546), which has a VH domain; (6) an isolated complementarity determining region (CDR), and (7) a single chain Fv (scFv), the latter being preferred (for example, derived from an scFV-library). Examples for embodiments of antibody constructs according to the invention are e.g. described in WO 00/006605, WO 2005/040220, WO 2008/119567, WO 2010/037838, WO 2013/026837, WO 2013/026833, US 2014/0308285, US 2014/0302037, WO 2014/144722, WO 2014/151910, and WO 2015/048272.

Alternative bispecific antigen-binding formats are described in, e.g., U.S. Patent Application Publication No. 2011/0054151, incorporated by reference herein. For example, the bispecific antigen-binding protein may comprise a mAb-Fv format, wherein an IgG antibody is fused at the C-terminus with an Fv fragment. Alternatively, a mAb-Fab format may be used wherein an IgG antibody is fused at the C-terminus with a Fab. The mAb-Fab construct contains CH and CL constant domains C-terminal to the C-terminal Fv fusion, whereas mAb-Fv does not. See FIG. 8 of U.S. Patent Application Publication No. 2011/0054151. Optionally, the N-terminal binding region of the mAb-Fv and mAb-Fab constructs lack a light chain and a CH1 domain (i.e., comprise a single domain VHH region). mAb-Fv and mAb-Fab constructs contain three variable regions, such that they bind a first antigen bivalently and a second antigen monovalently. Suitable bispecific antigen-binding formats also include Fab-Fv and Fab-Fab constructs described in U.S. Patent Application Publication No. 2011/0054151. The Fab-Fv and Fab-Fab immunoglobulins comprise an N-terminal Fab fragment that binds a first antigen and a C-terminal Fv or Fab fragment binds a second antigen.

The heterodimeric antibody is preferably of the IgG class, which has several subclasses, including, but not limited to IgG1, IgG2, IgG3, and IgG4, although IgM, IgD, IgG, IgA, and IgE also are contemplated. It should be understood that antibodies can also comprise hybrids of isotypes and/or subclasses. For example, pI engineering of IgG1/G2 hybrids, as shown in U.S. Patent Publication No. 2009/0163699, incorporated by reference, is contemplated as part of the disclosure.

Also within the definition of "binding domain" or "domain which binds" are fragments of full-length antibodies, such as VH, VHH, VL, (s)dAb, Fv, Fd, Fab, Fab', F(ab')2 or "r IgG" ("half antibody"). Antibody constructs according to the invention may also comprise modified fragments of antibodies, also called antibody variants, such as scFv, di-scFv or bi(s)-scFv, scFv-Fc, scFv-zipper, scFab, $Fab_2$, $Fab_3$, diabodies, single chain diabodies, tandem diabodies (Tandab's), tandem di-scFv, tandem tri-scFv, "multibodies" such as triabodies or tetrabodies, and single domain antibodies such as nanobodies or single variable domain antibodies comprising merely one variable domain, which might be VHH, VH or VL, that specifically bind an antigen or epitope independently of other V regions or domains.

As used herein, the terms "single-chain Fv," "single-chain antibodies" or "scFv" refer to single polypeptide chain antibody fragments that comprise the variable regions from both the heavy and light chains, but lack the constant regions. Generally, a single-chain antibody further comprises a polypeptide linker between the VH and VL domains which enables it to form the desired structure which would allow for antigen binding. Single chain antibodies are discussed in detail by Pluckthun in The Pharmacology of Monoclonal Antibodies, vol. 113, Rosenburg and Moore eds. Springer-Verlag, New York, pp. 269-315 (1994). Various methods of generating single chain antibodies are known, including those described in U.S. Pat. Nos. 4,694,778 and 5,260,203; International Patent Application Publication No. WO 88/01649; Bird (1988) Science 242:423-442; Huston et al. (1988) Proc. Natl. Acad. Sci. USA 85:5879-5883; Ward et al. (1989) Nature 334:54454; Skerra et al. (1988) Science 242:1038-1041. In specific embodiments, single-chain antibodies can also be bispecific, multispecific, human, and/or humanized and/or synthetic.

Furthermore, the definition of the term "antibody construct" includes monovalent, bivalent and polyvalent/multivalent constructs and, thus, bispecific constructs, specifically binding to only two antigenic structure, as well as polyspecific/multispecific constructs, which specifically bind more than two antigenic structures, e.g. three, four or more, through distinct binding domains. Moreover, the definition of the term "antibody construct" includes molecules consisting of only one polypeptide chain as well as molecules consisting of more than one polypeptide chain, which chains can be either identical (homodimers, homotrimers or homo oligomers) or different (heterodimer, heterotrimer or heterooligomer). Examples for the above identified antibodies and variants or derivatives thereof are described inter alia in Harlow and Lane, Antibodies a laboratory manual, CSHL Press (1988) and Using Antibodies: a laboratory manual, CSHL Press (1999), Kontermann and Dübel, Antibody Engineering, Springer, 2nd ed. 2010 and Little, Recombinant Antibodies for Immunotherapy, Cambridge University Press 2009.

The term "bispecific" as used herein refers to an antibody construct which is "at least bispecific", i.e., it comprises at least a first binding domain and a second binding domain, wherein the first binding domain binds to one antigen or target (here: the target cell surface antigen), and the second binding domain binds to another antigen or target (e.g. CD3). Accordingly, antibody constructs according to the invention comprise specificities for at least two different antigens or targets. For example, the first domain does preferably not bind to an extracellular epitope of CD3ε of one or more of the species as described herein. The term "target cell surface antigen" refers to an antigenic structure expressed by a cell and which is present at the cell surface such that it is accessible for an antibody construct as described herein. It may be a protein, preferably the extracellular portion of a protein, or a carbohydrate structure, preferably a carbohydrate structure of a protein, such as a glycoprotein. It is preferably a tumor antigen. The term "bispecific antibody construct" of the invention also encompasses multispecific antibody constructs such as trispecific antibody constructs, the latter ones including three binding domains, or constructs having more than three (e.g. four, five . . . ) specificities.

Bispecific antibodies and/or antibody constructs as understood herein include, but are not limited to, traditional bispecific immunoglobulins (e.g., BsIgG), IgG comprising an appended antigen-binding domain (e.g., the amino or carboxy termini of light or heavy chains are connected to additional antigen-binding domains, such as single domain antibodies or paired antibody variable domains (e.g., Fv or scFv)), BsAb fragments (e.g., bispecific single chain antibodies), bispecific fusion proteins (e.g., antigen binding domains fused to an effector moiety), and BsAb conjugates. See, e.g., Spiess et al., Molecular Immunology 67(2) Part A: 97-106 (2015), which describes various bispecific formats and is hereby incorporated by reference. Examples of bispecific constructs include, but are not limited to, diabodies, single chain diabodies, tandem scFvs, bispecific T cell engager (BiTE) format (a fusion protein consisting of two single-chain variable fragments (scFvs) joined by a linker), and Fab2 bispecifics, as well as engineered constructs comprising full length antibodies. See, e.g., Chames & Baty, 2009, mAbs 1[6]:1-9; and Holliger & Hudson, 2005, Nature Biotechnology 23[9]:1126-1136; Wu et al., 2007, Nature Biotechnology 25[11]:1290-1297; Michaelson et al., 2009, mAbs 1[2]:128-141; International Patent Publication No. 2009032782 and 2006020258; Zuo et al., 2000, Protein Engineering 13[5]:361-367; U.S. Patent Application Publication No. 20020103345; Shen et al., 2006, J Biol Chem 281[16]:10706-10714; Lu et al., 2005, J Biol Chem 280[20]: 19665-19672; and Kontermann, 2012 MAbs 4(2):182, all of which are expressly incorporated herein.

Given that the antibody constructs according to the invention are (at least) bispecific, they do not occur naturally and they are markedly different from naturally occurring products. A "bispecific" antibody construct or immunoglobulin is hence an artificial hybrid antibody or immunoglobulin having at least two distinct binding sides with different specificities. Bispecific antibody constructs can be produced by a variety of methods including fusion of hybridomas or linking of Fab' fragments. See, e.g., Songsivilai & Lachmann, Clin. Exp. Immunol. 79:315-321 (1990).

The at least two binding domains and the variable domains (VH/VL) of the antibody construct of the present invention may or may not comprise peptide linkers (spacer peptides). The term "peptide linker" comprises in accordance with the present invention an amino acid sequence by which the amino acid sequences of one (variable and/or binding) domain and another (variable and/or binding) domain of the antibody construct of the invention are linked with each other. The peptide linkers can also be used to fuse the third domain to the other domains of the antibody construct of the invention. An essential technical feature of such peptide linker is that it does not comprise any polymerization activity. Among the suitable peptide linkers are those described in U.S. Pat. Nos. 4,751,180 and 4,935,233 or WO 88/09344. The peptide linkers can also be used to attach other domains or modules or regions (such as half-life extending domains) to the antibody construct of the invention.

The antibody constructs of the present invention are preferably "in vitro generated antibody constructs". This term refers to an antibody construct according to the above definition where all or part of the variable region (e.g., at least one CDR) is generated in a non-immune cell selection, e.g., an in vitro phage display, protein chip or any other method in which candidate sequences can be tested for their ability to bind to an antigen. This term thus preferably excludes sequences generated solely by genomic rearrangement in an immune cell in an animal. A "recombinant antibody" is an antibody made through the use of recombinant DNA technology or genetic engineering.

The term "monoclonal antibody" (mAb) or monoclonal antibody construct as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. Monoclonal antibodies are highly specific, being directed against a single antigenic side or determinant on the antigen, in contrast to conventional (polyclonal) antibody preparations which typically include different antibodies directed against different determinants (or epitopes). In addition to their specificity, the monoclonal antibodies are advantageous in that they are synthesized by the hybridoma culture, hence uncontaminated by other immunoglobulins. The modifier "monoclonal" indicates the character of the antibody as being obtained from a substantially homogeneous population of antibodies, and is not to be construed as requiring production of the antibody by any particular method.

For the preparation of monoclonal antibodies, any technique providing antibodies produced by continuous cell line cultures can be used. For example, monoclonal antibodies to be used may be made by the hybridoma method first described by Koehler et al., Nature, 256: 495 (1975), or may be made by recombinant DNA methods (see, e.g., U.S. Pat. No. 4,816,567). Examples for further techniques to produce human monoclonal antibodies include the trioma technique, the human B-cell hybridoma technique (Kozbor, Immunology Today 4 (1983), 72) and the EBV-hybridoma technique (Cole et al., Monoclonal Antibodies and Cancer Therapy, Alan R. Liss, Inc. (1985), 77-96).

Hybridomas can then be screened using standard methods, such as enzyme-linked immunosorbent assay (ELISA) and surface plasmon resonance (BIACORE™) analysis, to identify one or more hybridomas that produce an antibody that specifically binds with a specified antigen. Any form of the relevant antigen may be used as the immunogen, e.g., recombinant antigen, naturally occurring forms, any variants or fragments thereof, as well as an antigenic peptide thereof. Surface plasmon resonance as employed in the BIACore™ system can be used to increase the efficiency of phage antibodies which bind to an epitope of a target cell surface antigen, (Schier, Human Antibodies Hybridomas 7 (1996), 97-105; Malmborg, J. Immunol. Methods 183 (1995), 7-13).

Another exemplary method of making monoclonal antibodies includes screening protein expression libraries, e.g., phage display or ribosome display libraries. Phage display is described, for example, in Ladner et al., U.S. Pat. No. 5,223,409; Smith (1985) Science 228:1315-1317, Clackson et al., Nature, 352: 624-628 (1991) and Marks et al., J. Mol. Biol., 222: 581-597 (1991).

In addition to the use of display libraries, the relevant antigen can be used to immunize a non-human animal, e.g., a rodent (such as a mouse, hamster, rabbit or rat). In one embodiment, the non-human animal includes at least a part of a human immunoglobulin gene. For example, it is possible to engineer mouse strains deficient in mouse antibody production with large fragments of the human Ig (immunoglobulin) loci. Using the hybridoma technology, antigen-specific monoclonal antibodies derived from the genes with the desired specificity may be produced and selected. See, e.g., XENOMOUSE™, Green et al. (1994) Nature Genetics 7:13-21, US 2003-0070185, WO 96/34096, and WO 96/33735.

A monoclonal antibody can also be obtained from a non-human animal, and then modified, e.g., humanized, deimmunized, rendered chimeric etc., using recombinant DNA techniques known in the art. Examples of modified antibody constructs include humanized variants of non-human antibodies, "affinity matured" antibodies (see, e.g. Hawkins et al. J. Mol. Biol. 254, 889-896 (1992) and Lowman et al., Biochemistry 30, 10832-10837 (1991)) and antibody mutants with altered effector function(s) (see, e.g., U.S. Pat. No. 5,648,260, Kontermann and Dübel (2010), loc. cit. and Little (2009), loc. cit.).

In immunology, affinity maturation is the process by which B cells produce antibodies with increased affinity for antigen during the course of an immune response. With repeated exposures to the same antigen, a host will produce antibodies of successively greater affinities. Like the natural prototype, the in vitro affinity maturation is based on the principles of mutation and selection. The in vitro affinity maturation has successfully been used to optimize antibodies, antibody constructs, and antibody fragments. Random mutations inside the CDRs are introduced using radiation, chemical mutagens or error-prone PCR. In addition, the genetic diversity can be increased by chain shuffling. Two or three rounds of mutation and selection using display methods like phage display usually results in antibody fragments with affinities in the low nanomolar range.

A preferred type of an amino acid substitutional variation of the antibody constructs involves substituting one or more hypervariable region residues of a parent antibody (e. g. a humanized or human antibody). Generally, the resulting variant(s) selected for further development will have improved biological properties relative to the parent antibody from which they are generated. A convenient way for generating such substitutional variants involves affinity maturation using phage display. Briefly, several hypervariable region sides (e. g. 6-7 sides) are mutated to generate all possible amino acid substitutions at each side. The antibody variants thus generated are displayed in a monovalent fashion from filamentous phage particles as fusions to the gene III product of M13 packaged within each particle. The phage-displayed variants are then screened for their biological activity (e. g. binding affinity) as herein disclosed. In order to identify candidate hypervariable region sides for modification, alanine scanning mutagenesis can be performed to identify hypervariable region residues contributing significantly to antigen binding. Alternatively, or additionally, it may be beneficial to analyze a crystal structure of the antigen-antibody complex to identify contact points between the binding domain and, e.g., human target cell surface antigen. Such contact residues and neighboring residues are candidates for substitution according to the techniques elaborated herein. Once such variants are generated, the panel of variants is subjected to screening as described herein and antibodies with superior properties in one or more relevant assays may be selected for further development.

The monoclonal antibodies and antibody constructs of the present invention specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is/are identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., Proc. Natl. Acad. Sci. USA, 81: 6851-6855 (1984)). Chimeric antibodies of interest herein include "primitized" antibodies comprising variable domain antigen-binding sequences derived from a non-human primate (e.g., Old World Monkey, Ape etc.) and human constant region sequences. A variety of approaches for making chimeric antibodies have been described. See e.g., Morrison et al., Proc. Natl. Acad. Sci U.S.A. 81:6851, 1985; Takeda et al., Nature 314:452, 1985, Cabilly et al., U.S. Pat. No. 4,816,567; Boss et al., U.S. Pat. No. 4,816,397; Tanaguchi et al., EP 0171496; EP 0173494; and GB 2177096.

An antibody, antibody construct, antibody fragment or antibody variant may also be modified by specific deletion of human T cell epitopes (a method called "deimmunization") by the methods disclosed for example in WO 98/52976 or WO 00/34317. Briefly, the heavy and light chain variable domains of an antibody can be analyzed for peptides that bind to MHC class II; these peptides represent potential T cell epitopes (as defined in WO 98/52976 and WO 00/34317). For detection of potential T cell epitopes, a computer modeling approach termed "peptide threading" can be applied, and in addition a database of human MHC class II binding peptides can be searched for motifs present in the VH and VL sequences, as described in WO 98/52976 and WO 00/34317. These motifs bind to any of the 18 major MHC class II DR allotypes, and thus constitute potential T cell epitopes. Potential T cell epitopes detected can be eliminated by substituting small numbers of amino acid residues in the variable domains, or preferably, by single amino acid substitutions. Typically, conservative substitutions are made. Often, but not exclusively, an amino acid common to a position in human germline antibody sequences may be used. Human germline sequences are disclosed e.g. in Tomlinson, et al. (1992) J. Mol. Biol. 227:776-798; Cook, G. P. et al. (1995) Immunol. Today Vol. 16 (5): 237-242; and Tomlinson et al. (1995) EMBO J. 14: 14:4628-4638. The V BASE directory provides a comprehensive directory of human immunoglobulin variable region sequences (compiled by Tomlinson, I.A. et al. MRC Centre for Protein Engineering, Cambridge, UK). These sequences can be used as a source of human sequence, e.g., for framework regions and CDRs. Consensus human framework regions can also be used, for example as described in U.S. Pat. No. 6,300,064.

"Humanized" antibodies, antibody constructs, variants or fragments thereof (such as Fv, Fab, Fab', F(ab')2 or other antigen-binding subsequences of antibodies) are antibodies or immunoglobulins of mostly human sequences, which contain (a) minimal sequence(s) derived from non-human immunoglobulin. For the most part, humanized antibodies are human immunoglobulins (recipient antibody) in which residues from a hypervariable region (also CDR) of the recipient are replaced by residues from a hypervariable region of a non-human (e.g., rodent) species (donor antibody) such as mouse, rat, hamster or rabbit having the desired specificity, affinity, and capacity. In some instances, Fv framework region (FR) residues of the human immunoglobulin are replaced by corresponding non-human residues. Furthermore, "humanized antibodies" as used herein may also comprise residues which are found neither in the recipient antibody nor the donor antibody. These modifications are made to further refine and optimize antibody performance. The humanized antibody may also comprise at least a portion of an immunoglobulin constant region (Fc), typically that of a human immunoglobulin. For further details, see Jones et al., Nature, 321: 522-525 (1986); Reichmann et al., Nature, 332: 323-329 (1988); and Presta, Curr. Op. Struct. Biol., 2: 593-596 (1992).

Humanized antibodies or fragments thereof can be generated by replacing sequences of the Fv variable domain that are not directly involved in antigen binding with equivalent sequences from human Fv variable domains. Exemplary methods for generating humanized antibodies or fragments thereof are provided by Morrison (1985) Science 229:1202-1207; by Oi et al. (1986) BioTechniques 4:214; and by U.S. Pat. Nos. 5,585,089; 5,693,761; 5,693,762; 5,859,205; and 6,407,213. Those methods include isolating, manipulating, and expressing the nucleic acid sequences that encode all or part of immunoglobulin Fv variable domains from at least one of a heavy or light chain. Such nucleic acids may be obtained from a hybridoma producing an antibody against a predetermined target, as described above, as well as from other sources. The recombinant DNA encoding the humanized antibody molecule can then be cloned into an appropriate expression vector.

Humanized antibodies may also be produced using transgenic animals such as mice that express human heavy and light chain genes, but are incapable of expressing the endogenous mouse immunoglobulin heavy and light chain genes. Winter describes an exemplary CDR grafting method that may be used to prepare the humanized antibodies described herein (U.S. Pat. No. 5,225,539). All of the CDRs of a particular human antibody may be replaced with at least a portion of a non-human CDR, or only some of the CDRs may be replaced with non-human CDRs. It is only necessary to replace the number of CDRs required for binding of the humanized antibody to a predetermined antigen.

A humanized antibody can be optimized by the introduction of conservative substitutions, consensus sequence substitutions, germline substitutions and/or back mutations. Such altered immunoglobulin molecules can be made by any of several techniques known in the art, (e.g., Teng et al., Proc. Natl. Acad. Sci. U.S.A., 80: 7308-7312, 1983; Kozbor et al., Immunology Today, 4: 7279, 1983; Olsson et al., Meth. Enzymol., 92: 3-16, 1982, and EP 239 400).

The term "human antibody", "human antibody construct" and "human binding domain" includes antibodies, antibody constructs and binding domains having antibody regions such as variable and constant regions or domains which correspond substantially to human germline immunoglobulin sequences known in the art, including, for example, those described by Kabat et al. (1991) (loc. cit.). The human antibodies, antibody constructs or binding domains of the invention may include amino acid residues not encoded by human germline immunoglobulin sequences (e.g., mutations introduced by random or side-specific mutagenesis in vitro or by somatic mutation in vivo), for example in the CDRs, and in particular, in CDR3. The human antibodies, antibody constructs or binding domains can have at least one, two, three, four, five, or more positions replaced with an amino acid residue that is not encoded by the human germline immunoglobulin sequence. The definition of human antibodies, antibody constructs and binding domains as used herein, however, also contemplates "fully human antibodies", which include only non-artificially and/or genetically altered human sequences of antibodies as those can be derived by using technologies or systems such as the Xenomouse. Preferably, a "fully human antibody" does not include amino acid residues not encoded by human germline immunoglobulin sequences.

In some embodiments, the antibody constructs of the invention are "isolated" or "substantially pure" antibody constructs. "Isolated" or "substantially pure", when used to describe the antibody constructs disclosed herein, means an antibody construct that has been identified, separated and/or recovered from a component of its production environment. Preferably, the antibody construct is free or substantially free of association with all other components from its production environment. Contaminant components of its production environment, such as that resulting from recombinant transfected cells, are materials that would typically interfere with diagnostic or therapeutic uses for the polypeptide, and may include enzymes, hormones, and other proteinaceous or non-proteinaceous solutes. The antibody constructs may e.g constitute at least about 5%, or at least about 50% by weight of the total protein in a given sample. It is understood that the isolated protein may constitute from 5% to 99.9% by weight of the total protein content, depending on the circumstances. The polypeptide may be made at a significantly higher concentration through the use of an inducible promoter or high expression promoter, such that it is made at increased concentration levels. The definition includes the production of an antibody construct in a wide variety of organisms and/or host cells that are known in the art. In preferred embodiments, the antibody construct will be purified (1) to a degree sufficient to obtain at least 15 residues of N-terminal or internal amino acid sequence by use of a spinning cup sequenator, or (2) to homogeneity by SDS-PAGE under non-reducing or reducing conditions using Coomassie blue or, preferably, silver stain. Ordinarily, however, an isolated antibody construct will be prepared by at least one purification step.

The term "binding domain" characterizes in connection with the present invention a domain which (specifically) binds to/interacts with/recognizes a given target epitope or a given target side on the target molecules (antigens), e.g. CD33 and CD3, respectively. The structure and function of the first binding domain (recognizing e.g. CD33), and preferably also the structure and/or function of the second binding domain (recognizing CD3), is/are based on the structure and/or function of an antibody, e.g. of a full-length or whole immunoglobulin molecule and/or is/are drawn from the variable heavy chain (VH) and/or variable light chain (VL) domains of an antibody or fragment thereof. Preferably the first binding domain is characterized by the presence of three light chain CDRs (i.e. CDR1, CDR2 and CDR3 of the VL region) and/or three heavy chain CDRs (i.e. CDR1, CDR2 and CDR3 of the VH region). The second binding domain preferably also comprises the minimum structural requirements of an antibody which allow for the target binding. More preferably, the second binding domain comprises at least three light chain CDRs (i.e. CDR1, CDR2 and CDR3 of the VL region) and/or three heavy chain CDRs (i.e. CDR1, CDR2 and CDR3 of the VH region). It is envisaged that the first and/or second binding domain is produced by or obtainable by phage-display or library screening methods rather than by grafting CDR sequences from a pre-existing (monoclonal) antibody into a scaffold.

According to the present invention, binding domains are in the form of one or more polypeptides. Such polypeptides may include proteinaceous parts and non-proteinaceous parts (e.g. chemical linkers or chemical cross-linking agents such as glutaraldehyde). Proteins (including fragments thereof, preferably biologically active fragments, and peptides, usually having less than 30 amino acids) comprise two or more amino acids coupled to each other via a covalent peptide bond (resulting in a chain of amino acids).

The term "polypeptide" as used herein describes a group of molecules, which usually consist of more than 30 amino acids. Polypeptides may further form multimers such as dimers, trimers and higher oligomers, i.e., consisting of more than one polypeptide molecule. Polypeptide molecules forming such dimers, trimers etc. may be identical or non-identical. The corresponding higher order structures of such multimers are, consequently, termed homo- or heterodimers, homo- or heterotrimers etc. An example for a heteromultimer is an antibody molecule, which, in its naturally occurring form, consists of two identical light polypeptide chains and two identical heavy polypeptide chains. The terms "peptide", "polypeptide" and "protein" also refer to naturally modified peptides/polypeptides/proteins wherein the modification is effected e.g. by post-translational modifications like glycosylation, acetylation, phosphorylation and the like. A "peptide", "polypeptide" or "protein" when referred to herein may also be chemically modified such as pegylated. Such modifications are well known in the art and described herein below.

Preferably the binding domain which binds to the target cell surface antigen and/or the binding domain which binds to CD3ε is/are human binding domains. Antibodies and antibody constructs comprising at least one human binding domain avoid some of the problems associated with antibodies or antibody constructs that possess non-human such as rodent (e.g. murine, rat, hamster or rabbit) variable and/or constant regions. The presence of such rodent derived proteins can lead to the rapid clearance of the antibodies or antibody constructs or can lead to the generation of an immune response against the antibody or antibody construct by a patient. In order to avoid the use of rodent derived antibodies or antibody constructs, human or fully human antibodies/antibody constructs can be generated through the introduction of human antibody function into a rodent so that the rodent produces fully human antibodies.

The ability to clone and reconstruct megabase-sized human loci in YACs and to introduce them into the mouse germline provides a powerful approach to elucidating the functional components of very large or crudely mapped loci as well as generating useful models of human disease. Furthermore, the use of such technology for substitution of mouse loci with their human equivalents could provide unique insights into the expression and regulation of human gene products during development, their communication with other systems, and their involvement in disease induction and progression.

An important practical application of such a strategy is the "humanization" of the mouse humoral immune system. Introduction of human immunoglobulin (Ig) loci into mice in which the endogenous Ig genes have been inactivated offers the opportunity to study the mechanisms underlying programmed expression and assembly of antibodies as well as their role in B-cell development. Furthermore, such a strategy could provide an ideal source for production of fully human monoclonal antibodies (mAbs)—an important milestone towards fulfilling the promise of antibody therapy in human disease. Fully human antibodies or antibody constructs are expected to minimize the immunogenic and allergic responses intrinsic to mouse or mouse-derivatized mAbs and thus to increase the efficacy and safety of the administered antibodies/antibody constructs. The use of fully human antibodies or antibody constructs can be expected to provide a substantial advantage in the treatment of chronic and recurring human diseases, such as inflammation, autoimmunity, and cancer, which require repeated compound administrations.

One approach towards this goal was to engineer mouse strains deficient in mouse antibody production with large fragments of the human Ig loci in anticipation that such mice would produce a large repertoire of human antibodies in the absence of mouse antibodies. Large human Ig fragments would preserve the large variable gene diversity as well as the proper regulation of antibody production and expression. By exploiting the mouse machinery for antibody diversification and selection and the lack of immunological tolerance to human proteins, the reproduced human antibody repertoire in these mouse strains should yield high affinity antibodies against any antigen of interest, including human antigens. Using the hybridoma technology, antigen-specific human mAbs with the desired specificity could be readily produced and selected. This general strategy was demonstrated in connection with the generation of the first Xeno-Mouse mouse strains (see Green et al. Nature Genetics 7:13-21 (1994)). The XenoMouse strains were engineered with yeast artificial chromosomes (YACs) containing 245 kb and 190 kb-sized germline configuration fragments of the human heavy chain locus and kappa light chain locus, respectively, which contained core variable and constant region sequences. The human Ig containing YACs proved to be compatible with the mouse system for both rearrangement and expression of antibodies and were capable of substituting for the inactivated mouse Ig genes. This was demonstrated by their ability to induce B cell development, to produce an adult-like human repertoire of fully human antibodies, and to generate antigen-specific human mAbs. These results also suggested that introduction of larger portions of the human Ig loci containing greater numbers of V genes, additional regulatory elements, and human Ig constant regions might recapitulate substantially the full repertoire that is characteristic of the human humoral response to infection and immunization. The work of Green et al. was recently extended to the introduction of greater than approximately 80% of the human antibody repertoire through introduction of megabase sized, germline configuration YAC fragments of the human heavy chain loci and kappa light chain loci, respectively. See Mendez et al. Nature Genetics 15:146-156 (1997) and U.S. patent application Ser. No. 08/759,620.

The production of the XenoMouse mice is further discussed and delineated in U.S. patent application Ser. Nos. 07/466,008, 07/610,515, 07/919,297, 07/922,649, 08/031, 801, 08/112,848, 08/234,145, 08/376,279, 08/430,938, 08/464,584, 08/464,582, 08/463,191, 08/462,837, 08/486, 853, 08/486,857, 08/486,859, 08/462,513, 08/724,752, and 08/759,620; and U.S. Pat. Nos. 6,162,963; 6,150,584; 6,114, 598; 6,075,181, and 5,939,598 and Japanese Patent Nos. 3 068 180 B2, 3 068 506 B2, and 3 068 507 B2. See also Mendez et al. Nature Genetics 15:146-156 (1997) and Green and Jakobovits J. Exp. Med. 188:483-495 (1998), EP 0 463 151 B1, WO 94/02602, WO 96/34096, WO 98/24893, WO 00/76310, and WO 03/47336.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more VH genes, one or more DH genes, one or more JH genes, a mu constant region, and a second constant region (preferably a gamma constant region) are formed into a construct for insertion into an animal. This approach is described in U.S. Pat. No. 5,545, 807 to Surani et al. and U.S. Pat. Nos. 5,545,806; 5,625,825; 5,625,126; 5,633,425; 5,661,016; 5,770,429; 5,789,650; 5,814,318; 5,877,397; 5,874,299; and 6,255,458 each to Lonberg and Kay, U.S. Pat. Nos. 5,591,669 and 6,023,010 to Krimpenfort and Berns, U.S. Pat. Nos. 5,612,205; 5,721, 367; and U.S. Pat. No. 5,789,215 to Berns et al., and U.S. Pat. No. 5,643,763 to Choi and Dunn, and GenPharm International U.S. patent application Ser. Nos. 07/574,748, 07/575,962, 07/810,279, 07/853,408, 07/904,068, 07/990, 860, 08/053,131, 08/096,762, 08/155,301, 08/161,739, 08/165,699, 08/209,741. See also EP 0 546 073 B1, WO 92/03918, WO 92/22645, WO 92/22647, WO 92/22670, WO 93/12227, WO 94/00569, WO 94/25585, WO 96/14436, WO 97/13852, and WO 98/24884 and U.S. Pat. No. 5,981,175. See further Taylor et al. (1992), Chen et al. (1993), Tuaillon et al. (1993), Choi et al. (1993), Lonberg et al. (1994), Taylor et al. (1994), and Tuaillon et al. (1995), Fishwild et al. (1996).

Kirin has also demonstrated the generation of human antibodies from mice in which, through microcell fusion, large pieces of chromosomes, or entire chromosomes, have been introduced. See European Patent Application Nos. 773 288 and 843 961. Xenerex Biosciences is developing a technology for the potential generation of human antibodies. In this technology, SCID mice are reconstituted with human lymphatic cells, e.g., B and/or T cells. Mice are then immunized with an antigen and can generate an immune response against the antigen. See U.S. Pat. Nos. 5,476,996; 5,698,767; and 5,958,765.

Human anti-mouse antibody (HAMA) responses have led the industry to prepare chimeric or otherwise humanized antibodies. It is however expected that certain human anti-chimeric antibody (HACA) responses will be observed, particularly in chronic or multi-dose utilizations of the antibody. Thus, it would be desirable to provide antibody constructs comprising a human binding domain against the target cell surface antigen and a human binding domain against CD3ε in order to vitiate concerns and/or effects of HAMA or HACA response.

The terms "(specifically) binds to", (specifically) recognizes", "is (specifically) directed to", and "(specifically) reacts with" mean in accordance with this invention that a binding domain interacts or specifically interacts with a given epitope or a given target side on the target molecules (antigens), here: target cell surface antigen and CD3ε, respectively.

The term "epitope" refers to a side on an antigen to which a binding domain, such as an antibody or immunoglobulin, or a derivative, fragment or variant of an antibody or an immunoglobulin, specifically binds. An "epitope" is antigenic and thus the term epitope is sometimes also referred to herein as "antigenic structure" or "antigenic determinant". Thus, the binding domain is an "antigen interaction side". Said binding/interaction is also understood to define a "specific recognition".

"Epitopes" can be formed both by contiguous amino acids or non-contiguous amino acids juxtaposed by tertiary folding of a protein. A "linear epitope" is an epitope where an amino acid primary sequence comprises the recognized epitope. A linear epitope typically includes at least 3 or at least 4, and more usually, at least 5 or at least 6 or at least 7, for example, about 8 to about 10 amino acids in a unique sequence.

A "conformational epitope", in contrast to a linear epitope, is an epitope wherein the primary sequence of the amino acids comprising the epitope is not the sole defining component of the epitope recognized (e.g., an epitope wherein the primary sequence of amino acids is not necessarily recognized by the binding domain). Typically a conformational epitope comprises an increased number of amino acids relative to a linear epitope. With regard to recognition of conformational epitopes, the binding domain recognizes a three-dimensional structure of the antigen, preferably a peptide or protein or fragment thereof (in the context of the present invention, the antigenic structure for one of the binding domains is comprised within the target cell surface antigen protein). For example, when a protein molecule folds to form a three-dimensional structure, certain amino acids and/or the polypeptide backbone forming the conformational epitope become juxtaposed enabling the antibody to recognize the epitope. Methods of determining the conformation of epitopes include, but are not limited to, x-ray crystallography, two-dimensional nuclear magnetic resonance (2D-NMR) spectroscopy and site-directed spin labelling and electron paramagnetic resonance (EPR) spectroscopy.

A method for epitope mapping is described in the following: When a region (a contiguous amino acid stretch) in the human target cell surface antigen protein is exchanged/replaced with its corresponding region of a non-human and non-primate target cell surface antigen (e.g., mouse target cell surface antigen, but others like chicken, rat, hamster, rabbit etc. might also be conceivable), a decrease in the binding of the binding domain is expected to occur, unless the binding domain is cross-reactive for the non-human, non-primate target cell surface antigen used. Said decrease is preferably at least 10%, 20%, 30%, 40%, or 50%; more preferably at least 60%, 70%, or 80%, and most preferably 90%, 95% or even 100% in comparison to the binding to the respective region in the human target cell surface antigen protein, whereby binding to the respective region in the human target cell surface antigen protein is set to be 100%. It is envisaged that the aforementioned human target cell surface antigen/non-human target cell surface antigen chimeras are expressed in CHO cells. It is also envisaged that the human target cell surface antigen/non-human target cell surface antigen chimeras are fused with a transmembrane domain and/or cytoplasmic domain of a different membrane-bound protein such as EpCAM.

In an alternative or additional method for epitope mapping, several truncated versions of the human target cell surface antigen extracellular domain can be generated in order to determine a specific region that is recognized by a binding domain. In these truncated versions, the different extracellular target cell surface antigen domains/sub-domains or regions are stepwise deleted, starting from the N-terminus. It is envisaged that the truncated target cell surface antigen versions may be expressed in CHO cells. It is also envisaged that the truncated target cell surface antigen versions may be fused with a transmembrane domain and/or cytoplasmic domain of a different membrane-bound protein such as EpCAM. It is also envisaged that the truncated target cell surface antigen versions may encompass a signal peptide domain at their N-terminus, for example a signal peptide derived from mouse IgG heavy chain signal peptide. It is furthermore envisaged that the truncated target cell surface antigen versions may encompass a v5 domain at their N-terminus (following the signal peptide) which allows verifying their correct expression on the cell surface. A decrease or a loss of binding is expected to occur with those truncated target cell surface antigen versions which do not encompass any more the target cell surface antigen region that is recognized by the binding domain. The decrease of binding is preferably at least 10%, 20%, 30%, 40%, 50%; more preferably at least 60%, 70%, 80%, and most preferably 90%, 95% or even 100%, whereby binding to the entire human target cell surface antigen protein (or its extracellular region or domain) is set to be 100.

A further method to determine the contribution of a specific residue of a target cell surface antigen to the recognition by an antibody construct or binding domain is alanine scanning (see e.g. Morrison K L & Weiss G A. Cur Opin Chem Biol. 2001 June; 5(3):302-7), where each residue to be analyzed is replaced by alanine, e.g. via site-directed mutagenesis. Alanine is used because of its non-bulky, chemically inert, methyl functional group that nevertheless mimics the secondary structure references that many of the other amino acids possess. Sometimes bulky amino acids such as valine or leucine can be used in cases where conservation of the size of mutated residues is desired. Alanine scanning is a mature technology which has been used for a long period of time.

The interaction between the binding domain and the epitope or the region comprising the epitope implies that a binding domain exhibits appreciable affinity for the epitope/the region comprising the epitope on a particular protein or antigen (here: target cell surface antigen and CD3, respectively) and, generally, does not exhibit significant reactivity with proteins or antigens other than the target cell surface antigen or CD3. "Appreciable affinity" includes binding with an affinity of about $10^{-6}$ M (KD) or stronger. Preferably, binding is considered specific when the binding affinity is about $10^{-12}$ to $10^{-8}$ M, $10^{-12}$ to $10^{-9}$ M, $10^{-12}$ to $10^{-10}$ M, $10^{-11}$ to $10^{-8}$ M, preferably of about $10^{-11}$ to $10^{-9}$ M. Whether a binding domain specifically reacts with or binds to a target can be tested readily by, inter alia, comparing the reaction of said binding domain with a target protein or antigen with the reaction of said binding domain with proteins or antigens other than the target cell surface antigen or CD3. Preferably, a binding domain of the invention does not essentially or substantially bind to proteins or antigens other than the target cell surface antigen or CD3 (i.e., the first binding domain is not capable of binding to proteins other than the target cell surface antigen and the second binding domain is not capable of binding to proteins other than CD3). It is an envisaged characteristic of the antibody constructs according to the present invention to have superior affinity characteristics in comparison to other HLE formats. Such a superior affinity, in consequence, suggests a prolonged half-life in vivo. The longer half-life of the antibody constructs according to the present invention may reduce the duration and frequency of administration which typically contributes to improved patient compliance. This is of particular importance as the antibody constructs of the present invention are particularly beneficial for highly weakened or even multimorbide cancer patients.

The term "does not essentially/substantially bind" or "is not capable of binding" means that a binding domain of the present invention does not bind a protein or antigen other than the target cell surface antigen or CD3, i.e., does not show reactivity of more than 30%, preferably not more than 20%, more preferably not more than 10%, particularly preferably not more than 9%, 8%, 7%, 6% or 5% with proteins or antigens other than the target cell surface antigen or CD3, whereby binding to the target cell surface antigen or CD3, respectively, is set to be 100%.

Specific binding is believed to be effected by specific motifs in the amino acid sequence of the binding domain and the antigen. Thus, binding is achieved as a result of their primary, secondary and/or tertiary structure as well as the result of secondary modifications of said structures. The specific interaction of the antigen-interaction-side with its specific antigen may result in a simple binding of said side to the antigen. Moreover, the specific interaction of the antigen-interaction-side with its specific antigen may alternatively or additionally result in the initiation of a signal, e.g. due to the induction of a change of the conformation of the antigen, an oligomerization of the antigen, etc.

The term "variable" refers to the portions of the antibody or immunoglobulin domains that exhibit variability in their sequence and that are involved in determining the specificity and binding affinity of a particular antibody (i.e., the "variable domain(s)"). The pairing of a variable heavy chain (VH) and a variable light chain (VL) together forms a single antigen-binding side.

Variability is not evenly distributed throughout the variable domains of antibodies; it is concentrated in sub-domains of each of the heavy and light chain variable regions. These sub-domains are called "hypervariable regions" or "complementarity determining regions" (CDRs). The more conserved (i.e., non-hypervariable) portions of the variable domains are called the "framework" regions (FRM or FR) and provide a scaffold for the six CDRs in three dimensional space to form an antigen-binding surface. The variable domains of naturally occurring heavy and light chains each comprise four FRM regions (FR1, FR2, FR3, and FR4), largely adopting a β-sheet configuration, connected by three hypervariable regions, which form loops connecting, and in some cases forming part of, the β-sheet structure. The hypervariable regions in each chain are held together in close proximity by the FRM and, with the hypervariable regions from the other chain, contribute to the formation of the antigen-binding side (see Kabat et al., loc. cit.).

The terms "CDR", and its plural "CDRs", refer to the complementarity determining region of which three make up the binding character of a light chain variable region (CDR-L1, CDR-L2 and CDR-L3) and three make up the binding character of a heavy chain variable region (CDR-H1, CDR-H2 and CDR-H3). CDRs contain most of the residues responsible for specific interactions of the antibody with the antigen and hence contribute to the functional activity of an antibody molecule: they are the main determinants of antigen specificity.

The exact definitional CDR boundaries and lengths are subject to different classification and numbering systems. CDRs may therefore be referred to by Kabat, Chothia, contact or any other boundary definitions, including the numbering system described herein. Despite differing boundaries, each of these systems has some degree of overlap in what constitutes the so called "hypervariable regions" within the variable sequences. CDR definitions according to these systems may therefore differ in length and boundary areas with respect to the adjacent framework region. See for example Kabat (an approach based on cross-species sequence variability), Chothia (an approach based on crystallographic studies of antigen-antibody complexes), and/or MacCallum (Kabat et al., loc. cit.; Chothia et al., J. Mol. Biol, 1987, 196: 901-917; and MacCallum et al., J. Mol. Biol, 1996, 262: 732). Still another standard for characterizing the antigen binding side is the AbM definition used by Oxford Molecular's AbM antibody modeling software. See, e.g., Protein Sequence and Structure Analysis of Antibody Variable Domains. In: Antibody Engineering Lab Manual (Ed.: Duebel, S. and Kontermann, R., Springer-Verlag, Heidelberg). To the extent that two residue identification techniques define regions of overlapping, but not identical regions, they can be combined to define a hybrid CDR. However, the numbering in accordance with the so-called Kabat system is preferred.

Typically, CDRs form a loop structure that can be classified as a canonical structure. The term "canonical structure" refers to the main chain conformation that is adopted by the antigen binding (CDR) loops. From comparative structural studies, it has been found that five of the six antigen binding loops have only a limited repertoire of available conformations. Each canonical structure can be characterized by the torsion angles of the polypeptide backbone. Correspondent loops between antibodies may, therefore, have very similar three dimensional structures, despite high amino acid sequence variability in most parts of the loops (Chothia and Lesk, J. Mol. Biol., 1987, 196: 901; Chothia et al., Nature, 1989, 342: 877; Martin and Thornton, J. Mol. Biol, 1996, 263: 800). Furthermore, there is a relationship between the adopted loop structure and the amino acid sequences surrounding it. The conformation of a particular canonical class is determined by the length of the loop and the amino acid residues residing at key positions within the loop, as well as within the conserved framework (i.e., outside of the loop). Assignment to a particular canonical class can therefore be made based on the presence of these key amino acid residues.

The term "canonical structure" may also include considerations as to the linear sequence of the antibody, for example, as catalogued by Kabat (Kabat et al., loc. cit.). The Kabat numbering scheme (system) is a widely adopted standard for numbering the amino acid residues of an antibody variable domain in a consistent manner and is the preferred scheme applied in the present invention as also mentioned elsewhere herein. Additional structural considerations can also be used to determine the canonical structure of an antibody. For example, those differences not fully reflected by Kabat numbering can be described by the numbering system of Chothia et al. and/or revealed by other techniques, for example, crystallography and two- or three-dimensional computational modeling. Accordingly, a given antibody sequence may be placed into a canonical class which allows for, among other things, identifying appropriate chassis sequences (e.g., based on a desire to include a variety of canonical structures in a library). Kabat numbering of antibody amino acid sequences and structural considerations as described by Chothia et al., loc. cit. and their implications for construing canonical aspects of antibody structure, are described in the literature. The subunit structures and three-dimensional configurations of different classes of immunoglobulins are well known in the art. For a review of the antibody structure, see Antibodies: A Laboratory Manual, Cold Spring Harbor Laboratory, eds. Harlow et al., 1988.

The CDR3 of the light chain and, particularly, the CDR3 of the heavy chain may constitute the most important determinants in antigen binding within the light and heavy chain variable regions. In some antibody constructs, the heavy chain CDR3 appears to constitute the major area of contact between the antigen and the antibody. In vitro selection schemes in which CDR3 alone is varied can be used to vary the binding properties of an antibody or determine which residues contribute to the binding of an antigen. Hence, CDR3 is typically the greatest source of molecular diversity within the antibody-binding side. H3, for example, can be as short as two amino acid residues or greater than 26 amino acids.

In a classical full-length antibody or immunoglobulin, each light (L) chain is linked to a heavy (H) chain by one covalent disulfide bond, while the two H chains are linked to each other by one or more disulfide bonds depending on the H chain isotype. The CH domain most proximal to VH is usually designated as CH1. The constant ("C") domains are not directly involved in antigen binding, but exhibit various effector functions, such as antibody-dependent, cell-mediated cytotoxicity and complement activation. The Fc region of an antibody is comprised within the heavy chain constant domains and is for example able to interact with cell surface located Fc receptors.

The sequence of antibody genes after assembly and somatic mutation is highly varied, and these varied genes are estimated to encode $10^{10}$ different antibody molecules (Immunoglobulin Genes, $2^{nd}$ ed., eds. Jonio et al., Academic Press, San Diego, CA, 1995). Accordingly, the immune system provides a repertoire of immunoglobulins. The term "repertoire" refers to at least one nucleotide sequence derived wholly or partially from at least one sequence encoding at least one immunoglobulin. The sequence(s) may be generated by rearrangement in vivo of the V, D, and J segments of heavy chains, and the V and J segments of light chains. Alternatively, the sequence(s) can be generated from a cell in response to which rearrangement occurs, e.g., in vitro stimulation. Alternatively, part or all of the sequence(s) may be obtained by DNA splicing, nucleotide synthesis, mutagenesis, and other methods, see, e.g., U.S. Pat. No. 5,565,332. A repertoire may include only one sequence or may include a plurality of sequences, including ones in a genetically diverse collection.

The term "Fc portion" or "Fc monomer" means in connection with this invention a polypeptide comprising at least one domain having the function of a CH2 domain and at least one domain having the function of a CH3 domain of an immunoglobulin molecule. As apparent from the term "Fc monomer", the polypeptide comprising those CH domains is a "polypeptide monomer". An Fc monomer can be a polypeptide comprising at least afragment of the constant region of an immunoglobulin excluding the first constant region immunoglobulin domain of the heavy chain (CH1), but maintaining at least a functional part of one CH2 domain and a functional part of one CH3 domain, wherein the CH2 domain is amino terminal to the CH3 domain. In a preferred aspect of this definition, an Fc monomer can be a polypeptide constant region comprising a portion of the Ig-Fc hinge region, a CH2 region and a CH3 region, wherein the hinge region is amino terminal to the CH2 domain. It is envisaged that the hinge region of the present invention promotes dimerization. Such Fc polypeptide molecules can be obtained by papain digestion of an immunoglobulin region (of course resulting in a dimer of two Fc polypeptide), for example and not limitation. In another aspect of this definition, an Fc monomer can be a polypeptide region comprising a portion of a CH2 region and a CH3 region. Such Fc polypeptide molecules can be obtained by pepsin digestion of an immunoglobulin molecule, for example and not limitation. In one embodiment, the polypeptide sequence of an Fc monomer is substantially similar to an Fc polypeptide sequence of: an $IgG_1$ Fc region, an $IgG_2$ Fc region, an $IgG_3$ Fc region, an $IgG_4$ Fc region, an IgM Fc region, an IgA Fc region, an IgD Fc region and an IgE Fc region. (See, e.g., Padlan, Molecular Immunology, 31(3), 169-217 (1993)). Because there is some variation between immunoglobulins, and solely for clarity, Fc monomer refers to the last two heavy chain constant region immunoglobulin domains of IgA, IgD, and IgG, and the last three heavy chain constant region immunoglobulin domains of IgE and IgM. As mentioned, the Fc monomer can also include the flexible hinge N-terminal to these domains. For IgA and IgM, the Fc monomer may include the J chain. For IgG, the Fc portion comprises immunoglobulin domains CH2 and CH3 and the hinge between the first two domains and CH2. Although the boundaries of the Fc portion may vary an example for a human IgG heavy chain Fc portion comprising a functional hinge, CH2 and CH3 domain can be defined e.g. to comprise residues D231 (of the hinge domain—corresponding to D234 in Table 1 below)) to P476, respectively L476 (for $IgG_4$) of the carboxyl-terminus of the CH3 domain, wherein the numbering is according to Kabat. The two Fc portions or Fc monomers, which are fused to each other via a peptide linker define the third domain of the antibody construct of the invention, which may also be defined as scFc domain.

In one embodiment of the invention it is envisaged that a scFc domain as disclosed herein, respectively the Fc monomers fused to each other are comprised only in the third domain of the antibody construct.

In line with the present invention an IgG hinge region can be identified by analogy using the Kabat numbering as set forth in Table 1. In line with the above, it is envisaged that a hinge domain/region of the present invention comprises the amino acid residues corresponding to the $IgG_1$ sequence stretch of D234 to P243 according to the Kabat numbering. It is likewise envisaged that a hinge domain/region of the present invention comprises or consists of the IgG1 hinge sequence DKTHTCPPCP (SEQ ID NO: 1449) (corresponding to the stretch D234 to P243 as shown in Table 1 below—variations of said sequence are also envisaged provided that the hinge region still promotes dimerization). In a preferred embodiment of the invention the glycosylation site at Kabat position 314 of the CH2 domains in the third domain of the antibody construct is removed by a N314X substitution, wherein X is any amino acid excluding Q. Said substitution is preferably a N314G substitution. In a more preferred embodiment, said CH2 domain additionally comprises the following substitutions (position according to Kabat) V321C and R309C (these substitutions introduce the intra domain cysteine disulfide bridge at Kabat positions 309 and 321).

It is also envisaged that the third domain of the antibody construct of the invention comprises or consists in an amino to carboxyl order: DKTHTCPPCP (SEQ ID NO: 1449) (i.e. hinge) —CH2—CH3-linker- DKTHTCPPCP (SEQ ID NO: 1449) (i.e. hinge) —CH2-CH3. The peptide linker of the aforementioned antibody construct is in a preferred embodiment characterized by the amino acid sequence Gly-Gly-Gly-Gly-Ser, i.e. Gly$_4$Ser (SEQ ID NO: 1), or polymers thereof, i.e. (Gly$_4$Ser)x, where x is an integer of 5 or greater (e.g. 5, 6, 7, 8 etc. or greater), 6 being preferred ((Gly4Ser) 6). Said construct may further comprise the aforementioned substitutions N314X, preferably N314G, and/or the further substitutions V321C and R309C. In a preferred embodiment of the antibody constructs of the invention as defined herein before, it is envisaged that the second domain binds to an extracellular epitope of the human and/or the *Macaca* CD3ε chain.

TABLE 1

Kabat numbering of the amino acid residues of the hinge region

| IMGT numbering for the hinge | IgG$_1$ amino acid translation | Kabat numbering |
|---|---|---|
| 1 | (E) | 226 |
| 2 | P | 227 |
| 3 | K | 228 |
| 4 | S | 232 |
| 5 | C | 233 |
| 6 | D | 234 |
| 7 | K | 235 |
| 8 | T | 236 |
| 9 | H | 237 |
| 10 | T | 238 |
| 11 | C | 239 |
| 12 | P | 240 |
| 13 | P | 241 |
| 14 | C | 242 |
| 15 | P | 243 |

In further embodiments of the present invention, the hinge domain/region comprises or consists of the IgG2 subtype hinge sequence ERKCCVECPPCP (SEQ ID NO: 1450), the IgG3 subtype hinge sequence ELKTPLDTTHTCPRCP (SEQ ID NO: 1451) or ELKTPLGDTTHTCPRCP (SEQ ID NO: 1458), and/or the IgG4 subtype hinge sequence ESKYGPPCPSCP (SEQ ID NO: 1452). The IgG1 subtype hinge sequence may be the following one EPKSCDKTHTCPPCP (as shown in Table 1 and SEQ ID NO: 1459). These core hinge regions are thus also envisaged in the context of the present invention.

The location and sequence of the IgG CH2 and IgG CD3 domain can be identified by analogy using the Kabat numbering as set forth in Table 2:

TABLE 2

Kabat numbering of the amino acid residues of the IgG CH2 and CH3 region

| IgG subtype | CH2 aa translation | CH2 Kabat numbering | CH3 aa translation | CH3 Kabat numbering |
|---|---|---|---|---|
| IgG$_1$ | APE . . . KAK | 244 . . . 360 | GQP . . . PGK | 361 . . . 478 |
| IgG$_2$ | APE . . . KTK | 244 . . . 360 | GQP . . . PGK | 361 . . . 478 |
| IgG$_3$ | APE . . . KTK | 244 . . . 360 | GQP . . . PGK | 361 . . . 478 |
| IgG$_4$ | APE . . . KAK | 244 . . . 360 | GQP . . . LGK | 361 . . . 478 |

In one embodiment of the invention the emphasized bold amino acid residues in the CH3 domain of the first or both Fc monomers are deleted.

The peptide linker, by whom the polypeptide monomers ("Fc portion" or "Fc monomer") of the third domain are fused to each other, preferably comprises at least 25 amino acid residues (25, 26, 27, 28, 29, 30 etc.). More preferably, this peptide linker comprises at least 30 amino acid residues (30, 31, 32, 33, 34, 35 etc.). It is also preferred that the linker comprises up to 40 amino acid residues, more preferably up to 35 amino acid residues, most preferably exactly 30 amino acid residues. A preferred embodiment of such peptide linker is characterized by the amino acid sequence Gly-Gly-Gly-Gly-Ser, i.e. Gly$_4$Ser (SEQ ID NO: 1), or polymers thereof, i.e. (Gly$_4$Ser)x, where x is an integer of 5 or greater (e.g. 6, 7 or 8). Preferably the integer is 6 or 7, more preferably the integer is 6.

In the event that a linker is used to fuse the first domain to the second domain, or the first or second domain to the third domain, this linker is preferably of a length and sequence sufficient to ensure that each of the first and second domains can, independently from one another, retain their differential binding specificities. For peptide linkers which connect the at least two binding domains (or two variable domains) in the antibody construct of the invention, those peptide linkers are preferred which comprise only a few number of amino acid residues, e.g. 12 amino acid residues or less. Thus, peptide linkers of 12, 11, 10, 9, 8, 7, 6 or 5 amino acid residues are preferred. An envisaged peptide linker with less than 5 amino acids comprises 4, 3, 2 or one amino acid(s), wherein Gly-rich linkers are preferred. A preferred embodiment of the peptide linker for a fusion first and the second domain is depicted in SEQ ID NO:1. A preferred linker embodiment of the peptide linker for a fusion the second and the third domain is a (Gly)$_4$-linker, respectively G$_4$-linker.

A particularly preferred "single" amino acid in the context of one of the above described "peptide linker" is Gly. Accordingly, said peptide linker may consist of the single amino acid Gly. In a preferred embodiment of the invention a peptide linker is characterized by the amino acid sequence Gly-Gly-Gly-Gly-Ser, i.e. Gly$_4$Ser (SEQ ID NO: 1), or polymers thereof, i.e. (Gly$_4$Ser)x, where x is an integer of 1 or greater (e.g. 2 or 3). Preferred linkers are depicted in SEQ ID NOs: 1 to 12. The characteristics of said peptide linker, which comprise the absence of the promotion of secondary structures, are known in the art and are described e.g. in Dall'Acqua et al. (Biochem. (1998) 37, 9266-9273), Cheadle et al. (Mol Immunol (1992) 29, 21-30) and Raag and Whitlow (FASEB (1995) 9(1), 73-80). Peptide linkers which furthermore do not promote any secondary structures are preferred. The linkage of said domains to each other can be provided, e.g., by genetic engineering, as described in the examples. Methods for preparing fused and operatively linked bispecific single chain constructs and expressing them in mammalian cells or bacteria are well-known in the art (e.g. WO 99/54440 or Sambrook et al., Molecular Cloning: A Laboratory Manual, Cold Spring Harbor Laboratory Press, Cold Spring Harbor, New York, 2001).

In a preferred embodiment of the antibody construct or the present invention the first and second domain form an antibody construct in a format selected from the group consisting of (scFv)₂, scFv-single domain mAb, diabody and oligomers of any of the those formats According to a particularly preferred embodiment, and as documented in the appended examples, the first and the second domain of the antibody construct of the invention is a "bispecific single chain antibody construct", more preferably a bispecific "single chain Fv" (scFv). Although the two domains of the Fv fragment, VL and VH, are coded for by separate genes, they can be joined, using recombinant methods, by a synthetic linker—as described hereinbefore—that enables them to be made as a single protein chain in which the VL and VH regions pair to form a monovalent molecule; see e.g., Huston et al. (1988) Proc. Natl. Acad. Sci USA 85:5879-5883). These antibody fragments are obtained using conventional techniques known to those with skill in the art, and the fragments are evaluated for function in the same manner as are whole or full-length antibodies. A single-chain variable fragment (scFv) is hence a fusion protein of the variable region of the heavy chain (VH) and of the light chain (VL) of immunoglobulins, usually connected with a short linker peptide of about ten to about 25 amino acids, preferably about 15 to 20 amino acids. The linker is usually rich in glycine for flexibility, as well as serine or threonine for solubility, and can either connect the N-terminus of the VH with the C-terminus of the VL, or vice versa. This protein retains the specificity of the original immunoglobulin, despite removal of the constant regions and introduction of the linker.

Bispecific single chain antibody constructs are known in the art and are described in WO 99/54440, Mack, J. Immunol. (1997), 158, 3965-3970, Mack, PNAS, (1995), 92, 7021-7025, Kufer, Cancer Immunol. Immunother., (1997), 45, 193-197, Löffler, Blood, (2000), 95, 6, 2098-2103, Brühl, Immunol., (2001), 166, 2420-2426, Kipriyanov, J. Mol. Biol., (1999), 293, 41-56. Techniques described for the production of single chain antibodies (see, inter *alia*, U.S. Pat. No. 4,946,778, Kontermann and Dubel (2010), loc. cit. and Little (2009), loc. cit.) can be adapted to produce single chain antibody constructs specifically recognizing (an) elected target(s).

Bivalent (also called divalent) or bispecific single-chain variable fragments (bi-scFvs or di-scFvs having the format (scFv)₂ can be engineered by linking two scFv molecules (e.g. with linkers as described hereinbefore). If these two scFv molecules have the same binding specificity, the resulting (scFv)₂ molecule will preferably be called bivalent (i.e. it has two valences for the same target epitope). If the two scFv molecules have different binding specificities, the resulting (scFv)₂ molecule will preferably be called bispecific. The linking can be done by producing a single peptide chain with two VH regions and two VL regions, yielding tandem scFvs (see e.g. Kufer P. et al., (2004) Trends in Biotechnology 22(5):238-244). Another possibility is the creation of scFv molecules with linker peptides that are too short for the two variable regions to fold together (e.g. about five amino acids), forcing the scFvs to dimerize. This type is known as diabodies (see e.g. Hollinger, Philipp et al., (July 1993) Proceedings of the National Academy of Sciences of the United States of America 90 (14): 6444-8).

In line with this invention either the first, the second or the first and the second domain may comprise a single domain antibody, respectively the variable domain or at least the CDRs of a single domain antibody. Single domain antibodies comprise merely one (monomeric) antibody variable domain which is able to bind selectively to a specific antigen, independently of other V regions or domains. The first single domain antibodies were engineered from havy chain antibodies found in camelids, and these are called V_HH fragments. Cartilaginous fishes also have heavy chain antibodies (IgNAR) from which single domain antibodies called V_NAR fragments can be obtained. An alternative approach is to split the dimeric variable domains from common immunoglobulins e.g. from humans or rodents into monomers, hence obtaining VH or VL as a single domain Ab. Although most research into single domain antibodies is currently based on heavy chain variable domains, nanobodies derived from light chains have also been shown to bind specifically to target epitopes. Examples of single domain antibodies are called sdAb, nanobodies or single variable domain antibodies.

A (single domain mAb)₂ is hence a monoclonal antibody construct composed of (at least) two single domain monoclonal antibodies, which are individually selected from the group comprising V_H, V_L, V_HH and V_NAR. The linker is preferably in the form of a peptide linker. Similarly, an "scFv-single domain mAb" is a monoclonal antibody construct composed of at least one single domain antibody as described above and one scFv molecule as described above. Again, the linker is preferably in the form of a peptide linker.

Whether or not an antibody construct competes for binding with another given antibody construct can be measured in a competition assay such as a competitive ELISA or a cell-based competition assay. Avidin-coupled microparticles (beads) can also be used. Similar to an avidin-coated ELISA plate, when reacted with a biotinylated protein, each of these beads can be used as a substrate on which an assay can be performed. Antigen is coated onto a bead and then precoated with the first antibody. The second antibody is added and any additional binding is determined. Possible means for the read-out includes flow cytometry.

T cells or T lymphocytes are a type of lymphocyte (itself a type of white blood cell) that play a central role in cell-mediated immunity. There are several subsets of T cells, each with a distinct function. T cells can be distinguished from other lymphocytes, such as B cells and NK cells, by the presence of a T cell receptor (TCR) on the cell surface. The TCR is responsible for recognizing antigens bound to major histocompatibility complex (MHC) molecules and is composed of two different protein chains. In 95% of the T cells, the TCR consists of an alpha (α) and beta (β) chain. When the TCR engages with antigenic peptide and MHC (peptide/MHC complex), the T lymphocyte is activated through a series of biochemical events mediated by associated enzymes, co-receptors, specialized adaptor molecules, and activated or released transcription factors.

The CD3 receptor complex is a protein complex and is composed of four chains. In mammals, the complex contains a CD3γ (gamma) chain, a CD3δ (delta) chain, and two CD3ε (epsilon) chains. These chains associate with the T cell receptor (TCR) and the so-called ((zeta) chain to form the T cell receptor CD3 complex and to generate an activation signal in ζ lymphocytes. The CD3γ (gamma), CD3δ (delta), and CD3ε (epsilon) chains are highly related cell-surface proteins of the immunoglobulin superfamily containing a single extracellular immunoglobulin domain. The intracellular tails of the CD3 molecules contain a single conserved motif known as an immunoreceptor tyrosine-based activation motif or ITAM for short, which is essential for the signaling capacity of the TCR. The CD3 epsilon molecule is a polypeptide which in humans is encoded by the CD3ε gene which resides on chromosome 11. The most preferred epitope of CD3 epsilon is comprised within amino acid residues 1-27 of the human CD3 epsilon extracellular domain. It is envisaged that antibody constructs according to the present invention typically and advantageously show less unspecific T cell activation, which is not desired in specific immunotherapy. This translates to a reduced risk of side effects.

The redirected lysis of target cells via the recruitment of T cells by a multispecific, at least bispecific, antibody construct involves cytolytic synapse formation and delivery of perforin and granzymes. The engaged T cells are capable of serial target cell lysis, and are not affected by immune escape mechanisms interfering with peptide antigen processing and presentation, or clonal T cell differentiation; see, for example, WO 2007/042261.

Cytotoxicity mediated by antibody constructs of the invention can be measured in various ways. Effector cells can be e.g. stimulated enriched (human) CD8 positive T cells or unstimulated (human) peripheral blood mononuclear cells (PBMC). If the target cells are of macaque origin or express or are transfected with macaque target cell surface antigen which is bound by the first domain, the effector cells should also be of macaque origin such as a macaque T cell line, e.g. 4119LnPx. The target cells should express (at least the extracellular domain of) the target cell surface antigen, e.g. human or macaque target cell surface antigen. Target cells can be a cell line (such as CHO) which is stably or transiently transfected with target cell surface antigen, e.g. human or macaque target cell surface antigen. Alternatively, the target cells can be a target cell surface antigen positive natural expresser cell line. Usually $EC_{50}$ values are expected to be lower with target cell lines expressing higher levels of target cell surface antigen on the cell surface. The effector to target cell (E:T) ratio is usually about 10:1, but can also vary. Cytotoxic activity of target cell surface antigenxCD3 bispecific antibody constructs can be measured in a $^{51}$Cr-release assay (incubation time of about 18 hours) or in a in a FACS-based cytotoxicity assay (incubation time of about 48 hours). Modifications of the assay incubation time (cytotoxic reaction) are also possible. Other methods of measuring cytotoxicity are well-known to the skilled person and comprise MTT or MTS assays, ATP-based assays including bioluminescent assays, the sulforhodamine B (SRB) assay, WST assay, clonogenic assay and the ECIS technology.

The cytotoxic activity mediated by target cell surface antigenxCD3 bispecific antibody constructs of the present invention is preferably measured in a cell-based cytotoxicity assay. It may also be measured in a $^{51}$Cr-release assay. It is represented by the $EC_{50}$ value, which corresponds to the half maximal effective concentration (concentration of the antibody construct which induces a cytotoxic response halfway between the baseline and maximum). Preferably, the $EC_{50}$ value of the target cell surface antigenxCD3 bispecific antibody constructs is ≤5000 pM or ≤4000 pM, more preferably ≤3000 pM or ≤2000 pM, even more preferably ≤1000 pM or ≤500 pM, even more preferably ≤400 pM or ≤300 pM, even more preferably ≤200 pM, even more preferably ≤100 pM, even more preferably ≤50 pM, even more preferably ≤20 pM or ≤10 pM, and most preferably ≤5 pM.

The above given $EC_{50}$ values can be measured in different assays. The skilled person is aware that an $EC_{50}$ value can be expected to be lower when stimulated/enriched CD8$^+$ T cells are used as effector cells, compared with unstimulated PBMC. It can furthermore be expected that the $EC_{50}$ values are lower when the target cells express a high number of the target cell surface antigen compared with a low target expression rat. For example, when stimulated/enriched human CD8$^+$ T cells are used as effector cells (and either target cell surface antigen transfected cells such as CHO cells or target cell surface antigen positive human cell lines are used as target cells), the $EC_{50}$ value of the target cell surface antigenxCD3 bispecific antibody construct is preferably ≤1000 pM, more preferably ≤500 pM, even more preferably ≤250 pM, even more preferably ≤100 pM, even more preferably ≤50 pM, even more preferably 10 pM, and most preferably ≤5 pM. When human PBMCs are used as effector cells, the $EC_{50}$ value of the target cell surface antigenxCD3 bispecific antibody construct is preferably ≤5000 pM or ≤4000 pM (in particular when the target cells are target cell surface antigen positive human cell lines), more preferably ≤2000 pM (in particular when the target cells are target cell surface antigen transfected cells such as CHO cells), more preferably ≤1000 pM or ≤500 pM, even more preferably ≤200 pM, even more preferably ≤150 pM, even more preferably ≤100 pM, and most preferably ≤50 pM, or lower. When a macaque T cell line such as LnPx4119 is used as effector cells, and a macaque target cell surface antigen transfected cell line such as CHO cells is used as target cell line, the $EC_{50}$ value of the target cell surface antigenxCD3 bispecific antibody construct is preferably ≤2000 pM or ≤1500 pM, more preferably ≤1000 pM or ≤500 pM, even more preferably ≤300 pM or ≤250 pM, even more preferably ≤100 pM, and most preferably ≤50 pM.

Preferably, the target cell surface antigenxCD3 bispecific antibody constructs of the present invention do not induce/mediate lysis or do not essentially induce/mediate lysis of target cell surface antigen negative cells such as CHO cells. The term "do not induce lysis", "do not essentially induce lysis", "do not mediate lysis" or "do not essentially mediate lysis" means that an antibody construct of the present invention does not induce or mediate lysis of more than 30%, preferably not more than 20%, more preferably not more than 10%, particularly preferably not more than 9%, 8%, 7%, 6% or 5% of target cell surface antigen negative cells, whereby lysis of a target cell surface antigen positive human cell line is set to be 100%. This usually applies for concentrations of the antibody construct of up to 500 nM. The skilled person knows how to measure cell lysis without further ado. Moreover, the present specification teaches specific instructions how to measure cell lysis.

The difference in cytotoxic activity between the monomeric and the dimeric isoform of individual target cell surface antigenxCD3 bispecific antibody constructs is referred to as "potency gap". This potency gap can e.g. be calculated as ratio between $EC_{50}$ values of the molecule's monomeric and dimeric form. Potency gaps of the target cell surface antigenxCD3 bispecific antibody constructs of the present invention are preferably ≤5, more preferably ≤4, even more preferably ≤3, even more preferably ≤2 and most preferably ≤1.

The first and/or the second (or any further) binding domain(s) of the antibody construct of the invention is/are preferably cross-species specific for members of the mammalian order of primates. Cross-species specific CD3 binding domains are, for example, described in WO 2008/119567. According to one embodiment, the first and/or second binding domain, in addition to binding to human target cell surface antigen and human CD3, respectively, will also bind to target cell surface antigen/CD3 of primates including (but not limited to) new world primates (such as *Callithrix jacchus, Saguinus Oedipus* or *Saimiri sciureus*), old world primates (such baboons and macaques), gibbons, and non-human homininae.

In one embodiment of the antibody construct of the invention the first domain binds to human target cell surface antigen and further binds to macaque target cell surface antigen, such as target cell surface antigen of *Macaca fascicularis*, and more preferably, to macaque target cell surface antigen expressed on the surface macaque cells. The affinity of the first binding domain for macaque target cell surface antigen is preferably ≤15 nM, more preferably ≤10 nM, even more preferably ≤5 nM, even more preferably ≤1 nM, even more preferably ≤0.5 nM, even more preferably ≤0.1 nM, and most preferably ≤0.05 nM or even ≤0.01 nM.

Preferably the affinity gap of the antibody constructs according to the invention for binding macaque target cell surface antigen versus human target cell surface antigen [ma target cell surface antigen:hu target cell surface antigen](as determined e.g. by BiaCore™ or by Scatchard analysis) is <100, preferably <20, more preferably <15, further preferably <10, even more preferably <8, more preferably <6 and most preferably <2. Preferred ranges for the affinity gap of the antibody constructs according to the invention for binding macaque target cell surface antigen versus human target cell surface antigen are between 0.1 and 20, more preferably between 0.2 and 10, even more preferably between 0.3 and 6, even more preferably between 0.5 and 3 or between 0.5 and 2.5, and most preferably between 0.5 and 2 or between 0.6 and 2.

The second (binding) domain of the antibody construct of the invention binds to human CD3 epsilon and/or to *Macaca* CD3 epsilon. In a preferred embodiment the second domain further bind to *Callithrix jacchus, Saguinus Oedipus* or *Saimiri sciureus* CD3 epsilon. *Callithrix jacchus* and *Saguinus oedipus* are both new world primate belonging to the family of Callitrichidae, while *Saimiri sciureus* is a new world primate belonging to the family of Cebidae.

It is preferred for the antibody construct of the present invention that the second domain which binds to an extracellular epitope of the human and/or the *Macaca* CD3 on the comprises a VL region comprising CDR-L1, CDR-L2 and CDR-L3 selected from:

(a) CDR-L1 as depicted in SEQ ID NO: 27 of WO 2008/119567, CDR-L2 as depicted in SEQ ID NO: 28 of WO 2008/119567 and CDR-L3 as depicted in SEQ ID NO: 29 of WO 2008/119567;

(b) CDR-L1 as depicted in SEQ ID NO: 117 of WO 2008/119567, CDR-L2 as depicted in SEQ ID NO: 118 of WO 2008/119567 and CDR-L3 as depicted in SEQ ID NO: 119 of WO 2008/119567; and (c) CDR-L1 as depicted in SEQ ID NO: 153 of WO 2008/119567, CDR-L2 as depicted in SEQ ID NO: 154 of WO 2008/119567 and CDR-L3 as depicted in SEQ ID NO: 155 of WO 2008/119567.

In an also preferred embodiment of the antibody construct of the present invention, the second domain which binds to an extracellular epitope of the human and/or the *Macaca* CD3 epsilon chain comprises a VH region comprising CDR-H 1, CDR-H2 and CDR-H3 selected from:

(a) CDR-H1 as depicted in SEQ ID NO: 12 of WO 2008/119567, CDR-H2 as depicted in SEQ ID NO: 13 of WO 2008/119567 and CDR-H3 as depicted in SEQ ID NO: 14 of WO 2008/119567;

(b) CDR-H1 as depicted in SEQ ID NO: 30 of WO 2008/119567, CDR-H2 as depicted in SEQ ID NO: 31 of WO 2008/119567 and CDR-H3 as depicted in SEQ ID NO: 32 of WO 2008/119567;

(c) CDR-H1 as depicted in SEQ ID NO: 48 of WO 2008/119567, CDR-H2 as depicted in SEQ ID NO: 49 of WO 2008/119567 and CDR-H3 as depicted in SEQ ID NO: 50 of WO 2008/119567;

(d) CDR-H1 as depicted in SEQ ID NO: 66 of WO 2008/119567, CDR-H2 as depicted in SEQ ID NO: 67 of WO 2008/119567 and CDR-H3 as depicted in SEQ ID NO: 68 of WO 2008/119567;

(e) CDR-H1 as depicted in SEQ ID NO: 84 of WO 2008/119567, CDR-H2 as depicted in SEQ ID NO: 85 of WO 2008/119567 and CDR-H3 as depicted in SEQ ID NO: 86 of WO 2008/119567;

(f) CDR-H1 as depicted in SEQ ID NO: 102 of WO 2008/119567, CDR-H2 as depicted in SEQ ID NO: 103 of WO 2008/119567 and CDR-H3 as depicted in SEQ ID NO: 104 of WO 2008/119567;

(g) CDR-H1 as depicted in SEQ ID NO: 120 of WO 2008/119567, CDR-H2 as depicted in SEQ ID NO: 121 of WO 2008/119567 and CDR-H3 as depicted in SEQ ID NO: 122 of WO 2008/119567;

(h) CDR-H1 as depicted in SEQ ID NO: 138 of WO 2008/119567, CDR-H2 as depicted in SEQ ID NO: 139 of WO 2008/119567 and CDR-H3 as depicted in SEQ ID NO: 140 of WO 2008/119567;

(i) CDR-H1 as depicted in SEQ ID NO: 156 of WO 2008/119567, CDR-H2 as depicted in SEQ ID NO: 157 of WO 2008/119567 and CDR-H3 as depicted in SEQ ID NO: 158 of WO 2008/119567; and (j) CDR-H1 as depicted in SEQ ID NO: 174 of WO 2008/119567, CDR-H2 as depicted in SEQ ID NO: 175 of WO 2008/119567 and CDR-H3 as depicted in SEQ ID NO: 176 of WO 2008/119567.

In a preferred embodiment of the antibody construct of the invention the above described three groups of VL CDRs are combined with the above described ten groups of VH CDRs within the second binding domain to form (30) groups, each comprising CDR-L 1-3 and CDR-H 1-3.

It is preferred for the antibody construct of the present invention that the second domain which binds to CD3 comprises a VL region selected from the group consisting of a VL region as depicted in SEQ ID NO: 17, 21, 35, 39, 53, 57, 71, 75, 89, 93, 107, 111, 125, 129, 143, 147, 161, 165, 179 or 183 of WO 2008/119567 or as depicted in SEQ ID NO: 13.

It is also preferred that the second domain which binds to CD3 comprises a VH region selected from the group consisting of a VH region as depicted in SEQ ID NO: 15, 19, 33, 37, 51, 55, 69, 73, 87, 91, 105, 109, 123, 127, 141, 145, 159, 163, 177 or 181 of WO 2008/119567 or as depicted in SEQ ID NO: 14.

More preferably, the antibody construct of the present invention is characterized by a second domain which binds to CD3 comprising a VL region and a VH region selected from the group consisting of:

(a) a VL region as depicted in SEQ ID NO: 17 or 21 of WO 2008/119567 and a VH region as depicted in SEQ ID NO: 15 or 19 of WO 2008/119567;

(b) a VL region as depicted in SEQ ID NO: 35 or 39 of WO 2008/119567 and a VH region as depicted in SEQ ID NO: 33 or 37 of WO 2008/119567;

(c) a VL region as depicted in SEQ ID NO: 53 or 57 of WO 2008/119567 and a VH region as depicted in SEQ ID NO: 51 or 55 of WO 2008/119567;

(d) a VL region as depicted in SEQ ID NO: 71 or 75 of WO 2008/119567 and a VH region as depicted in SEQ ID NO: 69 or 73 of WO 2008/119567;

(e) a VL region as depicted in SEQ ID NO: 89 or 93 of WO 2008/119567 and a VH region as depicted in SEQ ID NO: 87 or 91 of WO 2008/119567;

(f) a VL region as depicted in SEQ ID NO: 107 or 111 of WO 2008/119567 and a VH region as depicted in SEQ ID NO: 105 or 109 of WO 2008/119567;

(g) a VL region as depicted in SEQ ID NO: 125 or 129 of WO 2008/119567 and a VH region as depicted in SEQ ID NO: 123 or 127 of WO 2008/119567;

(h) a VL region as depicted in SEQ ID NO: 143 or 147 of WO 2008/119567 and a VH region as depicted in SEQ ID NO: 141 or 145 of WO 2008/119567;

(i) a VL region as depicted in SEQ ID NO: 161 or 165 of WO 2008/119567 and a VH region as depicted in SEQ ID NO: 159 or 163 of WO 2008/119567; and (j) a VL region as depicted in SEQ ID NO: 179 or 183 of WO 2008/119567 and a VH region as depicted in SEQ ID NO: 177 or 181 of WO 2008/119567.

Also preferred in connection with the antibody construct of the present invention is a second domain which binds to CD3 comprising a VL region as depicted in SEQ ID NO: 13 and a VH region as depicted in SEQ ID NO: 14.

According to a preferred embodiment of the antibody construct of the present invention, the first and/or the second domain have the following format: The pairs of VH regions and VL regions are in the format of a single chain antibody (scFv). The VH and VL regions are arranged in the order VH-VL or VL-VH. It is preferred that the VH-region is positioned N-terminally of a linker sequence, and the VL-region is positioned C-terminally of the linker sequence.

A preferred embodiment of the above described antibody construct of the present invention is characterized by the second domain which binds to CD3 comprising an amino acid sequence selected from the group consisting of SEQ ID NOs: 23, 25, 41, 43, 59, 61, 77, 79, 95, 97, 113, 115, 131, 133, 149, 151, 167, 169, 185 or 187 of WO 2008/119567 or depicted in SEQ ID NO: 15.

Covalent modifications of the antibody constructs are also included within the scope of this invention, and are generally, but not always, done post-translationally. For example, several types of covalent modifications of the antibody construct are introduced into the molecule by reacting specific amino acid residues of the antibody construct with an organic derivatizing agent that is capable of reacting with selected side chains or the N- or C-terminal residues.

Cysteinyl residues most commonly are reacted with α-haloacetates (and corresponding amines), such as chloroacetic acid or chloroacetamide, to give carboxymethyl or carboxyamidomethyl derivatives. Cysteinyl residues also are derivatized by reaction with bromotrifluoroacetone, α-bromo-β-(5-imidozoyl)propionic acid, chloroacetyl phosphate, N-alkylmaleimides, 3-nitro-2-pyridyl disulfide, methyl 2-pyridyl disulfide, p-chloromercuribenzoate, 2-chloromercuri-4-nitrophenol, or chloro-7-nitrobenzo-2-oxa-1,3-diazole.

Histidyl residues are derivatized by reaction with diethylpyrocarbonate at pH 5.5-7.0 because this agent is relatively specific for the histidyl side chain. Para-bromophenacyl bromide also is useful; the reaction is preferably performed in 0.1 M sodium cacodylate at pH 6.0. Lysinyl and amino terminal residues are reacted with succinic or other carboxylic acid anhydrides. Derivatization with these agents has the effect of reversing the charge of the lysinyl residues. Other suitable reagents for derivatizing alpha-amino-containing residues include imidoesters such as methyl picolinimidate; pyridoxal phosphate; pyridoxal; chloroborohydride; trinitrobenzenesulfonic acid; O-methylisourea; 2,4-pentanedione; and transaminase-catalyzed reaction with glyoxylate.

Arginyl residues are modified by reaction with one or several conventional reagents, among them phenylglyoxal, 2,3-butanedione, 1,2-cyclohexanedione, and ninhydrin. Derivatization of arginine residues requires that the reaction be performed in alkaline conditions because of the high pKa of the guanidine functional group. Furthermore, these reagents may react with the groups of lysine as well as the arginine epsilon-amino group.

The specific modification of tyrosyl residues may be made, with particular interest in introducing spectral labels into tyrosyl residues by reaction with aromatic diazonium compounds or tetranitromethane. Most commonly, N-acetylimidizole and tetranitromethane are used to form O-acetyl tyrosyl species and 3-nitro derivatives, respectively. Tyrosyl residues are iodinated using $^{125}I$ or $^{131}I$ to prepare labeled proteins for use in radioimmunoassay, the chloramine T method described above being suitable.

Carboxyl side groups (aspartyl or glutamyl) are selectively modified by reaction with carbodiimides (R'—N=C=N—R'), where R and R' are optionally different alkyl groups, such as 1-cyclohexyl-3-(2-morpholinyl-4-ethyl) carbodiimide or 1-ethyl-3-(4-azonia-4,4-dimethylpentyl) carbodiimide. Furthermore, aspartyl and glutamyl residues are converted to asparaginyl and glutaminyl residues by reaction with ammonium ions.

Derivatization with bifunctional agents is useful for crosslinking the antibody constructs of the present invention to a water-insoluble support matrix or surface for use in a variety of methods. Commonly used crosslinking agents include, e.g., 1,1-bis(diazoacetyl)-2-phenylethane, glutaraldehyde, N-hydroxysuccinimide esters, for example, esters with 4-azidosalicylic acid, homobifunctional imidoesters, including disuccinimidyl esters such as 3,3'-dithiobis(succinimidylpropionate), and bifunctional maleimides such as bis-N-maleimido-1,8-octane. Derivatizing agents such as methyl-3-[(p-azidophenyl)dithio]propioimidate yield photoactivatable intermediates that are capable of forming crosslinks in the presence of light. Alternatively, reactive water-insoluble matrices such as cyanogen bromide-activated carbohydrates and the reactive substrates as described in U.S. Pat. Nos. 3,969,287; 3,691,016; 4,195,128; 4,247,642; 4,229,537; and 4,330,440 are employed for protein immobilization.

Glutaminyl and asparaginyl residues are frequently deamidated to the corresponding glutamyl and aspartyl residues, respectively. Alternatively, these residues are deamidated under mildly acidic conditions. Either form of these residues falls within the scope of this invention.

Other modifications include hydroxylation of proline and lysine, phosphorylation of hydroxyl groups of seryl or threonyl residues, methylation of the α-amino groups of lysine, arginine, and histidine side chains (T. E. Creighton, Proteins: Structure and Molecular Properties, W. H. Freeman & Co., San Francisco, 1983, pp. 79-86), acetylation of the N-terminal amine, and amidation of any C-terminal carboxyl group.

Another type of covalent modification of the antibody constructs included within the scope of this invention comprises altering the glycosylation pattern of the protein. As is known in the art, glycosylation patterns can depend on both the sequence of the protein (e.g., the presence or absence of particular glycosylation amino acid residues, discussed below), or the host cell or organism in which the protein is produced. Particular expression systems are discussed below.

Glycosylation of polypeptides is typically either N-linked or O-linked. N-linked refers to the attachment of the carbo-hydrate moiety to the side chain of an asparagine residue. The tri-peptide sequences asparagine-X-serine and aspara-gine-X-threonine, where X is any amino acid except proline, are the recognition sequences for enzymatic attachment of the carbohydrate moiety to the asparagine side chain. Thus, the presence of either of these tri-peptide sequences in a polypeptide creates a potential glycosylation site. O-linked glycosylation refers to the attachment of one of the sugars N-acetylgalactosamine, galactose, or xylose, to a hydroxyamino acid, most commonly serine or threonine, although 5-hydroxyproline or 5-hydroxylysine may also be used.

Addition of glycosylation sites to the antibody construct is conveniently accomplished by altering the amino acid sequence such that it contains one or more of the above-described tri-peptide sequences (for N-linked glycosylation sites). The alteration may also be made by the addition of, or substitution by, one or more serine or threonine residues to the starting sequence (for O-linked glycosylation sites). For ease, the amino acid sequence of an antibody construct is preferably altered through changes at the DNA level, particularly by mutating the DNA encoding the polypeptide at preselected bases such that codons are generated that will translate into the desired amino acids.

Another means of increasing the number of carbohydrate moieties on the antibody construct is by chemical or enzy-matic coupling of glycosides to the protein. These proce-dures are advantageous in that they do not require produc-tion of the protein in a host cell that has glycosylation capabilities for N- and O-linked glycosylation. Depending on the coupling mode used, the sugar(s) may be attached to (a) arginine and histidine, (b) free carboxyl groups, (c) free sulfhydryl groups such as those of cysteine, (d) free hydroxyl groups such as those of serine, threonine, or hydroxyproline, (e) aromatic residues such as those of phenylalanine, tyrosine, or tryptophan, or (f) the amide group of glutamine. These methods are described in WO 87/05330, and in Aplin and Wriston, 1981, CRC Crit. Rev. Biochem., pp. 259-306.

Removal of carbohydrate moieties present on the starting antibody construct may be accomplished chemically or enzymatically. Chemical deglycosylation requires exposure of the protein to the compound trifluoromethanesulfonic acid, or an equivalent compound. This treatment results in the cleavage of most or all sugars except the linking sugar (N-acetylglucosamine or N-acetylgalactosamine), while leaving the polypeptide intact. Chemical deglycosylation is described by Hakimuddin et al., 1987, *Arch. Biochem. Biophys.* 259:52 and by Edge et al., 1981, *Anal. Biochem.* 118:131. Enzymatic cleavage of carbohydrate moieties on polypeptides can be achieved by the use of a variety of endo-and exo-glycosidases as described by Thotakura et al., 1987, Meth. Enzymol. 138:350. Glycosylation at potential glyco-sylation sites may be prevented by the use of the compound tunicamycin as described by Duskin et al., 1982, J. Biol. Chem. 257:3105. Tunicamycin blocks the formation of protein-N-glycoside linkages.

Other modifications of the antibody construct are also contemplated herein. For example, another type of covalent modification of the antibody construct comprises linking the antibody construct to various non-proteinaceous polymers, including, but not limited to, various polyols such as polyethylene glycol, polypropylene glycol, polyoxyalkylenes, or copolymers of polyethylene glycol and polypropylene gly-col, in the manner set forth in U.S. Pat. Nos. 4,640,835; 4,496,689; 4,301,144; 4,670,417; 4,791,192 or 4,179,337. In addition, as is known in the art, amino acid substitutions may be made in various positions within the antibody construct, e.g. in order to facilitate the addition of polymers such as PEG.

In some embodiments, the covalent modification of the antibody constructs of the invention comprises the addition of one or more labels. The labelling group may be coupled to the antibody construct via spacer arms of various lengths to reduce potential steric hindrance. Various methods for labelling proteins are known in the art and can be used in performing the present invention. The term "label" or "label-ling group" refers to any detectable label. In general, labels fall into a variety of classes, depending on the assay in which they are to be detected—the following examples include, but are not limited to:

a) isotopic labels, which may be radioactive or heavy isotopes, such as radioisotopes or radionuclides (e.g., $^{3}H$, $^{14}C$, $^{15}N$, $^{35}S$, $^{89}Zr$, $^{90}Y$, $^{99}Tc$, $^{111}In$, $^{125}I$, $^{131}I$)

b) magnetic labels (e.g., magnetic particles)

c) redox active moieties d) optical dyes (including, but not limited to, chro-mophores, phosphors and fluorophores) such as fluo-rescent groups (e.g., FITC, rhodamine, lanthanide phosphors), chemiluminescent groups, and fluoro-phores which can be either "small molecule" fluores or proteinaceous fluores e) enzymatic groups (e.g. horseradish peroxidase, β-ga-lactosidase, luciferase, alkaline phosphatase)

f) biotinylated groups g) predetermined polypeptide epitopes recognized by a secondary reporter (e.g., leucine zipper pair sequences, binding sides for secondary antibodies, metal binding domains, epitope tags, etc.)

By "fluorescent label" is meant any molecule that may be detected via its inherent fluorescent properties. Suitable fluorescent labels include, but are not limited to, fluorescein, rhodamine, tetramethylrhodamine, eosin, erythrosin, cou-marin, methyl-coumarins, pyrene, Malacite green, stilbene, Lucifer Yellow, Cascade Blue J, Texas Red, IAEDANS, EDANS, BODIPY FL, LC Red 640, Cy 5, Cy 5.5, LC Red 705, Oregon green, the Alexa-Fluor dyes (Alexa Fluor 350, Alexa Fluor 430, Alexa Fluor 488, Alexa Fluor 546, Alexa Fluor 568, Alexa Fluor 594, Alexa Fluor 633, Alexa Fluor 660, Alexa Fluor 680), Cascade Blue, Cascade Yellow and R-phycoerythrin (PE) (Molecular Probes, Eugene, OR), FITC, Rhodamine, and Texas Red (Pierce, Rockford, IL), Cy5, Cy5.5, Cy7 (Amersham Life Science, Pittsburgh, PA). Suitable optical dyes, including fluorophores, are described in Molecular Probes Handbook by Richard P. Haugland.

Suitable proteinaceous fluorescent labels also include, but are not limited to, green fluorescent protein, including a *Renilla*, Ptilosarcus, or *Aequorea* species of GFP (Chalfie et al., 1994, Science 263:802-805), EGFP (Clontech Labora-tories, Inc., Genbank Accession Number U55762), blue fluorescent protein (BFP, Quantum Biotechnologies, Inc. 1801 de Maisonneuve Blvd. West, 8th Floor, Montreal, Quebec, Canada H3H 1J9; Stauber, 1998, Biotechniques 24:462-471; Heim et al., 1996, Curr. Biol. 6:178-182), enhanced yellow fluorescent protein (EYFP, Clontech Labo-ratories, Inc.), luciferase (Ichiki et al., 1993, *J. Immunol.* 150:5408-5417), β galactosidase (Nolan et al., 1988, *Proc. Natl. Acad. Sci. U.S.A.* 85:2603-2607) and *Renilla* (WO92/ 15673, WO95/07463, WO98/14605, WO98/26277, WO99/

49019, U.S. Pat. Nos. 5,292,658; 5,418,155; 5,683,888; 5,741,668; 5,777,079; 5,804,387; 5,874,304; 5,876,995; 5,925,558).

The antibody construct of the invention may also comprise additional domains, which are e.g. helpful in the isolation of the molecule or relate to an adapted pharmacokinetic profile of the molecule. Domains helpful for the isolation of an antibody construct may be selected from peptide motives or secondarily introduced moieties, which can be captured in an isolation method, e.g. an isolation column. Non-limiting embodiments of such additional domains comprise peptide motives known as Myc-tag, HAT-tag, HA-tag, TAP-tag, GST-tag, chitin binding domain (CBD-tag), maltose binding protein (MBP-tag), Flag-tag, Strep-tag and variants thereof (e.g. StrepII-tag) and His-tag. All herein disclosed antibody constructs characterized by the identified CDRs may comprise a His-tag domain, which is generally known as a repeat of consecutive His residues in the amino acid sequence of a molecule, preferably of five, and more preferably of six His residues (hexa-histidine). The His-tag may be located e.g. at the N- or C-terminus of the antibody construct, preferably it is located at the C-terminus. Most preferably, a hexa-histidine tag (HHHHHH) (SEQ ID NO:16) is linked via peptide bond to the C-terminus of the antibody construct according to the invention. Additionally, a conjugate system of PLGA-PEG-PLGA may be combined with a poly-histidine tag for sustained release application and improved pharmacokinetic profile.

Amino acid sequence modifications of the antibody constructs described herein are also contemplated. For example, it may be desirable to improve the binding affinity and/or other biological properties of the antibody construct. Amino acid sequence variants of the antibody constructs are prepared by introducing appropriate nucleotide changes into the antibody constructs nucleic acid, or by peptide synthesis. All of the below described amino acid sequence modifications should result in an antibody construct which still retains the desired biological activity (binding to the target cell surface antigen and to CD3) of the unmodified parental molecule.

The term "amino acid" or "amino acid residue" typically refers to an amino acid having its art recognized definition such as an amino acid selected from the group consisting of: alanine (Ala or A); arginine (Arg or R); asparagine (Asn or N); aspartic acid (Asp or D); cysteine (Cys or C); glutamine (Gln or Q); glutamic acid (Glu or E); glycine (Gly or G); histidine (His or H); isoleucine (He or I): leucine (Leu or L); lysine (Lys or K); methionine (Met or M); phenylalanine (Phe or F); pro line (Pro or P); serine (Ser or S); threonine (Thr or T); tryptophan (Trp or W); tyrosine (Tyr or Y); and valine (Val or V), although modified, synthetic, or rare amino acids may be used as desired. Generally, amino acids can be grouped as having a nonpolar side chain (e.g., Ala, Cys, He, Leu, Met, Phe, Pro, Val); a negatively charged side chain (e.g., Asp, Glu); a positively charged sidechain (e.g., Arg, His, Lys); or an uncharged polar side chain (e.g., Asn, Cys, Gln, Gly, His, Met, Phe, Ser, Thr, Trp, and Tyr).

Amino acid modifications include, for example, deletions from, and/or insertions into, and/or substitutions of, residues within the amino acid sequences of the antibody constructs. Any combination of deletion, insertion, and substitution is made to arrive at the final construct, provided that the final construct possesses the desired characteristics. The amino acid changes also may alter post-translational processes of the antibody constructs, such as changing the number or position of glycosylation sites.

For example, 1, 2, 3, 4, 5, or 6 amino acids may be inserted, substituted or deleted in each of the CDRs (of course, dependent on their length), while 1, 2, 3, 4, 5, 6, 7, 8, 9, 10, 11, 12, 13, 14, 15, 16, 17, 18, 19, 20, or 25 amino acids may be inserted, substituted or deleted in each of the FRs. Preferably, amino acid sequence insertions into the antibody construct include amino- and/or carboxyl-terminal fusions ranging in length from 1, 2, 3, 4, 5, 6, 7, 8, 9 or 10 residues to polypeptides containing a hundred or more residues, as well as intra-sequence insertions of single or multiple amino acid residues. Corresponding modifications may also performed within the third domain of the antibody construct of the invention. An insertional variant of the antibody construct of the invention includes the fusion to the N-terminus or to the C-terminus of the antibody construct of an enzyme or the fusion to a polypeptide.

The sites of greatest interest for substitutional mutagenesis include (but are not limited to) the CDRs of the heavy and/or light chain, in particular the hypervariable regions, but FR alterations in the heavy and/or light chain are also contemplated. The substitutions are preferably conservative substitutions as described herein. Preferably, 1, 2, 3, 4, 5, 6, 7, 8, 9, or 10 amino acids may be substituted in a CDR, while 1, 2, 3, 4, 5, 6, 7, 8, 9, 10, 11, 12, 13, 14, 15, 16, 17, 18, 19, 20, or 25 amino acids may be substituted in the framework regions (FRs), depending on the length of the CDR or FR. For example, if a CDR sequence encompasses 6 amino acids, it is envisaged that one, two or three of these amino acids are substituted. Similarly, if a CDR sequence encompasses 15 amino acids it is envisaged that one, two, three, four, five or six of these amino acids are substituted.

A useful method for identification of certain residues or regions of the antibody constructs that are preferred locations for mutagenesis is called "alanine scanning mutagenesis" as described by Cunningham and Wells in Science, 244: 1081-1085 (1989). Here, a residue or group of target residues within the antibody construct is/are identified (e.g. charged residues such as arg, asp, his, lys, and glu) and replaced by a neutral or negatively charged amino acid (most preferably alanine or polyalanine) to affect the interaction of the amino acids with the epitope.

Those amino acid locations demonstrating functional sensitivity to the substitutions are then refined by introducing further or other variants at, or for, the sites of substitution. Thus, while the site or region for introducing an amino acid sequence variation is predetermined, the nature of the mutation per se needs not to be predetermined. For example, to analyze or optimize the performance of a mutation at a given site, alanine scanning or random mutagenesis may be conducted at a target codon or region, and the expressed antibody construct variants are screened for the optimal combination of desired activity. Techniques for making substitution mutations at predetermined sites in the DNA having a known sequence are well known, for example, M13 primer mutagenesis and PCR mutagenesis. Screening of the mutants is done using assays of antigen binding activities, such as the target cell surface antigen or CD3 binding.

Generally, if amino acids are substituted in one or more or all of the CDRs of the heavy and/or light chain, it is preferred that the then-obtained "substituted" sequence is at least 60% or 65%, more preferably 70% or 75%, even more preferably 80% or 85%, and particularly preferably 90% or 95% identical to the "original" CDR sequence. This means that it is dependent of the length of the CDR to which degree it is identical to the "substituted" sequence. For example, a CDR having 5 amino acids is preferably 80% identical to its substituted sequence in order to have at least one amino acid substituted. Accordingly, the CDRs of the antibody construct may have different degrees of identity to their substituted sequences, e.g., CDRL1 may have 80%, while CDRL3 may have 90%.

Preferred substitutions (or replacements) are conservative substitutions. However, any substitution (including non-conservative substitution or one or more from the "exemplary substitutions" listed in Table 3, below) is envisaged as long as the antibody construct retains its capability to bind to the target cell surface antigen via the first domain and to CD3, respectively CD3 epsilon, via the second domain and/or its CDRs have an identity to the then substituted sequence (at least 60% or 65%, more preferably 70% or 75%, even more preferably 80% or 85%, and particularly preferably 90% or 95% identical to the "original" CDR sequence).

Conservative substitutions are shown in Table 3 under the heading of "preferred substitutions". If such substitutions result in a change in biological activity, then more substantial changes, denominated "exemplary substitutions" in Table 3, or as further described below in reference to amino acid classes, may be introduced and the products screened for a desired characteristic.

TABLE 3

Amino acid substitutions

| Original | Exemplary Substitutions | Preferred Substitutions |
|---|---|---|
| Ala (A) | val, leu, ile | val |
| Arg (R) | lys, gln, asn | lys |
| Asn (N) | gln, his, asp, lys, arg | gln |
| Asp (D) | glu, asn | glu |
| Cys (C) | ser, ala | ser |
| Gln (Q) | asn, glu | asn |
| Glu (E) | asp, gln | asp |
| Gly (G) | Ala | ala |
| His (H) | asn, gln, lys, arg | arg |
| Ile (I) | leu, val, met, ala, phe | leu |
| Leu (L) | norleucine, ile, val, met, ala | ile |
| Lys (K) | arg, gln, asn | arg |
| Met (M) | leu, phe, ile | leu |
| Phe (F) | leu, val, ile, ala, tyr | tyr |
| Pro (P) | Ala | ala |
| Ser (S) | Thr | thr |
| Thr (T) | Ser | ser |
| Trp (W) | tyr, phe | tyr |
| Tyr (Y) | trp, phe, thr, ser | phe |
| Val (V) | ile, leu, met, phe, ala | leu |

Substantial modifications in the biological properties of the antibody construct of the present invention are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties: (1) hydrophobic: norleucine, met, ala, val, leu, ile; (2) neutral hydrophilic: cys, ser, thr, asn, gln; (3) acidic: asp, glu; (4) basic: his, lys, arg; (5) residues that influence chain orientation: gly, pro; and (6) aromatic: trp, tyr, phe.

Non-conservative substitutions will entail exchanging a member of one of these classes for another class. Any cysteine residue not involved in maintaining the proper conformation of the antibody construct may be substituted, generally with serine, to improve the oxidative stability of the molecule and prevent aberrant crosslinking. Conversely, cysteine bond(s) may be added to the antibody to improve its stability (particularly where the antibody is an antibody fragment such as an Fv fragment).

For amino acid sequences, sequence identity and/or similarity is determined by using standard techniques known in the art, including, but not limited to, the local sequence identity algorithm of Smith and Waterman, 1981, *Adv. Appl. Math.* 2:482, the sequence identity alignment algorithm of Needleman and Wunsch, 1970, *J. Mol. Biol.* 48:443, the search for similarity method of Pearson and Lipman, 1988, *Proc. Nat. Acad. Sci. U.S.A.* 85:2444, computerized implementations of these algorithms (GAP, BESTFIT, FASTA, and TFASTA in the Wisconsin Genetics Software Package, Genetics Computer Group, 575 Science Drive, Madison, Wis.), the Best Fit sequence program described by Devereux et al., 1984, *Nucl. Acid Res.* 12:387-395, preferably using the default settings, or by inspection. Preferably, percent identity is calculated by FastDB based upon the following parameters: mismatch penalty of 1; gap penalty of 1; gap size penalty of 0.33; and joining penalty of 30, "Current Methods in Sequence Comparison and Analysis," Macromolecule Sequencing and Synthesis, Selected Methods and Applications, pp 127-149 (1988), Alan R. Liss, Inc.

An example of a useful algorithm is PILEUP. PILEUP creates a multiple sequence alignment from a group of related sequences using progressive, pairwise alignments. It can also plot a tree showing the clustering relationships used to create the alignment. PILEUP uses a simplification of the progressive alignment method of Feng & Doolittle, 1987, *J. Mol. Evol.* 35:351-360; the method is similar to that described by Higgins and Sharp, 1989, CAB/OS 5:151-153. Useful PILEUP parameters including a default gap weight of 3.00, a default gap length weight of 0.10, and weighted end gaps.

Another example of a useful algorithm is the BLAST algorithm, described in: Altschul et al., 1990, *J. Mol. Biol.* 215:403-410; Altschul et al., 1997, *Nucleic Acids Res.* 25:3389-3402; and Karin et al., 1993, *Proc. Natl. Acad. Sci. U.S.A.* 90:5873-5787. A particularly useful BLAST program is the WU-BLAST-2 program which was obtained from Altschul et al., 1996, *Methods in Enzymology* 266:460-480. WU-BLAST-2 uses several search parameters, most of which are set to the default values. The adjustable parameters are set with the following values: overlap span=1, overlap fraction=0.125, word threshold (T)=II. The HSP S and HSP S2 parameters are dynamic values and are established by the program itself depending upon the composition of the particular sequence and composition of the particular database against which the sequence of interest is being searched; however, the values may be adjusted to increase sensitivity.

An additional useful algorithm is gapped BLAST as reported by Altschul et al., 1993, *Nucl. Acids Res.* 25:3389-3402. Gapped BLAST uses BLOSUM-62 substitution scores; threshold T parameter set to 9; the two-hit method to trigger ungapped extensions, charges gap lengths of k a cost of 10+k; Xu set to 16, and Xg set to 40 for database search stage and to 67 for the output stage of the algorithms. Gapped alignments are triggered by a score corresponding to about 22 bits.

Generally, the amino acid homology, similarity, or identity between individual variant CDRs or VH/VL sequences are at least 60% to the sequences depicted herein, and more typically with preferably increasing homologies or identities of at least 65% or 70%, more preferably at least 75% or 80%, even more preferably at least 85%, 90%, 91%, 92%, 93%, 94%, 95%, 96%, 97%, 98%, 99%, and almost 100%. In a similar manner, "percent (%) nucleic acid sequence identity"

with respect to the nucleic acid sequence of the binding proteins identified herein is defined as the percentage of nucleotide residues in a candidate sequence that are identical with the nucleotide residues in the coding sequence of the antibody construct. A specific method utilizes the BLASTN module of WU-BLAST-2 set to the default parameters, with overlap span and overlap fraction set to 1 and 0.125, respectively.

Generally, the nucleic acid sequence homology, similarity, or identity between the nucleotide sequences encoding individual variant CDRs or VH/VL sequences and the nucleotide sequences depicted herein are at least 60%, and more typically with preferably increasing homologies or identities of at least 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99%, and almost 100%. Thus, a "variant CDR" or a "variant VH/VL region" is one with the specified homology, similarity, or identity to the parent CDR/VH/VL of the invention, and shares biological function, including, but not limited to, at least 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98%, or 99% of the specificity and/or activity of the parent CDR or VH/VL.

In one embodiment, the percentage of identity to human germline of the antibody constructs according to the invention is ≥70% or ≥75%, more preferably ≥80% or ≥85%, even more preferably ≥90%, and most preferably ≥91%, ≥92%, ≥93%, ≥94%, ≥95% or even ≥96%. Identity to human antibody germline gene products is thought to be an important feature to reduce the risk of therapeutic proteins to elicit an immune response against the drug in the patient during treatment. Hwang & Foote ("Immunogenicity of engineered antibodies"; Methods 36 (2005) 3-10) demonstrate that the reduction of non-human portions of drug antibody constructs leads to a decrease of risk to induce anti-drug antibodies in the patients during treatment. By comparing an exhaustive number of clinically evaluated antibody drugs and the respective immunogenicity data, the trend is shown that humanization of the V-regions of antibodies makes the protein less immunogenic (average 5.1% of patients) than antibodies carrying unaltered non-human V regions (average 23.59% of patients). A higher degree of identity to human sequences is hence desirable for V-region based protein therapeutics in the form of antibody constructs. For this purpose of determining the germline identity, the V-regions of VL can be aligned with the amino acid sequences of human germline V segments and J segments (vbase.mrc-cpe.cam.ac.uk/) using Vector NTI software and the amino acid sequence calculated by dividing the identical amino acid residues by the total number of amino acid residues of the VL in percent. The same can be for the VH segments (vbase.mrc-cpe.cam.ac.uk/) with the exception that the VH CDR3 may be excluded due to its high diversity and a lack of existing human germline VH CDR3 alignment partners. Recombinant techniques can then be used to increase sequence identity to human antibody germline genes.

In a further embodiment, the bispecific antibody constructs of the present invention exhibit high monomer yields under standard research scale conditions, e.g., in a standard two-step purification process. Preferably the monomer yield of the antibody constructs according to the invention is ≥0.25 mg/L supernatant, more preferably ≥0.5 mg/L, even more preferably ≥1 mg/L, and most preferably ≥3 mg/L supernatant.

Likewise, the yield of the dimeric antibody construct isoforms and hence the monomer percentage (i.e., monomer: (monomer+dimer)) of the antibody constructs can be determined. The productivity of monomeric and dimeric antibody constructs and the calculated monomer percentage can e.g. be obtained in the SEC purification step of culture supernatant from standardized research-scale production in roller bottles. In one embodiment, the monomer percentage of the antibody constructs is ≥80%, more preferably ≥85%, even more preferably ≥90%, and most preferably ≥95%.

In one embodiment, the antibody constructs have a preferred plasma stability (ratio of EC50 with plasma to EC50 w/o plasma) of ≤5 or ≤4, more preferably ≤3.5 or ≤3, even more preferably ≤2.5 or ≤2, and most preferably ≤1.5 or ≤1. The plasma stability of an antibody construct can be tested by incubation of the construct in human plasma at 37° C. for 24 hours followed by EC50 determination in a [51]chromium release cytotoxicity assay. The effector cells in the cytotoxicity assay can be stimulated enriched human CD8 positive T cells. Target cells can e.g. be CHO cells transfected with the human target cell surface antigen. The effector to target cell (E:T) ratio can be chosen as 10:1. The human plasma pool used for this purpose is derived from the blood of healthy donors collected by EDTA coated syringes. Cellular components are removed by centrifugation and the upper plasma phase is collected and subsequently pooled. As control, antibody constructs are diluted immediately prior to the cytotoxicity assay in RPMI-1640 medium. The plasma stability is calculated as ratio of EC50 (after plasma incubation) to EC50 (control).

It is furthermore preferred that the monomer to dimer conversion of antibody constructs of the invention is low. The conversion can be measured under different conditions and analyzed by high performance size exclusion chromatography. For example, incubation of the monomeric isoforms of the antibody constructs can be carried out for 7 days at 37° C. and concentrations of e.g. 100 µg/ml or 250 µg/ml in an incubator. Under these conditions, it is preferred that the antibody constructs of the invention show a dimer percentage that is ≤55%, more preferably ≤4%, even more preferably ≤3%, even more preferably ≤2.5%, even more preferably ≤2%, even more preferably ≤1.5%, and most preferably ≤1% or ≤0.5% or even 0%.

It is also preferred that the bispecific antibody constructs of the present invention present with very low dimer conversion after a number of freeze/thaw cycles. For example, the antibody construct monomer is adjusted to a concentration of 250 µg/ml e.g. in generic formulation buffer and subjected to three freeze/thaw cycles (freezing at −80° C. for 30 min followed by thawing for 30 min at room temperature), followed by high performance SEC to determine the percentage of initially monomeric antibody construct, which had been converted into dimeric antibody construct. Preferably the dimer percentages of the bispecific antibody constructs are ≤5%, more preferably ≤4%, even more preferably ≤3%, even more preferably ≤2.5%, even more preferably ≤2%, even more preferably ≤1.5%, and most preferably ≤1% or even 50.5%, for example after three freeze/thaw cycles.

The bispecific antibody constructs of the present invention preferably show a favorable thermostability with aggregation temperatures ≥45° C. or ≥50° C., more preferably ≥52° C. or ≥54° C., even more preferably ≥56° C. or ≥57° C., and most preferably ≥58° C. or ≥59° C. The thermostability parameter can be determined in terms of antibody aggregation temperature as follows: Antibody solution at a concentration 250 µg/ml is transferred into a single use cuvette and placed in a Dynamic Light Scattering (DLS) device. The sample is heated from 40° C. to 70° C. at a heating rate of 0.5° C./min with constant acquisition of the measured radius. Increase of radius indicating melting of the protein and aggregation is used to calculate the aggregation temperature of the antibody.

Alternatively, temperature melting curves can be determined by Differential Scanning Calorimetry (DSC) to determine intrinsic biophysical protein stabilities of the antibody constructs. These experiments are performed using a MicroCal LLC (Northampton, MA, U.S.A) VP-DSC device. The energy uptake of a sample containing an antibody construct is recorded from 20° C. to 90° C. compared to a sample containing only the formulation buffer. The antibody constructs are adjusted to a final concentration of 250 µg/ml e.g. in SEC running buffer. For recording of the respective melting curve, the overall sample temperature is increased stepwise. At each temperature T energy uptake of the sample and the formulation buffer reference is recorded. The difference in energy uptake Cp (kcal/mole/° C.) of the sample minus the reference is plotted against the respective temperature. The melting temperature is defined as the temperature at the first maximum of energy uptake.

The target cell surface antigenxCD3 bispecific antibody constructs of the invention are also envisaged to have a turbidity (as measured by OD340 after concentration of purified monomeric antibody construct to 2.5 mg/ml and over night incubation) of ≤0.2, preferably of ≤0.15, more preferably of ≤0.12, even more preferably of ≤0.1, and most preferably of ≤0.08.

In a further embodiment the antibody construct according to the invention is stable at acidic pH. The more tolerant the antibody construct behaves at unphysiologic pH such as pH 5.5 (a pH which is required to run e.g. a cation exchange chromatography) or below, such as pH 4.0 to 5.5, the higher is the recovery of the antibody construct eluted from an ion exchange column relative to the total amount of loaded protein. Recovery of the antibody construct from an ion (e.g., cation) exchange column at pH 5.5 is preferably ≥30%, more preferably ≥40%, more preferably ≥50%, even more preferably ≥60%, even more preferably ≥70%, even more preferably ≥80%, even more preferably ≥90%, even more preferably ≥95%, and most preferably ≥99%.

It is furthermore envisaged that the bispecific antibody constructs of the present invention exhibit therapeutic efficacy or anti-tumor activity. This can e.g. be assessed in a study as disclosed in the following example of an advanced stage human tumor xenograft model:

The skilled person knows how to modify or adapt certain parameters of this study, such as the number of injected tumor cells, the site of injection, the number of transplanted human T cells, the amount of bispecific antibody constructs to be administered, and the timelines, while still arriving at a meaningful and reproducible result. Preferably, the tumor growth inhibition T/C [%] is ≤70 or ≤60, more preferably ≤50 or ≤40, even more preferably ≤30 or ≤20 and most preferably ≤10 or ≤5 or even ≤2.5.

In a preferred embodiment of the antibody construct of the invention the antibody construct is a single chain antibody construct.

Also in a preferred embodiment of the antibody construct of the invention said third domain comprises in an amino to carboxyl order:

> hinge-CH2-CH3-linker-hinge-CH2-CH3.

In one embodiment of the invention each of said polypeptide monomers of the third domain has an amino acid sequence that is at least 90% identical to a sequence selected from the group consisting of: SEQ ID NO: 17-24. In a preferred embodiment or the invention each of said polypeptide monomers has an amino acid sequence selected from SEQ ID NO: 17-24.

Also in one embodiment of the invention the CH2 domain of one or preferably each (both) polypeptide monomers of the third domain comprises an intra domain cysteine disulfide bridge. As known in the art the term "cysteine disulfide bridge" refers to a functional group with the general structure R—S—S—R. The linkage is also called an SS-bond or a disulfide bridge and is derived by the coupling of two thiol groups of cysteine residues. It is particularly preferred for the antibody construct of the invention that the cysteines forming the cysteine disulfide bridge in the mature antibody construct are introduced into the amino acid sequence of the CH2 domain corresponding to 309 and 321 (Kabat numbering).

In one embodiment of the invention a glycosylation site in Kabat position 314 of the CH2 domain is removed. It is preferred that this removal of the glycosylation site is achieved by a N314X substitution, wherein X is any amino acid excluding Q. Said substitution is preferably a N314G substitution. In a more preferred embodiment, said CH2 domain additionally comprises the following substitutions (position according to Kabat) V321C and R309C (these substitutions introduce the intra domain cysteine disulfide bridge at Kabat positions 309 and 321).

Figure 1:
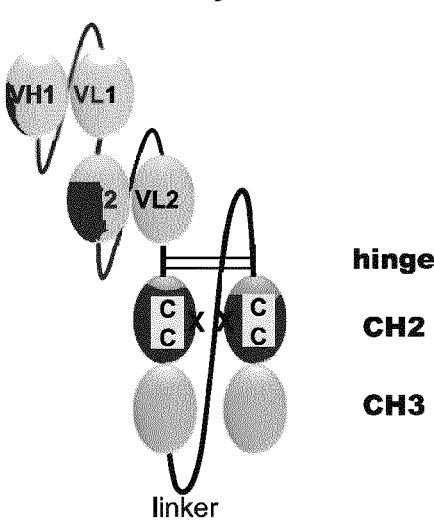
FIG. 1.
Figure 1:
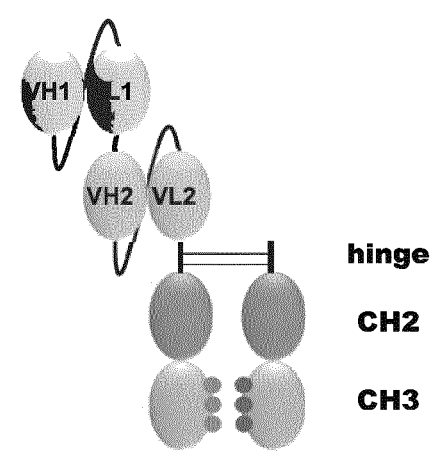
Figure 1:
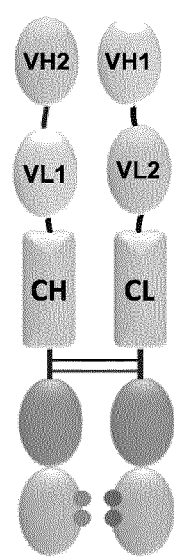
Figure 1:
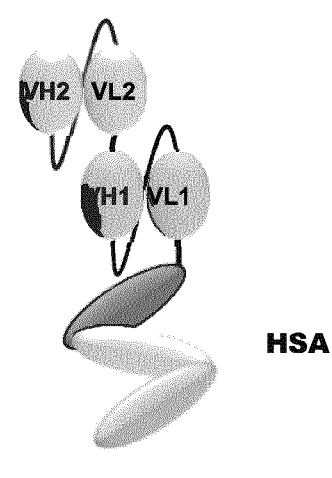

It is assumed that the preferred features of the antibody construct of the invention compared e.g. to the bispecific heteroFc antibody construct known in the art (FIG. 1b) may be inter *alia* related to the introduction of the above described modifications in the CH2 domain. Thus, it is preferred for the construct of the invention that the CH2 domains in the third domain of the antibody construct of the invention comprise the intra domain cysteine disulfide bridge at Kabat positions 309 and 321 and/or the glycosylation site at Kabat position 314 is removed by a N314X substitution as above, preferably by a N314G substitution.

In a further preferred embodiment of the invention the CH2 domains in the third domain of the antibody construct of the invention comprise the intra domain cysteine disulfide bridge at Kabat positions 309 and 321 and the glycosylation site at Kabat position 314 is removed by a N314G substitution. Most preferably, the polypeptide monomer of the third domain of the antibody construct of the invention has an amino acid sequence selected from the group consisting of SEQ ID NO: 17 and 18.

In one embodiment the invention provides an antibody construct, wherein:

(i) the first domain comprises two antibody variable domains and the second domain comprises two antibody variable domains;

(ii) the first domain comprises one antibody variable domain and the second domain comprises two antibody variable domains;

(iii) the first domain comprises two antibody variable domains and the second domain comprises one antibody variable domain; or (iv) the first domain comprises one antibody variable domain and the second domain comprises one antibody variable domain.

Accordingly, the first and the second domain may be binding domains comprising each two antibody variable domains such as a VH and a VL domain. Examples for such binding domains comprising two antibody variable domains where described herein above and comprise e.g. Fv fragments, scFv fragments or Fab fragments described herein above. Alternatively either one or both of those binding domains may comprise only a single variable domain. Examples for such single domain binding domains where described herein above and comprise e.g. nanobodies or single variable domain antibodies comprising merely one variable domain, which might be VHH, VH or VL, that specifically bind an antigen or epitope independently of other V regions or domains.

In a preferred embodiment of the antibody construct of the invention first and second domain are fused to the third domain via a peptide linker. Preferred peptide linker have been described herein above and are characterized by the amino acid sequence Gly-Gly-Gly-Gly-Ser, i.e. Gly$_4$Ser (SEQ ID NO: 1), or polymers thereof, i.e. (Gly$_4$Ser)x, where x is an integer of 1 or greater (e.g. 2 or 3). A particularly preferred linker for the fusion of the first and second domain to the third domain is depicted in SEQ ID NOs: 1.

In a preferred embodiment the antibody construct of the invention is characterized to comprise in an amino to carboxyl order:

(a) the first domain;

(b) a peptide linker having an amino acid sequence selected from the group consisting of SEQ ID NOs: 1-3;

(c) the second domain;

(d) a peptide linker having an amino acid sequence selected from the group consisting of SEQ ID NO: 1, 2, 3, 9, 10, 11 and 12;

(e) the first polypeptide monomer of the third domain;

(f) a peptide linker having an amino acid sequence selected from the group consisting of SEQ ID NOs: 5, 6, 7 and 8; and (g) the second polypeptide monomer of the third domain.

In one aspect of the invention the target cell surface antigen bound by the first domain is a tumor antigen, an antigen specific for an immunological disorder or a viral antigen. The term "tumor antigen" as used herein may be understood as those antigens that are presented on tumor cells. These antigens can be presented on the cell surface with an extracellular part, which is often combined with a transmembrane and cytoplasmic part of the molecule. These antigens can sometimes be presented only by tumor cells and never by the normal ones. Tumor antigens can be exclusively expressed on tumor cells or might represent a tumor specific mutation compared to normal cells. In this case, they are called tumor-specific antigens. More common are antigens that are presented by tumor cells and normal cells, and they are called tumor-associated antigens. These tumor-associated antigens can be overexpressed compared to normal cells or are accessible for antibody binding in tumor cells due to the less compact structure of the tumor tissue compared to normal tissue. Non-limiting examples of tumor antigens as used herein are CDH19, MSLN, DLL3, FLT3, EGFRvIII, CD33, CD19, CD20, and CD70.

In a preferred embodiment of the antibody construct of the invention the tumor antigen is selected from the group consisting of CDH19, MSLN, DLL3, FLT3, EGFRvIII, CD33, CD19, CD20, CD70, PSMA and BCMA.

In one aspect of the invention the antibody construct comprises in an amino to carboxyl order:

(a) the first domain having an amino acid sequence selected from the group consisting of SEQ ID NOs: 52, 70, 58, 76, 88, 106, 124, 94, 112, 130, 142,160, 178, 148, 166, 184, 196, 214, 232, 202, 220, 238, 250, 266, 282, 298, 255, 271, 287, 303, 322, 338, 354, 370, 386, 402, 418, 434, 450, 466, 482, 498, 514, 530, 546, 327, 343, 359, 375, 391, 407, 423, 439, 455, 471, 487, 503, 519, 353, 551, 592, 608, 624, 640, 656, 672, 688, 704, 720, 736, 752, 768, 784, 800, 816, 832, 848, 864, 880, 896, 912, 928, 944, 960, 976, 992, 1008, 1024, 1040, 1056, 1072, 1088, 1104, 1120, 1136, 1152, 1168, 1184, 597, 613, 629, 645, 661, 677, 693, 709, 725, 741, 757, 773, 789, 805, 821, 837, 853, 869, 885, 901, 917, 933, 949, 965, 981, 997, 1013, 1029, 1045, 1061, 1077, 1093, 1109, 1125, 1141, 1157, 1173, 1189, 1277, 1289, 1301, 1313, 1325, 1337, 1349, 1361, 1373, 1385, 1397, 1409, 1421, 1433, 1445; and selected from the sequenced directed against BCMA comprised in SEQ IDNOs 1460 to 1518; and 50, 56, 68, 74, 86, 92, 104, 110, 122, 128, 140, 146, 158, 164, 176, 182, 194, 200, 212, 218, 230, 236, 248, 254, 266, 272, 284, 290, 302, 308 related to PSMA wherein each of the foregoing SEQ ID Nos: 50 to 308 has to be subtracted by a value equal to 41 to obtain the corresponding number in the supplemental sequence table 12, and SEQ ID Nos 320, 335, 350, 365, 380, 395, 410, 425, 440, 455, and 470 related to PSMA in supplemental sequence table 12;

(b) a peptide linker having an amino acid sequence selected from the group consisting of SEQ ID NOs: 1-3;

(c) the second domain having an amino acid sequence selected from the group consisting of SEQ ID NOs: SEQ ID NOs: 23, 25, 41, 43, 59, 61, 77, 79, 95, 97, 113, 115, 131, 133, 149, 151, 167, 169, 185 or 187 of WO 2008/119567 or of SEQ ID NO: 15;

(d) a peptide linker having an amino acid sequence selected from the group consisting of SEQ ID NOs: 1, 2, 3, 9, 10, 11 and 12;

(e) the first polypeptide monomer of the third domain having a polypeptide sequence selected from the group consisting of SEQ ID NOs: 17-24;

(f) a peptide linker having an amino acid sequence selected from the group consisting of SEQ ID NOs: 5, 6, 7 and 8; and (g) the second polypeptide monomer of the third domain having a polypeptide sequence selected from the group consisting of SEQ ID NOs: 17-24.

In line with this preferred embodiment the first and second domain, which are fused via a peptide linker to a single chain polypeptide comprise a sequence selected from the group consisting of:

(a) SEQ ID NOs: 53 and 59; CD33

(b) SEQ ID NOs: 71 and 77; EGFRvIII (c) SEQ ID NOs:89, 107, 125, 95, 113, and 131; MSLN (d) SEQ ID NOs:143, 161, 179, 149, 167, and 185; CDH19

(e) SEQ ID NOs:197, 215, 233, 203, 221, and 239; DLL3

(f) SEQ ID NOs:251, 267, 283, 299, 256, 272, 288, and 304; CD19

(g) SEQ ID NOs:323, 339, 355, 371, 387, 403, 419, 435, 451, 467, 483, 499, 515, 531, 547, 328, 344, 360, 376, 392, 408, 424, 440, 456, 472, 488, 504, 520, 536, and 552; FLT3

(h) SEQ ID NOs:593, 609, 625, 641, 657, 673, 689, 705, 721, 737, 753, 769, 785, 801, 817, 833, 849, 865, 881, 897, 913, 929, 945, 961, 977, 993, 1009, 1025, 1041, 1057, 1073, 1089, 1105, 1121, 1137, 1153, 1169, 1185, 598, 614, 630, 646, 662, 678, 694, 710, 726, 742, 758, 774, 790, 806, 822, 838, 854, 870, 886, 902, 918, 934, 950, 966, 982, 998, 1014, 1030, 1046, 1062, 1078, 1094, 1110, 1126, 1142, 1158, 1174, and 1190; CD70

(i) SEQ ID NO: 1268; and CD20

(j) SEQ ID NOs: 1278, 1290, 1302, 1314, 1326, 1338, 1350, 1362, 1374, 1386, 1398, 1410, 1422, 1434, 1446. CD19

(k) respective sequences comprised in SEQ ID Nos: 1472, 1478, 1491, 1497, 1509, 1515 BCMA (l) SEQ ID NO: 1527, 1533, 1545, 1551, 1563, 1569, 1581, 1587, 1599, 1605, 1617, 1623, 1635, 1641, 1653, 1659, 1671, 1677, 1689, 1695, 1707, 1713, 1725, 1731, 1743, 1749, 1761 1767, 1779, 1785, 1797, 1812, 1827, 1842, 1857, 1872, 1887, 1902, 1917, 1927, 1937, 1947, 1962 PSMA In one aspect the antibody construct of the invention is characterized by having an amino acid sequence selected from the group consisting of:

(a) SEQ ID NOs: 54, 55, 60, and 61; CD33

(b) SEQ ID NOs: 72, 73, 78, and 79; EGFRvIII (c) SEQ ID NOs: 90, 91, 96, 97, 108, 109, 114, and 115; MSLN (d) SEQ ID NOs: 144, 145, 150, 151, 162, 163, 168, 169, 180, 181, 186, and 187; CDH19

(e) SEQ ID NOs: 198, 199, 204, 205, 216, 217, 222, 223, 234, 235, 240, and 241; DLL3

(f) SEQ ID NOs: 252, 306, 257, 307, 268, 308, 273, 309, 284, 310, 289, 311, 300, 312, 305, and 313; CD19

(g) SEQ ID NOs: 324, 554, 329, 555, 340, 556, 345, 557, 356, 558, 361, 559, 372, 560, 377, 561, 388, 562, 393, 563, 404, 564, 409, 565, 420, 566, 425, 567, 436, 568, 441, 569, 452, 570, 457, 571, 468, 572, 473, 573, 484, 574, 489, 575, 500, 576, 505, 577, 516, 578, 521, 579, 532, 580, 537, 581, 548, 582, 553, and 583; FLT3

(h) SEQ ID NOs: 594, 610, 626, 642, 658, 674, 690, 706, 722, 738, 754, 77, 786, 802, 818, 834, 850, 866, 882, 898, 914, 930, 946, 962, 978, 994, 1010, 1026, 1042, 1058, 1074, 1090, 1106, 1122, 1138, 1154, 1170, 1186, 599, 615, 631, 647, 663, 679, 695, 711, 727, 743, 759, 775, 791, 807, 823, 839, 855, 871, 887, 903, 919, 935, 951, 967, 983, 999, 1015, 1031, 1047, 1063, 1079, 1095, 1111, 1127, 1143, 1159, 1175, 1191, and 1192-1267; CD70

(i) SEQ ID NO: 43; CD20

(j) SEQ ID Nos: 1279, 1280, 1291, 1292, 1303, 1304, 1315, 1316, 1327, 1328, 1339, 1340, 1351, 1352, 1363, 1364, 1375, 1376, 1387, 1388, 1399, 1400, 1411, 1412, 1423, 1424, 1435, 1436, 1447, 1448. CD19

(k) SEQ ID Nos: 1473, 1474, 1475, 1479 1480, 1481, 1492, 1493, 1494, 1498, 1499, 1500, 1510, 1511, 1512, 1516, 1517, 1518 BCMA (l) 1528, 1529, 1530, 1534, 1535, 1536, 1546, 1547, 1548, 1552, 1553, 1554, 1564, 1565, 1566, 1570, 1571, 1572, 1582, 1583, 1584, 1588, 1589, 1590, 1600, 1601, 1602, 1606, 1607, 1608, 1618, 1619, 1620, 1624, 1625, 1626, 1636, 1637, 1638, 1642, 1643, 1644, 1654, 1655, 1656, 1660, 1661, 1662, 1672, 1673, 1674, 1678, 1679, 1680, 1690, 1691, 1692, 1696, 1697, 1698, 1708, 1709, 1710, 1714, 1715, 1716, 1726, 1727, 1728, 1732, 1733, 1734, 1744, 1745, 1746, 1750, 1751, 1752, 1762, 1763, 1764, 1768, 1769, 1770, 1774, 1775, 1776, 1786, 1787, 1788, 1798, 1799, 1800, 1801, 1802, 1803, 1813, 1814, 1815, 1816, 1817, 1818, 1828, 1829, 1830, 1831, 1832, 1833, 1843, 1844, 1845, 1846, 1847, 1848, 1858, 1859, 1860, 1861, 1862, 1863, 1873, 1874, 1875, 1876, 1877, 1878, 1888, 1889, 1890, 1891, 1892, 1893, 1903, 1904, 1905, 1906, 1907, 1908, 1918, 1919, 1920, 1921, 1922, 1923, 1933, 1934, 1935, 1936, 1937, 1938, 1948, 1949, 1950, 1951, 1952, 1953, and 1963 PSAM The invention further provides a polynucleotide/nucleic acid molecule encoding an antibody construct of the invention. A polynucleotide is a biopolymer composed of 13 or more nucleotide monomers covalently bonded in a chain. DNA (such as cDNA) and RNA (such as mRNA) are examples of polynucleotides with distinct biological function. Nucleotides are organic molecules that serve as the monomers or subunits of nucleic acid molecules like DNA or RNA. The nucleic acid molecule or polynucleotide can be double stranded and single stranded, linear and circular. It is preferably comprised in a vector which is preferably comprised in a host cell. Said host cell is, e.g. after transformation or transfection with the vector or the polynucleotide of the invention, capable of expressing the antibody construct. For that purpose the polynucleotide or nucleic acid molecule is operatively linked with control sequences.

The genetic code is the set of rules by which information encoded within genetic material (nucleic acids) is translated into proteins. Biological decoding in living cells is accomplished by the ribosome which links amino acids in an order specified by mRNA, using tRNA molecules to carry amino acids and to read the mRNA three nucleotides at a time. The code defines how sequences of these nucleotide triplets, called codons, specify which amino acid will be added next during protein synthesis. With some exceptions, a three-nucleotide codon in a nucleic acid sequence specifies a single amino acid. Because the vast majority of genes are encoded with exactly the same code, this particular code is often referred to as the canonical or standard genetic code. While the genetic code determines the protein sequence for a given coding region, other genomic regions can influence when and where these proteins are produced.

Furthermore, the invention provides a vector comprising a polynucleotide/nucleic acid molecule of the invention. A vector is a nucleic acid molecule used as a vehicle to transfer (foreign) genetic material into a cell. The term "vector" encompasses—but is not restricted to—plasmids, viruses, cosmids and artificial chromosomes. In general, engineered vectors comprise an origin of replication, a multicloning site and a selectable marker. The vector itself is generally a nucleotide sequence, commonly a DNA sequence that comprises an insert (transgene) and a larger sequence that serves as the "backbone" of the vector. Modern vectors may encompass additional features besides the transgene insert and a backbone: promoter, genetic marker, antibiotic resistance, reporter gene, targeting sequence, protein purification tag. Vectors called expression vectors (expression constructs) specifically are for the expression of the transgene in the target cell, and generally have control sequences.

The term "control sequences" refers to DNA sequences necessary for the expression of an operably linked coding sequence in a particular host organism. The control sequences that are suitable for prokaryotes, for example, include a promoter, optionally an operator sequence, and a ribosome binding side. Eukaryotic cells are known to utilize promoters, polyadenylation signals, and enhancers.

A nucleic acid is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding side is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

"Transfection" is the process of deliberately introducing nucleic acid molecules or polynucleotides (including vectors) into target cells. The term is mostly used for non-viral methods in eukaryotic cells. Transduction is often used to describe virus-mediated transfer of nucleic acid molecules or polynucleotides. Transfection of animal cells typically involves opening transient pores or "holes" in the cell membrane, to allow the uptake of material. Transfection can be carried out using calcium phosphate, by electroporation, by cell squeezing or by mixing a cationic lipid with the material to produce liposomes, which fuse with the cell membrane and deposit their cargo inside.

The term "transformation" is used to describe non-viral transfer of nucleic acid molecules or polynucleotides (including vectors) into bacteria, and also into non-animal eukaryotic cells, including plant cells. Transformation is hence the genetic alteration of a bacterial or non-animal eukaryotic cell resulting from the direct uptake through the cell membrane(s) from its surroundings and subsequent incorporation of exogenous genetic material (nucleic acid molecules). Transformation can be effected by artificial means. For transformation to happen, cells or bacteria must be in a state of competence, which might occur as a time-limited response to environmental conditions such as starvation and cell density.

Moreover, the invention provides a host cell transformed or transfected with the polynucleotide/nucleic acid molecule or with the vector of the invention. As used herein, the terms "host cell" or "recipient cell" are intended to include any individual cell or cell culture that can be or has/have been recipients of vectors, exogenous nucleic acid molecules, and polynucleotides encoding the antibody construct of the present invention; and/or recipients of the antibody construct itself. The introduction of the respective material into the cell is carried out by way of transformation, transfection and the like. The term "host cell" is also intended to include progeny or potential progeny of a single cell. Because certain modifications may occur in succeeding generations due to either natural, accidental, or deliberate mutation or due to environmental influences, such progeny may not, in fact, be completely identical (in morphology or in genomic or total DNA complement) to the parent cell, but is still included within the scope of the term as used herein. Suitable host cells include prokaryotic or eukaryotic cells, and also include but are not limited to bacteria, yeast cells, fungi cells, plant cells, and animal cells such as insect cells and mammalian cells, e.g., murine, rat, macaque or human.

The antibody construct of the invention can be produced in bacteria. After expression, the antibody construct of the invention is isolated from the *E. coli* cell paste in a soluble fraction and can be purified through, e.g., affinity chromatography and/or size exclusion. Final purification can be carried out similar to the process for purifying antibody expressed e.g., in CHO cells.

In addition to prokaryotes, eukaryotic microbes such as filamentous fungi or yeast are suitable cloning or expression hosts for the antibody construct of the invention. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe, Kluyveromyces* hosts such as *K. lactis, K. fragilis* (ATCC 12424), *K. Bulgaricus* (ATCC 16045), *K. wickeramii* (ATCC 24178), *K. waltii* (ATCC 56500), *K. drosophilarum* (ATCC 36906), *K. thermotolerans*, and *K. marxianus; yarrowia* (EP 402 226); *Pichia pastoris* (EP 183 070); *Candida; Trichoderma* reesia (EP 244 234); *Neurospora crassa; Schwanniomyces* such as *Schwanniomyces occidentalis*; and filamentous fungi such as *Neurospora, Penicillium, Tolypocladium*, and *Aspergillus* hosts such as *A. nidulans* and *A. niger.*

Suitable host cells for the expression of glycosylated antibody construct of the invention are derived from multicellular organisms. Examples of invertebrate cells include plant and insect cells. Numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruit fly), and *Bombyx mori* have been identified. A variety of viral strains for transfection are publicly available, e.g., the L-1 variant of *Autographa californica* NPV and the Bm-5 strain of *Bombyx mori* NPV, and such viruses may be used as the virus herein according to the present invention, particularly for transfection of *Spodoptera frugiperda* cells.

Plant cell cultures of cotton, corn, potato, soybean, *petunia*, tomato, *Arabidopsis* and tobacco can also be used as hosts. Cloning and expression vectors useful in the production of proteins in plant cell culture are known to those of skill in the art. See e.g. Hiatt et al., Nature (1989) 342: 76-78, Owen et al. (1992) Bio/Technology 10: 790-794, Artsaenko et al. (1995) The Plant J 8: 745-750, and Fecker et al. (1996) Plant Mol Biol 32: 979-986.

However, interest has been greatest in vertebrate cells, and propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36: 59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23: 243-251 (1980)); monkey kidney cells (CVI ATCC CCL 70); African green monkey kidney cells (VERO-76, ATCC CRL1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2,1413 8065); mouse mammary tumor (MMT 060562, ATCC CCL5 1); TRI cells (Mather et al., Annals N. Y Acad. Sci. (1982) 383: 44-68); MRC 5 cells; FS4 cells; and a human hepatoma line (Hep G2).

In a further embodiment the invention provides a process for the production of an antibody construct of the invention, said process comprising culturing a host cell of the invention under conditions allowing the expression of the antibody construct of the invention and recovering the produced antibody construct from the culture.

As used herein, the term "culturing" refers to the in vitro maintenance, differentiation, growth, proliferation and/or propagation of cells under suitable conditions in a medium. The term "expression" includes any step involved in the production of an antibody construct of the invention including, but not limited to, transcription, post-transcriptional modification, translation, post-translational modification, and secretion.

When using recombinant techniques, the antibody construct can be produced intracellularly, in the periplasmic space, or directly secreted into the medium. If the antibody construct is produced intracellularly, as a first step, the particulate debris, either host cells or lysed fragments, are removed, for example, by centrifugation or ultrafiltration. Carter et al., Bio/Technology 10: 163-167 (1992) describe a procedure for isolating antibodies which are secreted to the periplasmic space of *E. coli*. Briefly, cell paste is thawed in the presence of sodium acetate (pH 3.5), EDTA, and phenylmethylsulfonylfluoride (PMSF) over about 30 min. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants.

The antibody construct of the invention prepared from the host cells can be recovered or purified using, for example, hydroxylapatite chromatography, gel electrophoresis, dialysis, and affinity chromatography. Other techniques for protein purification such as fractionation on an ion-exchange column, ethanol precipitation, Reverse Phase HPLC, chromatography on silica, chromatography on heparin SEPHAROSE™, chromatography on an anion or cation exchange resin (such as a polyaspartic acid column), chromato-focusing, SDS-PAGE, and ammonium sulfate precipitation are also available depending on the antibody to be recovered. Where the antibody construct of the invention comprises a CH3 domain, the Bakerbond ABX resin (J. T. Baker, Phillipsburg, NJ) is useful for purification.

Affinity chromatography is a preferred purification technique. The matrix to which the affinity ligand is attached is most often agarose, but other matrices are available. Mechanically stable matrices such as controlled pore glass or poly (styrenedivinyl) benzene allow for faster flow rates and shorter processing times than can be achieved with agarose.

Moreover, the invention provides a pharmaceutical composition comprising an antibody construct of the invention or an antibody construct produced according to the process of the invention. It is preferred for the pharmaceutical composition of the invention that the homogeneity of the antibody construct is ≥80%, more preferably ≥81%, ≥82%, ≥83%, ≥84%, or ≥85%, further preferably ≥86%, ≥87%, ≥88%, ≥89%, or ≥90%, still further preferably, ≥91%, ≥92%, ≥93%, ≥94%, or ≥95% and most preferably ≥96%, ≥97%, ≥98% or ≥99%.

As used herein, the term "pharmaceutical composition" relates to a composition which is suitable for administration to a patient, preferably a human patient. The particularly preferred pharmaceutical composition of this invention comprises one or a plurality of the antibody construct(s) of the invention, preferably in a therapeutically effective amount. Preferably, the pharmaceutical composition further comprises suitable formulations of one or more (pharmaceutically effective) carriers, stabilizers, excipients, diluents, solubilizers, surfactants, emulsifiers, preservatives and/or adjuvants. Acceptable constituents of the composition are preferably nontoxic to recipients at the dosages and concentrations employed. Pharmaceutical compositions of the invention include, but are not limited to, liquid, frozen, and lyophilized compositions.

The inventive compositions may comprise a pharmaceutically acceptable carrier. In general, as used herein, "pharmaceutically acceptable carrier" means any and all aqueous and non-aqueous solutions, sterile solutions, solvents, buffers, e.g. phosphate buffered saline (PBS) solutions, water, suspensions, emulsions, such as oil/water emulsions, various types of wetting agents, liposomes, dispersion media and coatings, which are compatible with pharmaceutical administration, in particular with parenteral administration. The use of such media and agents in pharmaceutical compositions is well known in the art, and the compositions comprising such carriers can be formulated by well-known conventional methods.

Certain embodiments provide pharmaceutical compositions comprising the antibody construct of the invention and further one or more excipients such as those illustratively described in this section and elsewhere herein. Excipients can be used in the invention in this regard for a wide variety of purposes, such as adjusting physical, chemical, or biological properties of formulations, such as adjustment of viscosity, and or processes of the invention to improve effectiveness and or to stabilize such formulations and processes against degradation and spoilage due to, for instance, stresses that occur during manufacturing, shipping, storage, pre-use preparation, administration, and thereafter.

In certain embodiments, the pharmaceutical composition may contain formulation materials for the purpose of modifying, maintaining or preserving, e.g., the pH, osmolarity, viscosity, clarity, color, isotonicity, odor, sterility, stability, rate of dissolution or release, adsorption or penetration of the composition (see, REMINGTON'S PHARMACEUTICAL SCIENCES, 18" Edition, (A. R. Genrmo, ed.), 1990, Mack Publishing Company). In such embodiments, suitable formulation materials may include, but are not limited to:

amino acids such as glycine, alanine, glutamine, asparagine, threonine, proline, 2-phenylalanine, including charged amino acids, preferably lysine, lysine acetate, arginine, glutamate and/or histidine antimicrobials such as antibacterial and antifungal agents antioxidants such as ascorbic acid, methionine, sodium sulfite or sodium hydrogen-sulfite;

buffers, buffer systems and buffering agents which are used to maintain the composition at an acid pH of about 4.0 to 6.5, preferably 4.2 to 4.8; examples of buffers are borate, citrates, phosphates or other organic acids, succinate, phosphate, histidine and acetate; for example, or acetate buffer of about pH 4.0-5.5;

non-aqueous solvents such as propylene glycol, polyethylene glycol, vegetable oils such as olive oil, and injectable organic esters such as ethyl oleate;

aqueous carriers including water, alcoholic/aqueous solutions, emulsions or suspensions, including saline and buffered media;

biodegradable polymers such as polyesters;

bulking agents such as mannitol or glycine;

chelating agents such as ethylenediamine tetraacetic acid (EDTA);

isotonic and absorption delaying agents;

complexing agents such as caffeine, polyvinylpyrrolidone, beta-cyclodextrin or hydroxypropyl-beta-cyclodextrin)

fillers;

monosaccharides; disaccharides; and other carbohydrates (such as glucose, mannose or dextrins); carbohydrates may be non-reducing sugars, preferably trehalose, sucrose, octasulfate, sorbitol or xylitol;

(low molecular weight) proteins, polypeptides or proteinaceous carriers such as human or bovine serum albumin, gelatin or immunoglobulins, preferably of human origin;

coloring and flavouring agents;

sulfur containing reducing agents, such as glutathione, thioctic acid, sodium thioglycolate, thioglycerol, [alpha]-monothioglycerol, and sodium thio sulfate diluting agents;

emulsifying agents;

hydrophilic polymers such as polyvinylpyrrolidone)

salt-forming counter-ions such as sodium;

preservatives such as antimicrobials, anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide);

metal complexes such as Zn-protein complexes;

solvents and co-solvents (such as glycerin, propylene glycol or polyethylene glycol);

sugars and sugar alcohols, such as trehalose, sucrose, octasulfate, mannitol, sorbitol or xylitol stachyose, mannose, sorbose, xylose, ribose, myoinisitose, galactose, lactitol, ribitol, myoinisitol, galactitol, glycerol, cyclitols (e.g., inositol), polyethylene glycol; and polyhydric sugar alcohols;

suspending agents;

surfactants or wetting agents such as Pluronic®, PEG, sorbitan esters, polysorbates such as polysorbate 20, polysorbate, triton, tromethamine, lecithin, cholesterol, tyloxapal;

surfactants may be detergents, preferably with a molecular weight of >1.2 KD and/or a polyether, preferably with a molecular weight of >3 KD; non-limiting examples for preferred detergents are polysorbate 20, polysorbate 40, polysorbate 60, polysorbate 80 and polysorbate 85; non-limiting examples for preferred polyethers are PEG 3000, PEG 3350, PEG 4000 and PEG 5000;

stability enhancing agents such as sucrose or sorbitol;

tonicity enhancing agents such as alkali metal halides, preferably sodium or potassium chloride, mannitol sorbitol;

parenteral delivery vehicles including sodium chloride solution, Ringer's dextrose, dextrose and sodium chloride, lactated Ringer's, or fixed oils;

intravenous delivery vehicles including fluid and nutrient replenishers, electrolyte replenishers (such as those based on Ringer's dextrose).

It is evident to those skilled in the art that the different constituents of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

It is envisaged that the composition of the invention might comprise, in addition to the polypeptide of the invention defined herein, further biologically active agents, depending on the intended use of the composition. Such agents might be drugs acting on the gastro-intestinal system, drugs acting as cytostatica, drugs preventing hyperurikemia, drugs inhibiting immunoreactions (e.g. corticosteroids), drugs modulating the inflammatory response, drugs acting on the circulatory system and/or agents such as cytokines known in the art. It is also envisaged that the antibody construct of the present invention is applied in a co-therapy, i.e., in combination with another anti-cancer medicament.

In certain embodiments, the optimal pharmaceutical composition will be determined by one skilled in the art depending upon, for example, the intended route of administration, delivery format and desired dosage. See, for example, REMINGTON'S PHARMACEUTICAL SCIENCES, supra. In certain embodiments, such compositions may influence the physical state, stability, rate of in vivo release and rate of in vivo clearance of the antibody construct of the invention. In certain embodiments, the primary vehicle or carrier in a pharmaceutical composition may be either aqueous or non-aqueous in nature. For example, a suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles. In certain embodiments, the antibody construct of the invention compositions may be prepared for storage by mixing the selected composition having the desired degree of purity with optional formulation agents (REMINGTON'S PHARMACEUTICAL SCIENCES, supra) in the form of a lyophilized cake or an aqueous solution. Further, in certain embodiments, the antibody construct of the invention may be formulated as a lyophilizate using appropriate excipients such as sucrose.

When parenteral administration is contemplated, the therapeutic compositions for use in this invention may be provided in the form of a pyrogen-free, parenterally acceptable aqueous solution comprising the desired antibody construct of the invention in a pharmaceutically acceptable vehicle. A particularly suitable vehicle for parenteral injection is sterile distilled water in which the antibody construct of the invention is formulated as a sterile, isotonic solution, properly preserved. In certain embodiments, the preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. In certain embodiments, hyaluronic acid may also be used, having the effect of promoting sustained duration in the circulation. In certain embodiments, implantable drug delivery devices may be used to introduce the desired antibody construct.

Additional pharmaceutical compositions will be evident to those skilled in the art, including formulations involving the antibody construct of the invention in sustained- or controlled-delivery/release formulations. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, polylactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed. Mater. Res. 15:167-277 and Langer, 1982, Chem. Tech. 12:98-105), ethylene vinyl acetate (Langer et al., 1981, supra) or poly-D(−)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949.

The antibody construct may also be entrapped in microcapsules prepared, for example, by coacervation techniques or by interfacial polymerization (for example, hydroxymethylcellulose or gelatine-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 16th edition, Oslo, A., Ed., (1980).

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

Another aspect of the invention includes self-buffering antibody construct of the invention formulations, which can be used as pharmaceutical compositions, as described in international patent application WO 06138181A2 (PCT/US2006/022599). A variety of expositions are available on protein stabilization and formulation materials and methods useful in this regard, such as Arakawa et al., "Solvent interactions in pharmaceutical formulations," Pharm Res. 8(3): 285-91 (1991); Kendrick et al., "Physical stabilization of proteins in aqueous solution" in: RATIONAL DESIGN OF STABLE PROTEIN FORMULATIONS: THEORY AND PRACTICE, Carpenter and Manning, eds. Pharmaceutical Biotechnology. 13: 61-84 (2002), and Randolph et al., "Surfactant-protein interactions", Pharm Biotechnol. 13: 159-75 (2002), see particularly the parts pertinent to excipients and processes of the same for self-buffering protein formulations in accordance with the current invention, especially as to protein pharmaceutical products and processes for veterinary and/or human medical uses.

Salts may be used in accordance with certain embodiments of the invention to, for example, adjust the ionic strength and/or the isotonicity of a formulation and/or to improve the solubility and/or physical stability of a protein or other ingredient of a composition in accordance with the invention. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility.

Ionic species differ significantly in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic". Destabilizing solutes are referred to as "chaotropic". Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the antibody construct of the invention formulations in accordance with various embodiments of the invention as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Polyols are kosmotropic. They are useful stabilizing agents in both liquid and lyophilized formulations to protect proteins from physical and chemical degradation processes. Polyols also are useful for adjusting the tonicity of formulations. Among polyols useful in select embodiments of the invention is mannitol, commonly used to ensure structural stability of the cake in lyophilized formulations. It ensures structural stability to the cake. It is generally used with a lyoprotectant, e.g., sucrose. Sorbitol and sucrose are among preferred agents for adjusting tonicity and as stabilizers to protect against freeze-thaw stresses during transport or the preparation of bulks during the manufacturing process. Reducing sugars (which contain free aldehyde or ketone groups), such as glucose and lactose, can glycate surface lysine and arginine residues. Therefore, they generally are not among preferred polyols for use in accordance with the invention. In addition, sugars that form such reactive species, such as sucrose, which is hydrolyzed to fructose and glucose under acidic conditions, and consequently engenders glycation, also is not among preferred polyols of the invention in this regard. PEG is useful to stabilize proteins and as a cryoprotectant and can be used in the invention in this regard.

Embodiments of the antibody construct of the invention formulations further comprise surfactants. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Surfactants routinely are used to prevent, minimize, or reduce surface adsorption. Useful surfactants in the invention in this regard include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration. In this regard, polysorbates exemplify the general rule that excipients should be used in their lowest effective concentrations.

Embodiments of the antibody construct of the invention formulations further comprise one or more antioxidants. To some extent deleterious oxidation of proteins can be prevented in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations in accordance with the invention preferably are water-soluble and maintain their activity throughout the shelf life of a product. EDTA is a preferred antioxidant in accordance with the invention in this regard. Antioxidants can damage proteins. For instance, reducing agents, such as glutathione in particular, can disrupt intramolecular disulfide linkages. Thus, antioxidants for use in the invention are selected to, among other things, eliminate or sufficiently reduce the possibility of themselves damaging proteins in the formulation.

Formulations in accordance with the invention may include metal ions that are protein co-factors and that are necessary to form protein coordination complexes, such as zinc necessary to form certain insulin suspensions. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. $Ca^{+2}$ ions (up to 100 mM) can increase the stability of human deoxyribonuclease. $Mg^{+2}$, $Mn^{+2}$, and $Zn^{+2}$, however, can destabilize rhDNase. Similarly, $Ca^{+2}$ and $Sr^{+2}$ can stabilize Factor VIII, it can be destabilized by $Mg^{+2}$, $Mn^{+2}$ and $Zn^{+2}$, $Cu^{+2}$ and $Fe^{+2}$, and its aggregation can be increased by $Al^{+3}$ ions.

Embodiments of the antibody construct of the invention formulations further comprise one or more preservatives. Preservatives are necessary when developing multi-dose parenteral formulations that involve more than one extraction from the same container. Their primary function is to inhibit microbial growth and ensure product sterility throughout the shelf-life or term of use of the drug product. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in multi-dose protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations. At least four such pen devices containing preserved formulations of hGH are currently available on the market. Norditropin (liquid, Novo Nordisk), Nutropin AQ (liquid, Genentech) & Genotropin (lyophilized—dual chamber cartridge, Pharmacia & Upjohn) contain phenol while Somatrope (Eli Lilly) is formulated with m-cresol. Several aspects need to be considered during the formulation and development of preserved dosage forms. The effective preservative concentration in the drug product must be optimized. This requires testing a given preservative in the dosage form with concentration ranges that confer anti-microbial effectiveness without compromising protein stability.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544, 545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration.

The biological activity of the pharmaceutical composition defined herein can be determined for instance by cytotoxicity assays, as described in the following examples, in WO 99/54440 or by Schlereth et al. (Cancer Immunol. Immunother. 20 (2005), 1-12). "Efficacy" or "in vivo efficacy" as used herein refers to the response to therapy by the pharmaceutical composition of the invention, using e.g. standardized NCI response criteria. The success or in vivo efficacy of the therapy using a pharmaceutical composition of the invention refers to the effectiveness of the composition for its intended purpose, i.e. the ability of the composition to cause its desired effect, i.e. depletion of pathologic cells, e.g. tumor cells. The in vivo efficacy may be monitored by established standard methods for the respective disease entities including, but not limited to white blood cell counts, differentials, Fluorescence Activated Cell Sorting, bone marrow aspiration. In addition, various disease specific clinical chemistry parameters and other established standard methods may be used. Furthermore, computer-aided tomography, X-ray, nuclear magnetic resonance tomography (e.g. for National Cancer Institute-criteria based response assessment [Cheson B D, Horning S J, Coiffier B, Shipp M A, Fisher R I, Connors J M, Lister T A, Vose J, Grillo-Lopez A, Hagenbeek A, Cabanillas F, Klippensten D, Hiddemann W, Castellino R, Harris N L, Armitage J O, Carter W, Hoppe R, Canellos G P. Report of an international workshop to standardize response criteria for non-Hodgkin's lymphomas. NCI Sponsored International Working Group. J Clin Oncol. 1999 April; 17(4):1244]), positron-emission tomography scanning, white blood cell counts, differentials, Fluorescence Activated Cell Sorting, bone marrow aspiration, lymph node biopsies/histologies, and various lymphoma specific clinical chemistry parameters (e.g. lactate dehydrogenase) and other established standard methods may be used.

Another major challenge in the development of drugs such as the pharmaceutical composition of the invention is the predictable modulation of pharmacokinetic properties. To this end, a pharmacokinetic profile of the drug candidate, i.e. a profile of the pharmacokinetic parameters that affect the ability of a particular drug to treat a given condition, can be established. Pharmacokinetic parameters of the drug influencing the ability of a drug for treating a certain disease entity include, but are not limited to: half-life, volume of distribution, hepatic first-pass metabolism and the degree of blood serum binding. The efficacy of a given drug agent can be influenced by each of the parameters mentioned above.

"Half-life" means the time where 50% of an administered drug are eliminated through biological processes, e.g. metabolism, excretion, etc. By "hepatic first-pass metabolism" is meant the propensity of a drug to be metabolized upon first contact with the liver, i.e. during its first pass through the liver. "Volume of distribution" means the degree of retention of a drug throughout the various compartments of the body, like e.g. intracellular and extracellular spaces, tissues and organs, etc. and the distribution of the drug within these compartments. "Degree of blood serum binding" means the propensity of a drug to interact with and bind to blood serum proteins, such as albumin, leading to a reduction or loss of biological activity of the drug.

Pharmacokinetic parameters also include bioavailability, lag time (Tlag), Tmax, absorption rates, more onset and/or Cmax for a given amount of drug administered. "Bioavailability" means the amount of a drug in the blood compartment. "Lag time" means the time delay between the administration of the drug and its detection and measurability in blood or plasma. "Tmax" is the time after which maximal blood concentration of the drug is reached, and "Cmax" is the blood concentration maximally obtained with a given drug. The time to reach a blood or tissue concentration of the drug which is required for its biological effect is influenced by all parameters. Pharmacokinetic parameters of bispecific antibody constructs exhibiting cross-species specificity, which may be determined in preclinical animal testing in non-chimpanzee primates as outlined above, are also set forth e.g. in the publication by Schlereth et al. (Cancer Immunol. Immunother. 20 (2005), 1-12).

In a preferred aspect of the invention the pharmaceutical composition is stable for at least four weeks at about −20° C. As apparent from the appended examples the quality of an antibody construct of the invention vs. the quality of corresponding state of the art antibody constructs may be tested using different systems. Those tests are understood to be in line with the "ICH Harmonised Tripartite Guideline: *Stability Testing of Biotechnological/Biological Products Q5C and Specifications: Test procedures and Acceptance*

*Criteria for Biotech Biotechnological/Biological Products Q6B*" and, thus are elected to provide a stability-indicating profile that provides certainty that changes in the identity, purity and potency of the product are detected. It is well accepted that the term purity is a relative term. Due to the effect of glycosylation, deamidation, or other heterogeneities, the absolute purity of a biotechnological/biological product should be typically assessed by more than one method and the purity value derived is method-dependent. For the purpose of stability testing, tests for purity should focus on methods for determination of degradation products.

For the assessment of the quality of a pharmaceutical composition comprising an antibody construct of the invention may be analyzed e.g. by analyzing the content of soluble aggregates in a solution (HMWS per size exclusion). It is preferred that stability for at least four weeks at about −20° C. is characterized by a content of less than 1.5% HMWS, preferably by less than 1% HMWS.

Preferred formulations for the antibody construct as a pharmaceutical composition are laid out in detail above. However, the exact following formulations may be less preferred and are, thus, disclaimed:

Formulation A:

20 mM potassium phosphate, 150 mM L-arginine hydrochloride, 6% (w/V) trehalose dihydrate, 0.01% (w/V) polysorbate 80 at pH 6.0

Formulation B:

10 mM glutamate, 4% (w/V) mannitol, 2% (w/V) sucrose, 0.01% (w/V) polysorbate 80 at pH 4.0

Other examples for the assessment of the stability of an antibody construct of the invention in form of a pharmaceutical composition are provided in the appended examples 4-12. In those examples embodiments of antibody constructs of the invention are tested with respect to different stress conditions in different pharmaceutical formulations and the results compared with other half-life extending (HLE) formats of bispecific T cell engaging antibody construct known from the art. In general, it is envisaged that antibody constructs provided with the specific FC modality according to the present invention are typically more stable over a broad range of stress conditions such as temperature and light stress, both compared to antibody constructs provided with different HLE formats and without any HLE format (e.g. "canonical" antibody constructs). Said temperature stability may relate both to decreased (below room temperature including freezing) and increased (above room temperature including temperatures up to or above body temperature) temperature. As the person skilled in the art will acknowledge, such improved stability with regard to stress, which is hardly avoidable in clinical practice, makes the antibody construct safer because less degradation products will occur in clinical practice. In consequence, said increased stability means increased safety.

One embodiment provides the antibody construct of the invention or the antibody construct produced according to the process of the invention for use in the prevention, treatment or amelioration of a proliferative disease, a tumorous disease, a viral disease or an immunological disorder.

The formulations described herein are useful as pharmaceutical compositions in the treatment, amelioration and/or prevention of the pathological medical condition as described herein in a patient in need thereof. The term "treatment" refers to both therapeutic treatment and prophylactic or preventative measures. Treatment includes the application or administration of the formulation to the body, an isolated tissue, or cell from a patient who has a disease/disorder, a symptom of a disease/disorder, or a predisposition toward a disease/disorder, with the purpose to cure, heal, alleviate, relieve, alter, remedy, ameliorate, improve, or affect the disease, the symptom of the disease, or the predisposition toward the disease.

The term "amelioration" as used herein refers to any improvement of the disease state of a patient having a tumor or cancer or a metastatic cancer as specified herein below, by the administration of an antibody construct according to the invention to a subject in need thereof. Such an improvement may also be seen as a slowing or stopping of the progression of the tumor or cancer or metastatic cancer of the patient. The term "prevention" as used herein means the avoidance of the occurrence or re-occurrence of a patient having a tumor or cancer or a metastatic cancer as specified herein below, by the administration of an antibody construct according to the invention to a subject in need thereof.

The term "disease" refers to any condition that would benefit from treatment with the antibody construct or the pharmaceutic composition described herein. This includes chronic and acute disorders or diseases including those pathological conditions that predispose the mammal to the disease in question.

A "neoplasm" is an abnormal growth of tissue, usually but not always forming a mass. When also forming a mass, it is commonly referred to as a "tumor". Neoplasms or tumors or can be benign, potentially malignant (pre-cancerous), or malignant. Malignant neoplasms are commonly called cancer. They usually invade and destroy the surrounding tissue and may form metastases, i.e., they spread to other parts, tissues or organs of the body. Hence, the term "metatstatic cancer" encompasses metastases to other tissues or organs than the one of the original tumor. Lymphomas and leukemias are lymphoid neoplasms. For the purposes of the present invention, they are also encompassed by the terms "tumor" or "cancer".

The term "viral disease" describes diseases, which are the result of a viral infection of a subject.

The term "immunological disorder" as used herein describes in line with the common definition of this term immunological disorders such as autoimmune diseases, hypersensitivities, immune deficiencies.

In one embodiment the invention provides a method for the treatment or amelioration of a proliferative disease, a tumorous disease, a viral disease or an immunological disorder, comprising the step of administering to a subject in need thereof the antibody construct of the invention, or produced according to the process of the invention.

The terms "subject in need" or those "in need of treatment" includes those already with the disorder, as well as those in which the disorder is to be prevented. The subject in need or "patient" includes human and other mammalian subjects that receive either prophylactic or therapeutic treatment.

The antibody construct of the invention will generally be designed for specific routes and methods of administration, for specific dosages and frequencies of administration, for specific treatments of specific diseases, with ranges of bio-availability and persistence, among other things. The materials of the composition are preferably formulated in concentrations that are acceptable for the site of administration.

Formulations and compositions thus may be designed in accordance with the invention for delivery by any suitable route of administration. In the context of the present invention, the routes of administration include, but are not limited to topical routes (such as epicutaneous, inhalational, nasal, opthalmic, auricular/aural, vaginal, mucosal);

enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions and the antibody construct of this invention are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447,233; 4,486,194; 4,487,603; 4,596,556; 4,790,824; 4,941,880; 5,064,413; 5,312,335; 5,312,335; 5,383,851; and 5,399,163.

In particular, the present invention provides for an uninterrupted administration of the suitable composition. As a non-limiting example, uninterrupted or substantially uninterrupted, i.e. continuous administration may be realized by a small pump system worn by the patient for metering the influx of therapeutic agent into the body of the patient. The pharmaceutical composition comprising the antibody construct of the invention can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the antibody constructs of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

The continuous administration may also be transdermal by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

If the pharmaceutical composition has been lyophilized, the lyophilized material is first reconstituted in an appropriate liquid prior to administration. The lyophilized material may be reconstituted in, e.g., bacteriostatic water for injection (BWFI), physiological saline, phosphate buffered saline (PBS), or the same formulation the protein had been in prior to lyophilization.

The compositions of the present invention can be administered to the subject at a suitable dose which can be determined e.g. by dose escalating studies by administration of increasing doses of the antibody construct of the invention exhibiting cross-species specificity described herein to non-chimpanzee primates, for instance macaques. As set forth above, the antibody construct of the invention exhibiting cross-species specificity described herein can be advantageously used in identical form in preclinical testing in non-chimpanzee primates and as drug in humans. The dosage regimen will be determined by the attending physician and clinical factors. As is well known in the medical arts, dosages for any one patient depend upon many factors, including the patient's size, body surface area, age, the particular compound to be administered, sex, time and route of administration, general health, and other drugs being administered concurrently.

The term "effective dose" or "effective dosage" is defined as an amount sufficient to achieve or at least partially achieve the desired effect. The term "therapeutically effective dose" is defined as an amount sufficient to cure or at least partially arrest the disease and its complications in a patient already suffering from the disease. Amounts or doses effective for this use will depend on the condition to be treated (the indication), the delivered antibody construct, the therapeutic context and objectives, the severity of the disease, prior therapy, the patient's clinical history and response to the therapeutic agent, the route of administration, the size (body weight, body surface or organ size) and/or condition (the age and general health) of the patient, and the general state of the patient's own immune system. The proper dose can be adjusted according to the judgment of the attending physician such that it can be administered to the patient once or over a series of administrations, and in order to obtain the optimal therapeutic effect.

A typical dosage may range from about 0.1 µg/kg to up to about 30 mg/kg or more, depending on the factors mentioned above. In specific embodiments, the dosage may range from 1.0 µg/kg up to about 20 mg/kg, optionally from 10 µg/kg up to about 10 mg/kg or from 100 µg/kg up to about 5 mg/kg.

A therapeutic effective amount of an antibody construct of the invention preferably results in a decrease in severity of disease symptoms, an increase in frequency or duration of disease symptom-free periods or a prevention of impairment or disability due to the disease affliction. For treating target cell antigen-expressing tumors, a therapeutically effective amount of the antibody construct of the invention, e.g. an anti-target cell antigen/anti-CD3 antibody construct, preferably inhibits cell growth or tumor growth by at least about 20%, at least about 40%, at least about 50%, at least about 60%, at least about 70%, at least about 80%, or at least about 90% relative to untreated patients. The ability of a compound to inhibit tumor growth may be evaluated in an animal model predictive of efficacy The pharmaceutical composition can be administered as a sole therapeutic or in combination with additional therapies such as anti-cancer therapies as needed, e.g. other proteinaceous and non-proteinaceous drugs. These drugs may be administered simultaneously with the composition comprising the antibody construct of the invention as defined herein or separately before or after administration of said antibody construct in timely defined intervals and doses.

The term "effective and non-toxic dose" as used herein refers to a tolerable dose of an inventive antibody construct which is high enough to cause depletion of pathologic cells, tumor elimination, tumor shrinkage or stabilization of disease without or essentially without major toxic effects. Such effective and non-toxic doses may be determined e.g. by dose escalation studies described in the art and should be below the dose inducing severe adverse side events (dose limiting toxicity, DLT).

The term "toxicity" as used herein refers to the toxic effects of a drug manifested in adverse events or severe adverse events. These side events might refer to a lack of tolerability of the drug in general and/or a lack of local tolerance after administration. Toxicity could also include teratogenic or carcinogenic effects caused by the drug.

The term "safety", "in vivo safety" or "tolerability" as used herein defines the administration of a drug without inducing severe adverse events directly after administration (local tolerance) and during a longer period of application of the drug. "Safety", "in vivo safety" or "tolerability" can be evaluated e.g. at regular intervals during the treatment and follow-up period. Measurements include clinical evaluation, e.g. organ manifestations, and screening of laboratory abnormalities. Clinical evaluation may be carried out and deviations to normal findings recorded/coded according to NCI-CTC and/or MedDRA standards. Organ manifestations may include criteria such as allergy/immunology, blood/bone marrow, cardiac arrhythmia, coagulation and the like, as set forth e.g. in the Common Terminology Criteria for adverse events v3.0 (CTCAE). Laboratory parameters which may be tested include for instance hematology, clinical chemistry, coagulation profile and urine analysis and examination of other body fluids such as serum, plasma, lymphoid or spinal fluid, liquor and the like. Safety can thus be assessed e.g. by physical examination, imaging techniques (i.e. ultrasound, x-ray, CT scans, Magnetic Resonance Imaging (MRI), other measures with technical devices (i.e. electrocardiogram), vital signs, by measuring laboratory parameters and recording adverse events. For example, adverse events in non-chimpanzee primates in the uses and methods according to the invention may be examined by histopathological and/or histochemical methods.

The above terms are also referred to e.g. in the Preclinical safety evaluation of biotechnology-derived pharmaceuticals S6; ICH Harmonised Tripartite Guideline; ICH Steering Committee meeting on Jul. 16, 1997.

Finally, the invention provides a kit comprising an antibody construct of the invention or produced according to the process of the invention, a pharmaceutical composition of the invention, a polynucleotide of the invention, a vector of the invention and/or a host cell of the invention.

In the context of the present invention, the term "kit" means two or more components—one of which corresponding to the antibody construct, the pharmaceutical composition, the vector or the host cell of the invention—packaged together in a container, recipient or otherwise. A kit can hence be described as a set of products and/or utensils that are sufficient to achieve a certain goal, which can be marketed as a single unit.

The kit may comprise one or more recipients (such as vials, ampoules, containers, syringes, bottles, bags) of any appropriate shape, size and material (preferably waterproof, e.g. plastic or glass) containing the antibody construct or the pharmaceutical composition of the present invention in an appropriate dosage for administration (see above). The kit may additionally contain directions for use (e.g. in the form of a leaflet or instruction manual), means for administering the antibody construct of the present invention such as a syringe, pump, infuser or the like, means for reconstituting the antibody construct of the invention and/or means for diluting the antibody construct of the invention.

The invention also provides kits for a single-dose administration unit. The kit of the invention may also contain a first recipient comprising a dried/lyophilized antibody construct and a second recipient comprising an aqueous formulation. In certain embodiments of this invention, kits containing single-chambered and multi-chambered pre-filled syringes (e.g., liquid syringes and lyosyringes) are provided.

The pharmaceutical composition of the invention further comprises a buffer, which may be selected from the group consisting of potassium phosphate, acetic acid/sodium acetate, citric acid/sodium citrate, succinic acid/sodium succinate, tartaric acid/sodium tartrate, histidine/histidine HCl, glycine, tris(hydroxymethyl)aminomethane, glutamate, acetate and mixtures thereof, and in particular from potassium phosphate, citric acid/sodium citrate, succinic acid, histidine, glutamate, acetate and combinations thereof.

Suitable buffer concentrations encompass concentrations of about 200 mM or less, such as about 190, 180, 170, 160, 150, 140, 130,120, 110, 100, 80, 70, 60, 50, 40, 30, 20, 10 or 5 mM. The skilled person will be readily able to adjust the buffer concentrations in order to provide for stability of the pharmaceutical composition as described herein. Envisaged buffer concentrations in the pharmaceutical composition of the invention specifically range from about 5 to about 200 mM, preferably from about 5 to about 100 mM, and more preferably from about 10 to about 50 mM.

As used herein, the term "pharmaceutical composition" relates to a composition which is suitable for administration to a subject in need thereof. The terms "subject" or "individual" or "animal" or "patient" are used interchangeably herein to refer to any subject, particularly a mammalian subject, for whom administration of the pharmaceutical composition of the invention is desired. Mammalian subjects include humans, non-human primates, dogs, cats, guinea pigs, rabbits, rats, mice, horses, cattle, cows, and the like, with humans being preferred. The pharmaceutical composition of the present invention is stable and pharmaceutically acceptable, i.e. capable of eliciting the desired therapeutic effect without causing any undesirable local or systemic effects in the subject to which the pharmaceutical composition is administered. Pharmaceutically acceptable compositions of the invention may in particular be sterile and/or pharmaceutically inert. Specifically, the term "pharmaceutically acceptable" can mean approved by a regulatory agency or other generally recognized pharmacopoeia for use in animals, and more particularly in humans.

The pharmaceutical composition of the invention comprises one or a plurality of the bispecific single chain antibody construct(s) described herein, preferably in a therapeutically effective amount, a β-cyclodextrin and a buffer. By "therapeutically effective amount" is meant an amount of said construct that elicits the desired therapeutic effect. Therapeutic efficacy and toxicity can be determined by standard pharmaceutical procedures in cell cultures or experimental animals, e.g., ED50 (the dose therapeutically effective in 50% of the population) and LD50 (the dose lethal to 50% of the population). The dose ratio between therapeutic and toxic effects is the therapeutic index, and it can be expressed as the ratio, ED50/LD50. Pharmaceutical compositions that exhibit large therapeutic indices are generally preferred.

The composition may comprise a @-cyclodextrin and the buffer described previously. The pharmaceutical composition may optionally comprise one or more further excipients as long as they do not reduce or abolish its advantageous properties as described herein, and in particular its stability.

Excipients can be used in the invention for a wide variety of purposes, such as adjusting physical, chemical, or biological properties of formulations, such as adjustment of viscosity, and or processes of the invention to further improve effectiveness and or to further stabilize such formulations and processes against degradation and spoilage due to, for instance, stresses that occur during manufacturing, shipping, storage, pre-use preparation, administration, and thereafter. The term "excipient" generally includes fillers, binders, disintegrants, coatings, sorbents, antiadherents, glidants, preservatives, antioxidants, flavoring, coloring, sweeting agents, solvents, co-solvents, buffering agents, chelating agents, viscosity imparting agents, surface active agents, diluents, humectants, carriers, diluents, preservatives, emulsifiers, stabilizers and tonicity modifiers.

It is evident to those skilled in the art that the different excipients of the pharmaceutical composition (e.g., those listed above) can have different effects, for example, and amino acid can act as a buffer, a stabilizer and/or an antioxidant; mannitol can act as a bulking agent and/or a tonicity enhancing agent; sodium chloride can act as delivery vehicle and/or tonicity enhancing agent; etc.

Polyols are useful stabilizing agents in both liquid and lyophilized formulations to protect proteins from physical and chemical degradation processes, and are also useful for adjusting the tonicity of formulations. Polyols include sugars, e.g., mannitol, sucrose, and sorbitol and polyhydric alcohols such as, for instance, glycerol and propylene glycol, and, for purposes of discussion herein, polyethylene glycol (PEG) and related substances. Mannitol is commonly used to ensure structural stability of the cake in lyophilized formulations. It ensures structural stability to the cake. It is generally used with a lyoprotectant, e.g., sucrose. Sorbitol and sucrose are commonly used agents for adjusting tonicity and as stabilizers to protect against freeze-thaw stresses during transport or the preparation of bulks during the manufacturing process. PEG is useful to stabilize proteins and as a cryoprotectant.

Surfactants routinely are used to prevent, minimize, or reduce surface adsorption. Protein molecules may be susceptible to adsorption on surfaces and to denaturation and consequent aggregation at air-liquid, solid-liquid, and liquid-liquid interfaces. These effects generally scale inversely with protein concentration. These deleterious interactions generally scale inversely with protein concentration and typically are exacerbated by physical agitation, such as that generated during the shipping and handling of a product. Commonly used surfactants include polysorbate 20, polysorbate 80, other fatty acid esters of sorbitan polyethoxylates, and poloxamer 188. Surfactants also are commonly used to control protein conformational stability. The use of surfactants in this regard is protein-specific since, any given surfactant typically will stabilize some proteins and destabilize others.

Polysorbates are susceptible to oxidative degradation and often, as supplied, contain sufficient quantities of peroxides to cause oxidation of protein residue side-chains, especially methionine. Consequently, polysorbates should be used carefully, and when used, should be employed at their lowest effective concentration.

Antioxidants can—to some extent—prevent deleterious oxidation of proteins in pharmaceutical formulations by maintaining proper levels of ambient oxygen and temperature and by avoiding exposure to light. Antioxidant excipients can be used as well to prevent oxidative degradation of proteins. Among useful antioxidants in this regard are reducing agents, oxygen/free-radical scavengers, and chelating agents. Antioxidants for use in therapeutic protein formulations are preferably water-soluble and maintain their activity throughout the shelf life of a product. EDTA is a useful example.

Metal ions can act as protein co-factors and enable the formation of protein coordination complexes. Metal ions also can inhibit some processes that degrade proteins. However, metal ions also catalyze physical and chemical processes that degrade proteins. Magnesium ions (10-120 mM) can be used to inhibit isomerization of aspartic acid to isoaspartic acid. $Ca+2$ ions (up to 100 mM) can increase the stability of human deoxyribonuclease. $Mg+2$, $Mn+2$, and $Zn+2$, however, can destabilize rhDNase. Similarly, $Ca+2$ and $Sr+2$ can stabilize Factor VIII, it can be destabilized by $Mg+2$, $Mn+2$ and $Zn+2$, $Cu+2$ and $Fe+2$, and its aggregation can be increased by $Al+3$ ions.

Preservatives have the primary function to inhibit microbial growth and ensure product sterility throughout the shelf-life or term of use of the drug product, and are in particular needed for multi-dose formulations. Commonly used preservatives include benzyl alcohol, phenol and m-cresol. Although preservatives have a long history of use with small-molecule parenterals, the development of protein formulations that includes preservatives can be challenging. Preservatives almost always have a destabilizing effect (aggregation) on proteins, and this has become a major factor in limiting their use in protein formulations. To date, most protein drugs have been formulated for single-use only. However, when multi-dose formulations are possible, they have the added advantage of enabling patient convenience, and increased marketability. A good example is that of human growth hormone (hGH) where the development of preserved formulations has led to commercialization of more convenient, multi-use injection pen presentations.

As might be expected, development of liquid formulations containing preservatives are more challenging than lyophilized formulations. Freeze-dried products can be lyophilized without the preservative and reconstituted with a preservative containing diluent at the time of use. This shortens the time for which a preservative is in contact with the protein, significantly minimizing the associated stability risks. With liquid formulations, preservative effectiveness and stability should be maintained over the entire product shelf-life (about 18 to 24 months). An important point to note is that preservative effectiveness should be demonstrated in the final formulation containing the active drug and all excipient components.

Salts may be used in accordance with the invention to, for example, adjust the ionic strength and/or the isotonicity of the pharmaceutical formulation and/or to further improve the solubility and/or physical stability of the antibody construct or other ingredient. As is well known, ions can stabilize the native state of proteins by binding to charged residues on the protein's surface and by shielding charged and polar groups in the protein and reducing the strength of their electrostatic interactions, attractive, and repulsive interactions. Ions also can stabilize the denatured state of a protein by binding to, in particular, the denatured peptide linkages (—CONH) of the protein. Furthermore, ionic interaction with charged and polar groups in a protein also can reduce intermolecular electrostatic interactions and, thereby, prevent or reduce protein aggregation and insolubility. Ionic species differ in their effects on proteins. A number of categorical rankings of ions and their effects on proteins have been developed that can be used in formulating pharmaceutical compositions in accordance with the invention. One example is the Hofmeister series, which ranks ionic and polar non-ionic solutes by their effect on the conformational stability of proteins in solution. Stabilizing solutes are referred to as "kosmotropic." Destabilizing solutes are referred to as "chaotropic." Kosmotropes commonly are used at high concentrations (e.g., >1 molar ammonium sulfate) to precipitate proteins from solution ("salting-out"). Chaotropes commonly are used to denture and/or to solubilize proteins ("salting-in"). The relative effectiveness of ions to "salt-in" and "salt-out" defines their position in the Hofmeister series.

Free amino acids can be used in the pharmaceutical composition as bulking agents, stabilizers, and antioxidants, as well as other standard uses. Lysine, proline, serine, and alanine can be used for stabilizing proteins in a formulation. Glycine is useful in lyophilization to ensure correct cake structure and properties. Arginine may be useful to inhibit protein aggregation, in both liquid and lyophilized formulations. Methionine is useful as an antioxidant.

Particularly useful excipients for formulating the pharmaceutical composition include sucrose, trehalose, mannitol, sorbitol, arginine, lysine, polysorbate 20, polysorbate 80, poloxamer 188, Pluronic® and combinations thereof. Said excipients may be present in the pharmaceutical composition in different concentrations, as long as the composition exhibits the desirable properties as exemplified herein, and in particular promotes stabilization of the contained bispecific single chain antibody constructs. For instance, sucrose may be present in the pharmaceutical composition in a concentration between 2% (w/v) and 12% (w/v), i.e. in a concentration of 12% (w/v), 11% (w/v), 10% (w/v), 9% (w/v), 8% (w/v), 7% (w/v), 6% (w/v), 5% (w/v), 4% (w/v), 3% (w/v) or 2% (w/v). Preferred sucrose concentrations range between 4% (w/v) and 10% (w/v) and more preferably between 6% (w/v) and 10% (w/v). Polysorbate 80 may be present in the pharmaceutical composition in a concentration between 0.001% (w/v) and 0.5% (w/v), i.e. in a concentration of 0.5% (w/v), 0.2% (w/v), 0.1% (w/v), 0.08% (w/v), 0.05% (w/v), 0.02% (w/v), 0.01% (w/v), 0.008% (w/v), 0.005% (w/v), 0.002% (w/v) or 0.001% (w/v). Preferred Polysorbate 80 concentrations range between 0.002% (w/v) and 0.5% (w/v), and preferably between 0.005% (w/v) and 0.02% (w/v).

Useful preservatives for formulating pharmaceutical compositions generally include antimicrobials (e.g. anti-bacterial or anti-fungal agents), anti-oxidants, chelating agents, inert gases and the like; examples are: benzalkonium chloride, benzoic acid, salicylic acid, thimerosal, phenethyl alcohol, methylparaben, propylparaben, chlorhexidine, sorbic acid or hydrogen peroxide). Antimicrobial preservatives are substances which are used to extend the shelf-life of medicines by reducing microbial proliferation. Preservatives that particularly useful for formulating the pharmaceutical composition of the invention include benzyl alcohol, chlorobutanol, phenol, meta-cresol, methylparaben, phenoxyethanol, propylparaben thiomerosal. The structure and typical concentration for the use of these preservatives are described in Table 1 of Meyer et al. J Pharm Sci. 96(12), 3155.

The aforementioned preservatives may be present in the pharmaceutical composition in different concentrations. For instance, benzyl alcohol may be present in a concentration ranging between 0.2 and 1.1% (v/v), chlorobutanol in a concentration ranging between 0.3-0.5% (v/v), phenol in a concentration ranging between 0.07 and 0.5% (v/v), meta-cresol in a concentration ranging between 0.17 and 0-32% (v/v) or thiomerosal in a concentration ranging between 0.003 to 0.01% (v/v). Preferred concentrations for meth-ylparaben are in the range of 0.05 and 0.5% (v/v), for phenoxyethanol in the range of 0.1 and 3% (v/v) and for propylparaben in the range of 0.05 and 0.5% (v/v).

However, it is also conceivable that the pharmaceutical composition does not comprise any preservatives. In particular, the present invention inter alia provides a pharmaceutical composition being free of preservatives, comprising a bispecific single chain antibody construct in a concentration of about 0.5 mg/ml, sulfobutylether-s-cyclodextrin sodium salt in a concentration of about 1% (w/v), and potassium phosphate in concentration of about 10 mM, and further sucrose in concentration of about 8% (w/v) of and polysorbate 80 in concentration of about 0.01% (w/v) at a pH of about 6.0.

The pharmaceutical compositions of the invention can be formulated in various forms, e.g. in solid, liquid, frozen, gaseous or lyophilized form and may be, inter alia, in the form of an ointment, a cream, transdermal patches, a gel, powder, a tablet, solution, an aerosol, granules, pills, suspensions, emulsions, capsules, syrups, liquids, elixirs, extracts, tincture or fluid extracts.

Generally, various storage and/or dosage forms are conceivable for the pharmaceutical composition of the invention, depending, i.a., on the intended route of administration, delivery format and desired dosage (see, for example, Remington's Pharmaceutical Sciences, 22nd edition, Oslo, A., Ed., (2012)). The skilled person will be aware that such choice of a particular dosage form may for example influence the physical state, stability, rate of in vivo release and rate of in vivo clearance of the antibody construct of the invention.

For instance, the primary vehicle or carrier in a pharmaceutical composition may be either aqueous or non-aqueous in nature. A suitable vehicle or carrier may be water for injection, physiological saline solution or artificial cerebrospinal fluid, possibly supplemented with other materials common in compositions for parenteral administration. Neutral buffered saline or saline mixed with serum albumin are further exemplary vehicles.

When parenteral administration is contemplated, the therapeutic compositions of the invention may be provided in the form of a pyrogen-free, parenterally acceptable aqueous solution comprising the desired antibody construct in a pharmaceutically acceptable vehicle. A particularly suitable vehicle for parenteral injection is sterile distilled water in which the antibody construct is formulated as a sterile, isotonic solution, properly preserved. The preparation can involve the formulation of the desired molecule with an agent, such as injectable microspheres, bio-erodible particles, polymeric compounds (such as polylactic acid or polyglycolic acid), beads or liposomes, that may provide controlled or sustained release of the product which can be delivered via depot injection. Hyaluronic acid may also be used, having the effect of promoting sustained duration in the circulation. Implantable drug delivery devices may be used to introduce the desired antibody construct.

Sustained- or controlled-delivery/release formulations are also envisaged herein. Techniques for formulating a variety of other sustained- or controlled-delivery means, such as liposome carriers, bio-erodible microparticles or porous beads and depot injections, are also known to those skilled in the art. See, for example, International Patent Application No. PCT/US93/00829, which describes controlled release of porous polymeric microparticles for delivery of pharmaceutical compositions. Sustained-release preparations may include semipermeable polymer matrices in the form of shaped articles, e.g., films, or microcapsules. Sustained release matrices may include polyesters, hydrogels, poly-lactides (as disclosed in U.S. Pat. No. 3,773,919 and European Patent Application Publication No. EP 058481), copolymers of L-glutamic acid and gamma ethyl-L-glutamate (Sidman et al., 1983, Biopolymers 2:547-556), poly (2-hydroxyethyl-methacrylate) (Langer et al., 1981, J. Biomed-.Mater. Res. 15:167-277 and Langer, 1982, Chem. Tech. 12:98-105), ethylene vinyl acetate (Langer et al., 1981, supra) or poly-D(–)-3-hydroxybutyric acid (European Patent Application Publication No. EP 133,988). Sustained release compositions may also include liposomes that can be prepared by any of several methods known in the art. See, e.g., Eppstein et al., 1985, Proc. Natl. Acad. Sci. U.S.A. 82:3688-3692; European Patent Application Publication Nos. EP 036,676; EP 088,046 and EP 143,949. The antibody construct may also be entrapped in microcapsules prepared, for example, by coacervation techniques or by interfacial polymerization (for example, hydroxymethylcellulose or gelatine-microcapsules and poly (methylmethacylate) microcapsules, respectively), in colloidal drug delivery systems (for example, liposomes, albumin microspheres, microemulsions, nanoparticles and nanocapsules), or in macroemulsions. Such techniques are disclosed in Remington's Pharmaceutical Sciences, 22nd edition, Oslo, A., Ed., (2012).

Pharmaceutical compositions used for in vivo administration are typically provided as sterile preparations. Sterilization can be accomplished by filtration through sterile filtration membranes. When the composition is lyophilized, sterilization using this method may be conducted either prior to or following lyophilization and reconstitution. Compositions for parenteral administration can be stored in lyophilized form or in a solution. Parenteral compositions generally are placed into a container having a sterile access port, for example, an intravenous solution bag or vial having a stopper pierceable by a hypodermic injection needle.

The antibody constructs disclosed herein may also be formulated as immuno-liposomes. A "liposome" is a small vesicle composed of various types of lipids, phospholipids and/or surfactant which is useful for delivery of a drug to a mammal. The components of the liposome are commonly arranged in a bilayer formation, similar to the lipid arrangement of biological membranes. Liposomes containing the antibody construct are prepared by methods known in the art, such as described in Epstein et al., Proc. Natl. Acad. Sci. USA, 82: 3688 (1985); Hwang et al., Proc. Natl Acad. Sci. USA, 77: 4030 (1980); U.S. Pat. Nos. 4,485,045 and 4,544, 545; and WO 97/38731. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter. Fab' fragments of the antibody construct of the present invention can be conjugated to the liposomes as described in Martin et al. J. Biol. Chem. 257: 286-288 (1982) via a disulfide interchange reaction. A chemotherapeutic agent is optionally contained within the liposome. See Gabizon et al. J. National Cancer Inst. 81 (19) 1484 (1989).

It is envisaged that the composition of the invention might comprise, in addition to the bispecific single chained antibody construct defined herein, further biologically active agents, depending on the intended use of the composition. Such agents might be in particular drugs acting on tumors and/or malignant cells, but other active agents are also conceivable depending on the intended use of the pharmaceutical composition, including agents acting on on the gastro-intestinal system, drugs inhibiting immunoreactions (e.g. corticosteroids), drugs modulating the inflammatory response, drugs acting on the circulatory system and/or agents such as cytokines known in the art. It is also envisaged that the pharmaceutical composition of the present invention is applied in a co-therapy, i.e., in combination with another anti-cancer medicament.

Once the pharmaceutical composition has been formulated, it may be stored in sterile vials as a solution, suspension, gel, emulsion, solid, crystal, or as a dehydrated or lyophilized powder. Such formulations may be stored either in a ready-to-use form or in a form (e.g., lyophilized) that is reconstituted prior to administration. E.g., lyophilized compositions may be reconstituted in, e.g., bacteriostatic water for injection (BWFI), physiological saline, phosphate buffered saline (PBS), or the same formulation the protein had been in prior to lyophilization.

The pharmaceutical composition of the invention may in general be formulated for delivery by any suitable route of administration. In the context of the present invention, the routes of administration include, but are not limited to topical routes (such as epicutaneous, inhalational, nasal, opthalmic, auricular/aural, vaginal, mucosal); enteral routes (such as oral, gastrointestinal, sublingual, sublabial, buccal, rectal); and parenteral routes (such as intravenous, intraarterial, intraosseous, intramuscular, intracerebral, intracerebroventricular, epidural, intrathecal, subcutaneous, intraperitoneal, extra-amniotic, intraarticular, intracardiac, intradermal, intralesional, intrauterine, intravesical, intravitreal, transdermal, intranasal, transmucosal, intrasynovial, intraluminal).

The pharmaceutical compositions described herein are particularly useful for parenteral administration, e.g., subcutaneous or intravenous delivery, for example by injection such as bolus injection, or by infusion such as continuous infusion. Pharmaceutical compositions may be administered using a medical device. Examples of medical devices for administering pharmaceutical compositions are described in U.S. Pat. Nos. 4,475,196; 4,439,196; 4,447,224; 4,447, 233; 4,486,194; 4,487,603; 4,596,556; 4,790,824; 4,941,880; 5,064,413; 5,312,335; 5,312,335; 5,383,851; and 5,399,163.

The pharmaceutical composition of the invention can also be administered uninterruptedly. As a non-limiting example, uninterrupted or substantially uninterrupted, i.e. continuous administration may be realized by a small pump system worn by the patient for metering the influx of the antibody construct into the body of the patient. The pharmaceutical composition can be administered by using said pump systems. Such pump systems are generally known in the art, and commonly rely on periodic exchange of cartridges containing the therapeutic agent to be infused. When exchanging the cartridge in such a pump system, a temporary interruption of the otherwise uninterrupted flow of therapeutic agent into the body of the patient may ensue. In such a case, the phase of administration prior to cartridge replacement and the phase of administration following cartridge replacement would still be considered within the meaning of the pharmaceutical means and methods of the invention together make up one "uninterrupted administration" of such therapeutic agent.

The continuous or uninterrupted administration of the pharmaceutical composition of the invention may be intravenous or subcutaneous by way of a fluid delivery device or small pump system including a fluid driving mechanism for driving fluid out of a reservoir and an actuating mechanism for actuating the driving mechanism. Pump systems for subcutaneous administration may include a needle or a cannula for penetrating the skin of a patient and delivering the suitable composition into the patient's body. Said pump systems may be directly fixed or attached to the skin of the patient independently of a vein, artery or blood vessel, thereby allowing a direct contact between the pump system and the skin of the patient. The pump system can be attached to the skin of the patient for 24 hours up to several days. The pump system may be of small size with a reservoir for small volumes. As a non-limiting example, the volume of the reservoir for the suitable pharmaceutical composition to be administered can be between 0.1 and 50 ml.

Continuous administration may also be achieved transdermally by way of a patch worn on the skin and replaced at intervals. One of skill in the art is aware of patch systems for drug delivery suitable for this purpose. It is of note that transdermal administration is especially amenable to uninterrupted administration, as exchange of a first exhausted patch can advantageously be accomplished simultaneously with the placement of a new, second patch, for example on the surface of the skin immediately adjacent to the first exhausted patch and immediately prior to removal of the first exhausted patch. Issues of flow interruption or power cell failure do not arise.

The skilled person will readily understand that the pharmaceutical composition of the invention may in general comprise any of the aforementioned excipients, or additional active agents, or may be provided in any suitable form as long as it is stable and preferably exhibits the same advantageous properties as the pharmaceutical compositions comprising β-cyclodextrins that have been evaluated in the appended Examples. The skilled person will readily be able to adjust the various components so as to provide a pharmaceutical composition that is stable, i.e. is preferably substantially free from aggregates and/or conformers of the bispecific single chain antibody fragments comprised within.

It must be noted that as used herein, the singular forms "a", "an", and "the", include plural references unless the context clearly indicates otherwise. Thus, for example, reference to "a reagent" includes one or more of such different reagents and reference to "the method" includes reference to equivalent steps and methods known to those of ordinary skill in the art that could be modified or substituted for the methods described herein.

Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the present invention.

The term "and/or" wherever used herein includes the meaning of "and", "or" and "all or any other combination of the elements connected by said term".

The term "about" or "approximately" as used herein means within 20%, preferably within 10%, and more preferably within 5% of a given value or range. It includes, however, also the concrete number, e.g., about 20 includes 20.

The term "less than" or "greater than" includes the concrete number. For example, less than 20 means less than or equal to. Similarly, more than or greater than means more than or equal to, or greater than or equal to, respectively.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integer or step. When used herein the term "comprising" can be substituted with the term "containing" or "including" or sometimes when used herein with the term "having".

When used herein "consisting of" excludes any element, step, or ingredient not specified in the claim element. When used herein, "consisting essentially of" does not exclude materials or steps that do not materially affect the basic and novel characteristics of the claim.

In each instance herein any of the terms "comprising", "consisting essentially of" and "consisting of" may be replaced with either of the other two terms.

It should be understood that this invention is not limited to the particular methodology, protocols, material, reagents, and substances, etc., described herein and as such can vary. The terminology used herein is for the purpose of describing particular embodiments only, and is not intended to limit the scope of the present invention, which is defined solely by the claims.

All publications and patents cited throughout the text of this specification (including all patents, patent applications, scientific publications, manufacturer's specifications, instructions, etc.), whether supra or infra, are hereby incorporated by reference in their entirety. Nothing herein is to be construed as an admission that the invention is not entitled to antedate such disclosure by virtue of prior invention. To the extent the material incorporated by reference contradicts or is inconsistent with this specification, the specification will supersede any such material.

A better understanding of the present invention and of its advantages will be obtained from the following examples, offered for illustrative purposes only. The examples are not intended to limit the scope of the present invention in any way.

EXAMPLES

Example 1

Figure 3:
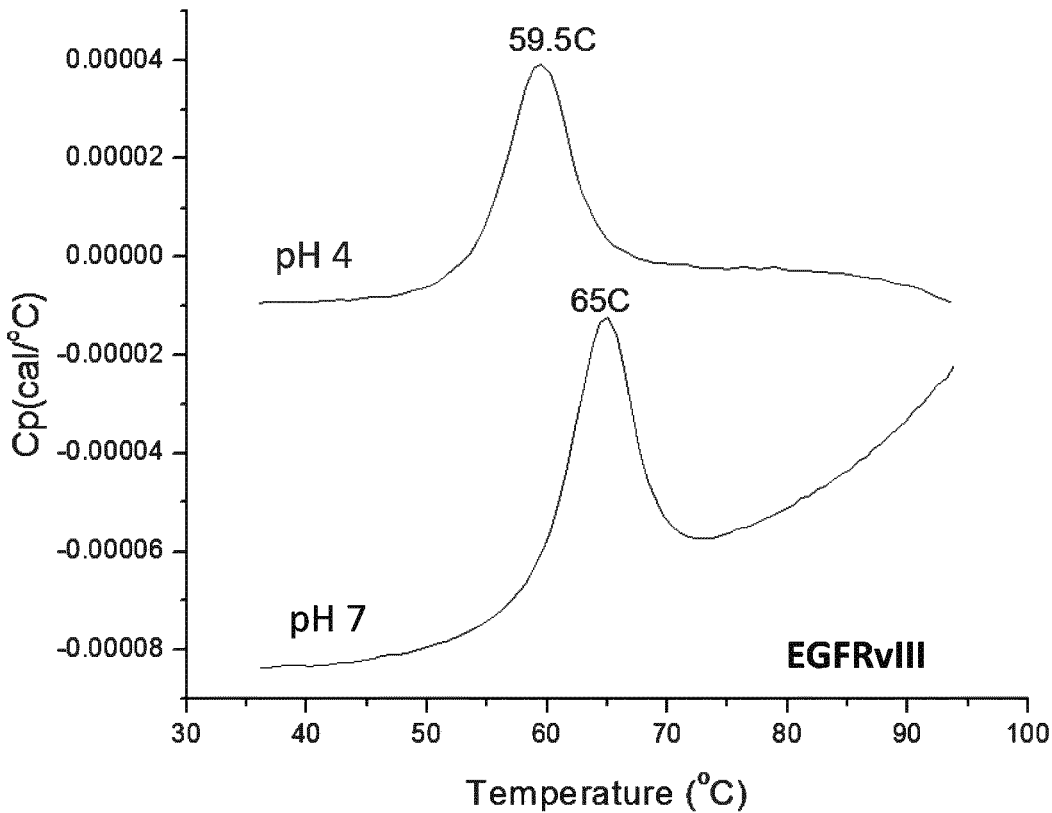
FIG. 3: DSC thermogram of a EGFRvIII antibody construct without HLE at pH 4 and pH 7. The Tm at pH 4 is 5.5C lower than the Tm at pH 7.

Canonical EGFRvII BiTE® antibody construct was provided in a buffer solution of either pH 7.0 or pH 4.0 and subjected to DSC, respectively. The DSC melting temperature of the antibody construct was obtained as a single melting event. At pH 7 the Tm was 65° C. while at pH 4 the Tm was 59.5° C., i.e. lower than in neutral medium (see thermogram in FIG. 3). Generally, a higher Tm stands for higher stability of a compound.

Example 2

Figure 4:
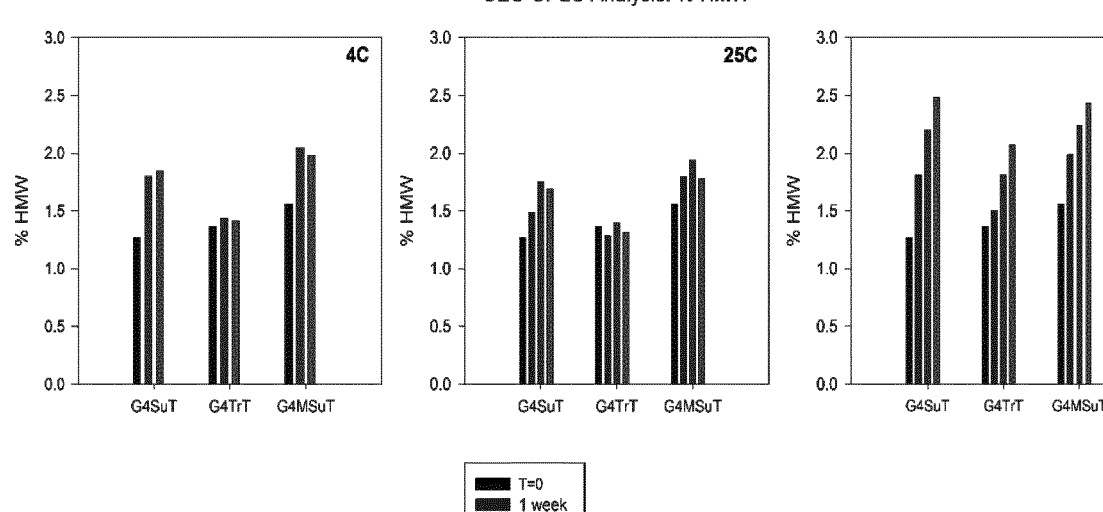
FIG. 4: (a) shows percentage of high molecular weight species of CDH19 scFc antibody constructs measured in pH 4 vs. pH 6. Lower aggregation is seen at the lower pH of 4.0; (b) shows percentage main peak of CDH19 scFc BiTE measured by SEC at 4C (time points T0, 2w, 4w), 25° C. (T0, 1w, 2w, 4w) and 37C (T0, 1w, 2w, 4w) in three different formulations—G4SuT, G4TrT and G4MSuT: G4SuT comprises 10 mM glutamate, 9% (w/v) Sucrose, 0.01% polysorbate 80, G4TrT comprises 10 mM glutamate, 9% (w/v) Trehalose, 0.01% Polysorbate 80, and G4MSuT comprises 10 mM glutamate, 4% (w/v) Mannitol, 2% Sucrose, 0.01% polysorbate 80. Stability is demonstrated at pH 4. (c) shows percentage main peak of CDH19 scFc BiTE measured by SEC at −20° C. (T0, 4w) in three different formulations—G4SuT, G4TrT and G4MSuT. (d) shows percentage high molecular weight (HMW) peak of CDH19 scFc BiTE measured by SEC at 4C (T0, 2w, 4w), 25° C. (T0, 1w, 2w, 4w) and 37° C. (T0, 1w, 2w, 4w) in three different formulations: G4SuT, G4TrT and G4MSuT. (e) shows percentage HMW peak of CDH19 scFc BiTE measured by SEC at −20° C. (T0, 4w) in three different formulations—G4SuT, G4TrT and G4MSuT. (f) shows percentage low molecular weight peak of CDH19 scFc BiTE measured by SEC at 4C (T0, 2w, 4w), 25C (T0, 1w, 2w, 4w) and 37C (T0, 1w, 2w, 4w) in three different formulations—G4SuT, G4TrT and G4MSuT.
Figure 4:
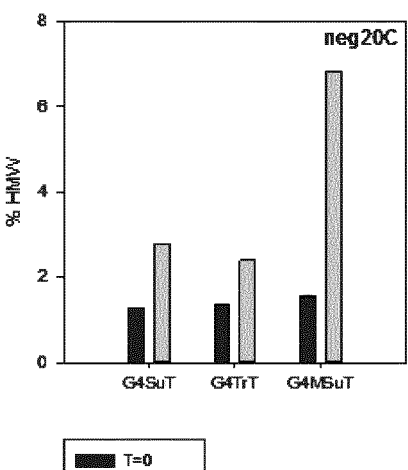
Figure 4:
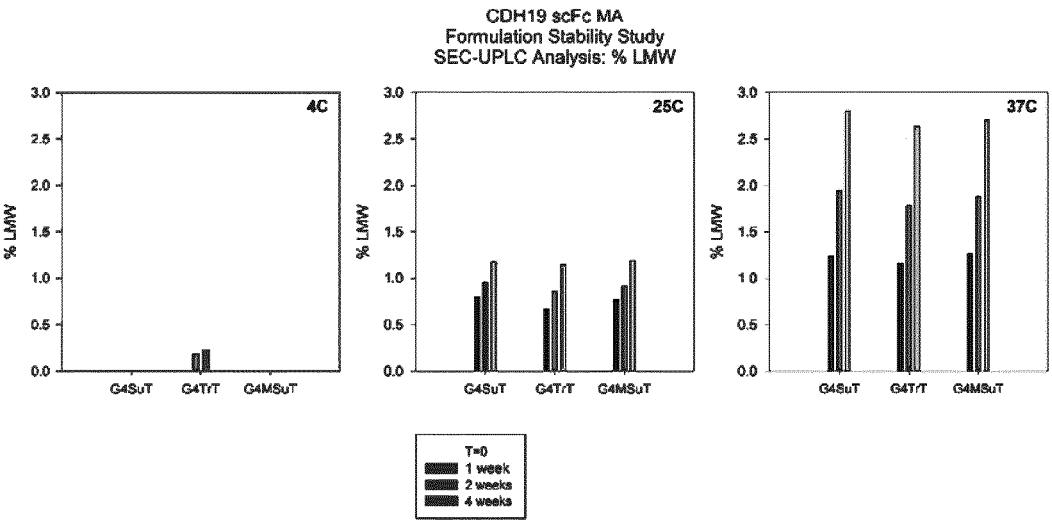
Figure 5:
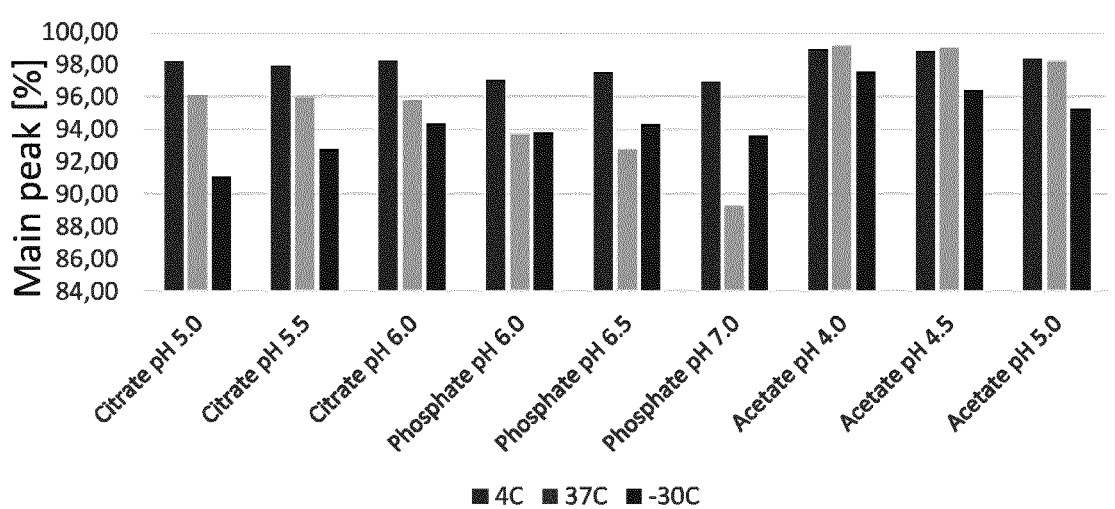
FIG. 5: Percentage main peak of EGFRvIII non-scFC antibody construct in various buffers in the pH range 4 to 7 measured after 6 months. At pH 4.0, the antibody construct has the highest main peak percentage.
Figure 6:
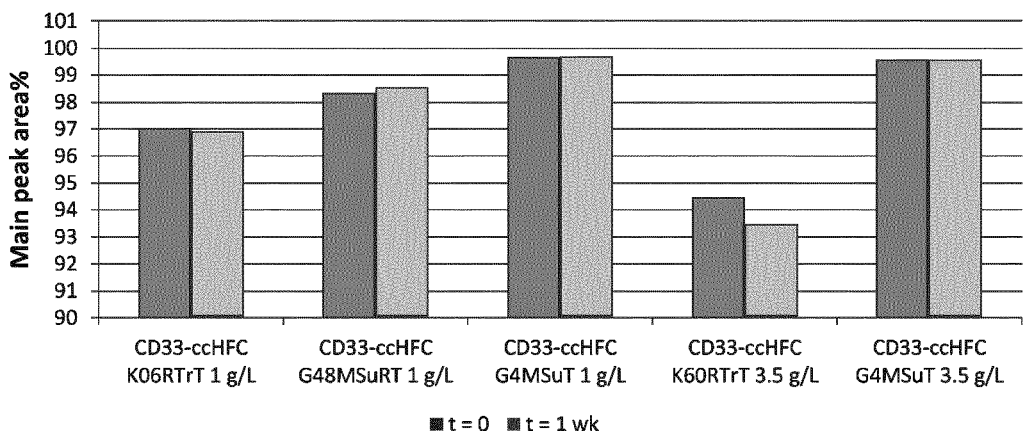
FIG. 6: (a) shows percentage main peak of CD33-scFc antibody construct at different concentrations in different formulations at 4° C. The "ccHFC" stands for a specifically modified cys-clamed scFc domain. Low pH formulations consistently have higher monomeric species. (b) shows percentage main peak of CD33-scFc antibody construct at different concentrations in different formulations at 25° C. The "ccHFC" stands for a specifically modified cys-clamed scFc domain Low pH formulations consistently have higher monomeric species.
Figure 6:
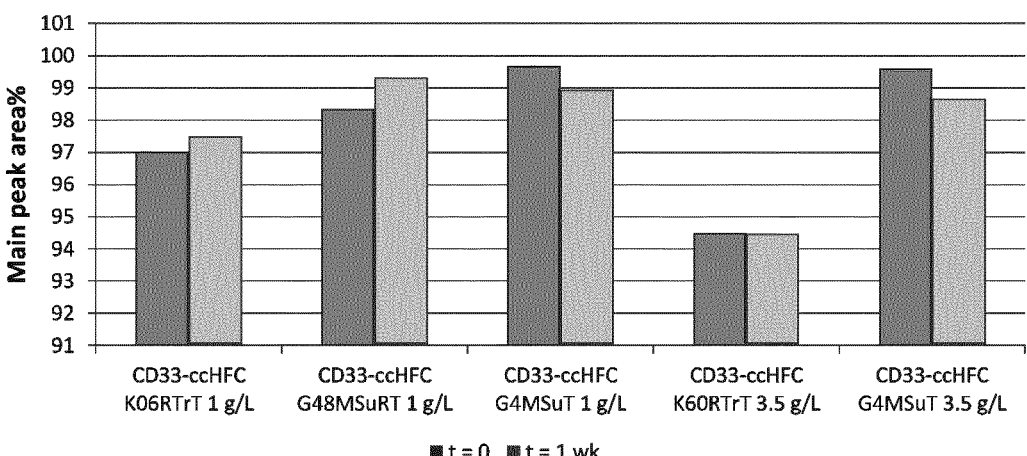
Figure 7:
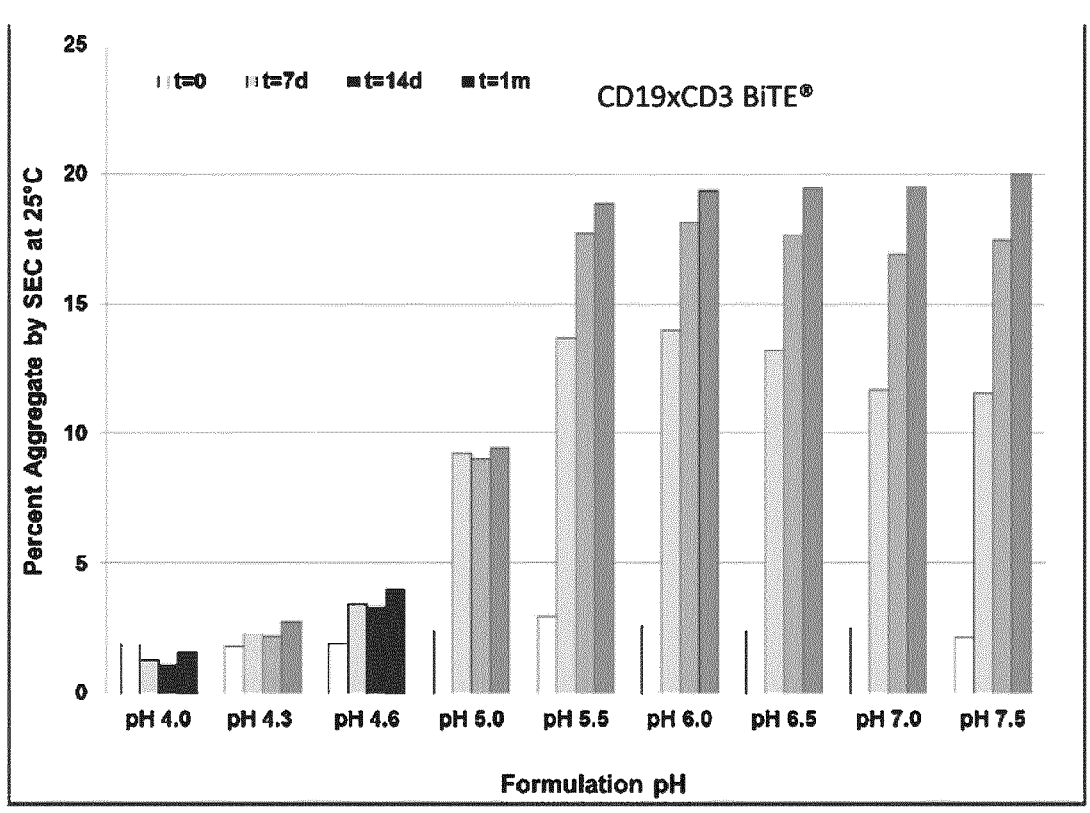
FIG. 7: Percentage aggregation of canonical (non-HLE) CD19×CD3 BiTE® antibody construct as measured by SEC as a function of pH at T0, 7 days, 14 days and 1 month. The figure demonstrates that at low pH the amount of aggregation is dramatically lower.

Preformulated drug substances containing purified canonical or scFc-provided BiTE antibody constructs with a first target domain against CDH19, EGFRvIII, CD33 and CD19, respectively, were buffer exchanged via ultrafiltration/diafiltration using membranes with a molecular weight cut-off (MWCO) of 10 kDa. Final formulation was achieved by adding concentrated stock solutions. Resulting formulations for each construct are K60RTrT composed of 20 mM potassium phosphate, 150 mM L-arginine hydrochloride, 6% (w/V) trehalose dihydrate, 0.01% (w/V) polysorbate 80 at pH 6.0 and G40MSuT composed of 10 mM glutamate, 4% (w/V) mannitol, 2% (w/V) sucrose, 0.01% (w/V) polysorbate 80 at pH 4.0. The protein concentration totaled 1.0 mg/mL. 1950 µL of each test solution was spiked with 50 µL of a 1000 ppm silicon standard solution (Specpure from AlfaAesar, Art.No. 38717) resulting in a 25 ppm spike. An unspiked test solution served as control sample. The spiked test solution as well as the control sample were filled into 3cc type I glass vials and were incubated at 37° C. for 24 hours. All samples were analyzed by SE-UPLC in order to quantify the amount of HMWS. As a result, FIG. 4 (a) shows percentage of high molecular weight species of CDH19 scFc antibody constructs measured in pH 4 vs. pH 6. Lower aggregation is seen at the lower pH of 4.0. FIG. 4 (b) shows percentage main peak of CDH19 scFc BiTE measured by SEC at 4° C. (time points T0, 2w, 4w), 25° C. (T0, 1w, 2w, 4w) and 37C (T0, 1w, 2w, 4w) in three different formulations—G4SuT, G4TrT and G4MSuT: G4SuT comprises 10 mM glutamate, 9% (w/v) Sucrose, 0.01% polysorbate 80, G4TrT comprises 10 mM glutamate, 9% (w/v) Trehalose, 0.01% Polysorbate 80, and G4MSuT comprises 10 mM glutamate, 4% (w/v) Mannitol, 2% Sucrose, 0.01% polysorbate 80. Stability is demonstrated at pH 4. The respective antibody construct formulations were stored at various conditions for stability monitoring. FIG. 4 (c) shows percentage main peak of CDH19 scFc BiTE measured by SEC at −20° C. (T0, 4w) in three different formulations—G4SuT, G4TrT and G4MSuT. FIG. 4 (d) shows percentage high molecular weight (HMW) peak of CDH19 scFc BiTE measured by SEC at 4C (T0, 2w, 4w), 250C (T0, 1w, 2w, 4w) and 37° C. (T0, 1w, 2w, 4w) in three different formulations: G4SuT, G4TrT and G4MSuT. FIG. 4 (e) shows percentage HMW peak of CDH19 scFc BiTE measured by SEC at −20° C. (T0, 4w) in three different formulations—G4SuT, G4TrT and G4MSuT. FIG. 4(f) shows percentage low molecular weight peak of CDH19 scFc BiTE measured by SEC at 4C (T0, 2w, 4w), 25C (T0, 1w, 2w, 4w) and 37C (T0, 1w, 2w, 4w) in three different formulations—G4SuT, G4TrT and G4MSuT. FIG. 5 shows percentage main peak of EGFRvIII non-scFC antibody construct in various buffers in the pH range 4 to 7 measured after 6 months. At pH 4.0, the antibody construct has the highest main peak percentage. FIG. 6: (a) shows percentage main peak of CD33-scFc antibody construct at different concentrations in different formulations at 4° C. The "ccHFC" stands for a specifically modified cys-clamed scFc domain. Low pH formulations consistently have higher monomeric species. (b) shows percentage main peak of CD33-scFc antibody construct at different concentrations in different formulations at 25° C. The "ccHFC" stands for a specifically modified cys-clamed scFc domain Low pH formulations consistently have higher monomeric species. FIG. 7: Percentage aggregation of canonical (non-HLE) CD19×CD3 BiTE® antibody construct as measured by SEC as a function of pH at T0, 7 days, 14 days and 1 month. The figure demonstrates that at low pH the amount of aggregation is dramatically lower.

Example 3

EGFRvIII BiTE® antibody construct was purified using immobilized metal affinity chromatography (IMAC) followed by size exclusion chromatography (SEC). The SEC eluate contained 0.43 mg/mL EGFRvIII in 20 mM citric acid and 2% (w/v) trehalose dihydrate at pH 5.0. The material was splitted into three fractions. The first fraction was kept at pH 5.0. The pH of the other fractions was adjusted to 6.0 and 7.0 respectively. All fractions were filtered through a filter with a pore size of 0.2 μm. Each fraction was finally formulated by spiking with concentrated excipient stock solutions. An overview on final formulations is provided by Table 4. The EGFRvIII concentration in each formulation equaled 0.1 mg/mL. The formulation were filled to 1.0 mL in 2R type I glass vials which were closed with butyl rubber stoppers and aluminum flip off seals.

Table 4: Overview on tested formulations. The plan below represents a four factor full factorial experimental design with 2(4-0) different formulations. Formulations marked with an asterix (*) represent center points of the experimental design and have been prepared in triplicates.

TABLE 4

Overview on tested formulations. The plan below represents a four factor full factorial experimental design with 2(4-0) different formulations. Formulations marked with an asterix (*) represent center points of the experimental design and have been prepared in triplicates.

| Designation | Amino acid (100 mM) | Trehalose dihydrate [% w/v] | Polysorbate 80 [% w/v] | pH |
|---|---|---|---|---|
| A1 | L-arginine HCl | 2.0 | 0.002 | 5.0 |
| A2 | L-arginine HCl | 10.0 | 0.002 | 5.0 |
| A3 | L-arginine HCl | 2.0 | 0.018 | 5.0 |
| A4 | L-arginine HCl | 10.0 | 0.018 | 5.0 |
| A5 | L-arginine HCl | 2.0 | 0.002 | 7.0 |
| A6 | L-arginine HCl | 10.0 | 0.002 | 7.0 |
| A7 | L-arginine HCl | 2.0 | 0.018 | 7.0 |
| A8 | L-arginine HCl | 10.0 | 0.018 | 7.0 |
| A9* | L-arginine HCl | 6.0 | 0.010 | 6.0 |
| A10* | L-arginine HCl | 6.0 | 0.010 | 6.0 |
| A11* | L-arginine HCl | 6.0 | 0.010 | 6.0 |
| L1 | L-Lysine HCl | 2.0 | 0.002 | 5.0 |
| L2 | L-Lysine HCl | 10.0 | 0.002 | 5.0 |
| L3 | L-Lysine HCl | 2.0 | 0.018 | 5.0 |
| L4 | L-Lysine HCl | 10.0 | 0.018 | 5.0 |
| L5 | L-Lysine HCl | 2.0 | 0.002 | 7.0 |
| L6 | L-Lysine HCl | 10.0 | 0.002 | 7.0 |
| L7 | L-Lysine HCl | 2.0 | 0.018 | 7.0 |
| L8 | L-Lysine HCl | 10.0 | 0.018 | 7.0 |
| L9* | L-Lysine HCl | 6.0 | 0.010 | 6.0 |
| L10* | L-Lysine HCl | 6.0 | 0.010 | 6.0 |
| L11* | L-Lysine HCl | 6.0 | 0.010 | 6.0 |

The formulations were stored at 25° C. for four days and then analyzed by optical density measurements at 350 nm, size exclusion ultra-high performance chromatography and weak cation exchange (WCX) chromatography. The optical density at 350 nm was measured in 96-well plate using Tecan Infinite M1000 plate reader from Tecan. The aggregation index (AI) was calculated using the following equation:

$$AI = OD_{350} \text{ nm}/(OD_{280} \text{ nm} - OD_{350} \text{ nm})$$

SEC was applied to determine the percentaged content of high molecular weight species (HMWS) in each formulation and protein concentration after stress. SE-UPLC was performed on an Aquity H-Class UPLC system (Waters) using an Acquity UPLC BEH200 SEC 150 mm column (Waters). Column temperature was set to 25° C. Separation of size variants was achieved by applying an isocratic method with a flow rate of 0.4 mL/min. The mobile phase was composed of 100 mM sodium phosphate, 250 mM NaCl pH 6.8. The run time totals 6.0 minutes. Samples were held at 8° C.

within the autosampler until analysis. A total amount of 3 μg protein was injected. In order to avoid carry over an intermediate injection with 40% ACN was performed after each sample. Detection was based on fluorescence (excitation at 280 nm, emission at 325 nm) for the quantitation of HMWS. For the determination of protein concentration detection via photodiode array (PDA) at 280 nm was used. Peak integration was performed using Empower® software. Relative area under the curve of HMWS was reported. WCX chromatography was performed on an Aquity H-Class UPLC system (Waters) using a Protein-Pak Hi Res CM 7 μm column (Waters. cat No. 186004929). Column temperature was set to 30° C. Separation of charge variants was achieved by applying the gradient method depicted in Table 5 using a flow rate of 0.65 mL/min. The mobile phases A and B were composed of 20 mM sodium phosphate pH 6.5 and 20 mM sodium phosphate.

TABLE 5

Gradient used for WCX chromatography

| Time [min.] | % A | % B |
|---|---|---|
| Initial | 100 | 0 |
| 4.00 | 100 | 0 |
| 5.01 | 70 | 30 |
| 10.00 | 45 | 55 |
| 10.01 | 0 | 100 |
| 12.50 | 0 | 100 |
| 12.51 | 100 | 0 |
| 15.00 | 100 | 0 |

Samples were held at 8° C. within the autosampler until analysis. 5 μg of protein were injected onto the column. Samples were prediluted with mobile phase A. In order to avoid carry over an intermediate injection with 40% ACN was performed after each sample. Detection was based on fluorescence (Ex 280 nm, Ex 325 nm). Peak integration was performed using Empower® software. Relative area under the curve (AUC) of the main peak (native species) was reported.

Figure 8:
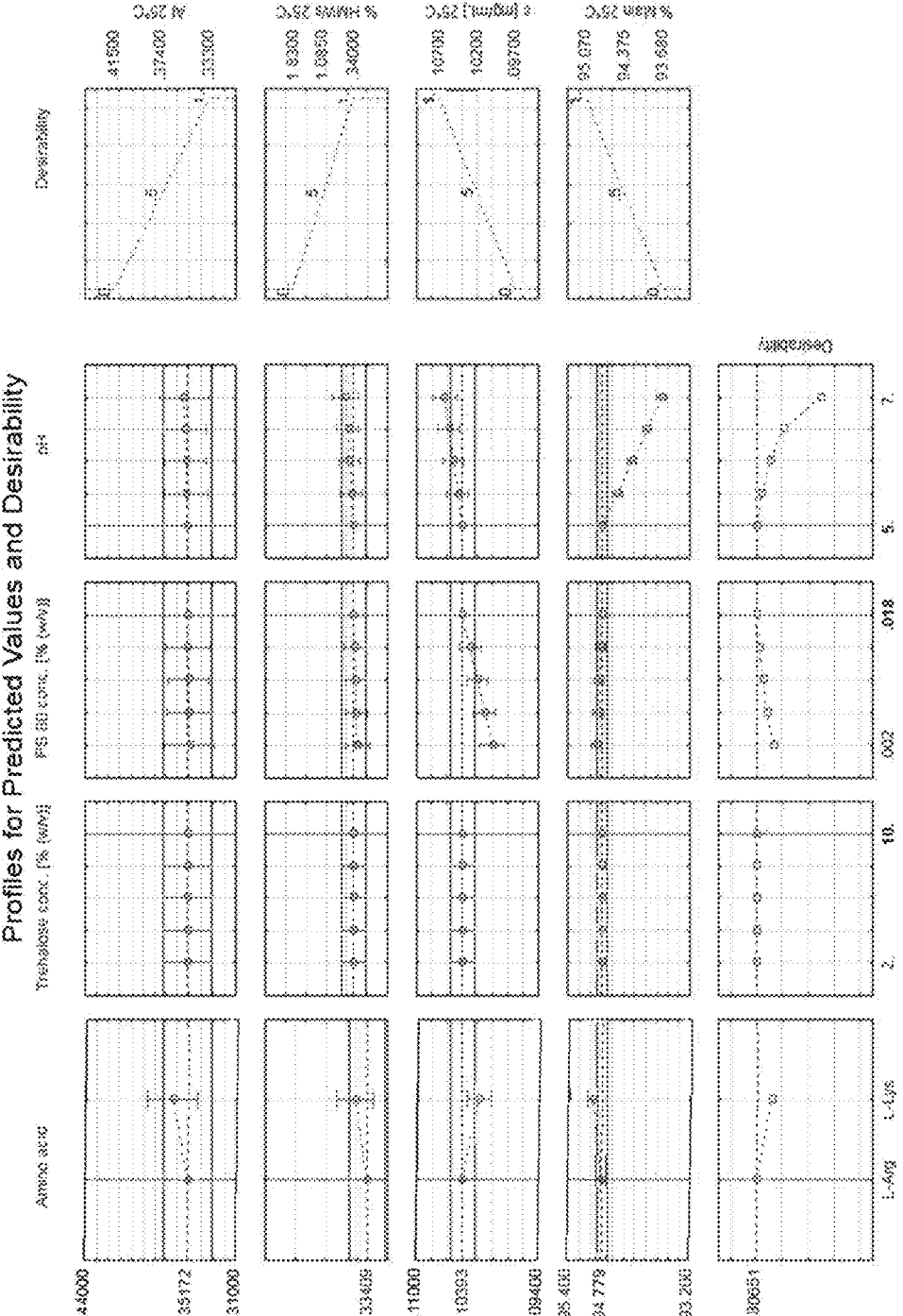
FIG. 8: Profiles for predicted values and desirability in function of formulation parameters generated by Statistica software (Statsoft).

Statistica software (Statsoft) was used to statistically evaluate the impact of above formulation parameters on the measured aggregation index, percentaged content of HMWS, protein concentration, and the abundance of the WCX main peak. The profiles for predictive values and desirability are depicted FIG. 8. An optimal formulation strives for a low aggregation index, low HMWS, high protein concentration, and a high main peak percentage. As illustrated by FIG. 8, desirability is maximized by using L-Arginine, high PS 80 concentrations and formulation at low pH values.

Example 4

Mesothelin (MSLN)-scFc BiTE antibody construct was purified using Protein A, cation exchange (CEX), and hydroxyapatite (HA) chromatography. The HA eluate was then preformulated using ultrafiltration/diafiltration (UFDF). Final formulation was achieved by spiking with concentrated excipient stock solutions. An overview on tested formulations is provided by Table 6.

TABLE 6

| Overview on tested formulations | |
| --- | --- |
| Designation | Formulation composition |
| G40MSuT-low | 10 mM glutamate<br>4% (w/v) Mannitol, 2% (w/v) Sucrose<br>0.01% (w/v) PS 80<br>pH 4.0<br>1.0 mg/mL MSLN-scFc |
| G40MSuT-high | 10 mM glutamate<br>4% (w/v) Mannitol, 2% (w/v) Sucrose<br>0.01% (w/v) PS 80<br>pH 4.0<br>5.0 mg/mL MSLN-scFc |
| K60TrT-low | 20 mM potassium phosphate<br>150 mM L-Arginine HCl<br>6% (w/v) Trehalose *2 H$_2$O<br>0.01% (w/v) PS 80<br>pH 6.0<br>1.0 mg/mL MSLN-scFc |
| K60TrT-high | 20 mM potassium phosphate<br>150 mM L-Arginine HCl<br>6% (w/v) Trehalose *2 H$_2$O<br>0.01% (w/v) PS 80<br>pH 6.0<br>5.0 mg/mL MSLN-scFc |
| K70LTrT-low | 20 mM potassium phosphate<br>75 mM Lysine hydrochloride<br>4% (w/V) Trehalose dihydrate<br>0.01% (w/V) PS 80<br>pH 7.0<br>1.0 mg/mL MSLN-scFc |
| K70LTrT-high | 20 mM potassium phosphate<br>75 mM Lysine hydrochloride<br>4% (w/V) Trehalose dihydrate<br>0.01% (w/V) PS 80<br>pH 7.0<br>5.0 mg/mL MSLN-scFc |

Above formulations were filled to 1.3 mL in 2R1 type I glass vials which were closed with butyl rubber stoppers and aluminum flip off seals. The formulations were stored at −20, 25, and 37° for up to four weeks and at 2-8° C. for up to 15 weeks. Samples were pulled at designated time points. Additionally samples were subjected to five consecutive freeze thaw cycles (20° C.→-50° C.→20° C. at 0.3 K/min, one hour hold at target temperatures). Samples were analyzed by size-exclusion ultra-high performance chromatography (SE-UPLC) and peptide mapping (only for none stressed samples and sample stored at 37° C.).

Figure 9:
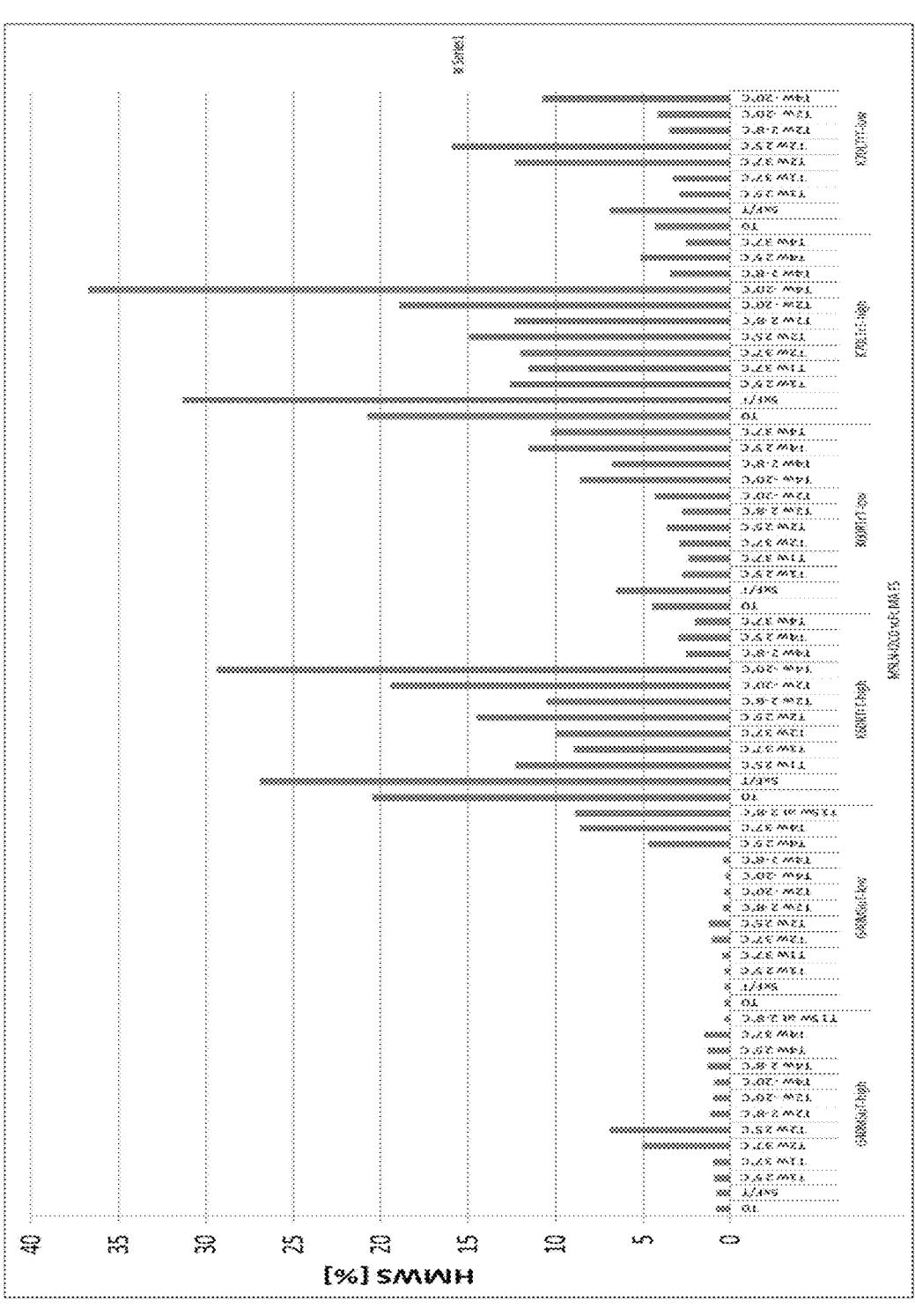
FIG. 9: Overview on percentaged content of high molecular weight species (HMWS) in MSLN-scFc preparations determined by size exclusion ultra-high performance chromatography (SE-UPLC) in function of formulation

SE-UPLC was performed on an Aquity H-Class UPLC system (Waters) using an Acquity UPLC BEH200 SEC 150 mm column (Waters). Column temperature was set to 25° C. Separation of size variants was achieved by applying an isocratic method with a flow rate of 0.4 mL/min. The mobile phase was composed of 100 mM sodium phosphate, 250 mM NaCl pH 6.8. The run time totals 6.0 minutes. Samples were held at 8° C. within the autosampler until analysis. A total amount of 3 µg protein was injected. In order to avoid carry over an intermediate injection with 40% ACN was performed after each sample. Detection was based on fluorescence (excitation at 280 nm, emission at 325 nm). Peak integration was performed using Empower® software. Relative area under the curve of HMWS was reported (FIG. 9).

The abundance of chemical modifications upon heat stress (incubation at 37° C.) was monitored by peptide mapping. Protein samples were enzymatically digested and the resulting peptides were separated using reversed phase chromatography. The column eluate was directly injected into the ion source of a mass spectrometer for identification and quantitation of the peptides.

In order to achieve maximum coverage, two separate enzyme digests were performed: once with trypsin and once with chymotrypsin. In each case, the proteins were denatured with guanidinum chloride and then reduced with dithiothreitol (DTT). After incubation in DTT, free cysteine residues were alkylated by the addition of iodoacetic acid. Samples were then buffer exchanged into 50 mM Tris (hydroxymethyl)aminomethane pH 7.8 for digestion. Trypsin and chymotrypsin were added to separate reaction tubes at a ratio of 1:10 (sample:enzyme) each. Samples were digested for 30 min at 37° C. and the reaction was quenched by adding trifluoroacetic acid.

A load of 5 µg of each digest was separately injected onto a Zorbax SB-C18 (Agilent #859700-902) reversed phase column equilibrated in 0.1% (V/V) formic acid (FA). A 156 minute gradient of up to 90% acetonitrile containing 0.1% FA was used to elute the peptides directly into the electrospray ion source of a Q-Exactive™ Plus mass spectrometer with advanced quadrupole technology (Thermo Scientific). Data was collected in data dependent mode using a top 12 method in which a full scan (resolution 70 000; scan range 200-2000 m/z) was followed by high energy collision dissociation (HCD) of the 12 most abundant ions (resolution 17 500). Peptides were identified based on accurate mass and tandem mass spectrum using in-house software. Identifications were manually verified. Relative quantities of modified and unmodified peptides were calculated based on ion abundance using Pinpoint software (Thermo Scientific). Percentages of chemical modifications of the complement determining regions (CDRs) and of the half-life extending portion are given by Table 7.

As demonstrated in FIG. 9 the abundance of HMWS is significantly reduced when MSLN-scFc is formulated at pH 4.0 if compared to formulations at pH 6.0 or 7.0. Table 7 provides an overview of chemical modifications in function of the formulation after storage at 37° C. for two weeks.

As outlined by Table 7 MLSN-scFc is less prone to chemical modifications when formulated at pH 4.0 if compared to pH 6.0 and 7.0.

TABLE 7

| | Overview on chemical modifications [%] in stressed MSLN-scFc formulations determined via peptide mapping | | | | |
| --- | --- | --- | --- | --- | --- |
| Domain | Degradation tpye | Degradation site | G40MSuT-low | K60RTrT-low | K70LTrT-low |
| Target | deamidation | N101 | 3.2 | 0.7 | 0.6 |
| binder | deamidation | N162 | 3.3 | 15.0 | 14.0 |
| CD3 | deamidation | N348 | 2.9 | 9.4 | 24.5 |
| binder | deamidation | N351 | 0.8 | 3.8 | 10.0 |

TABLE 7-continued

Overview on chemical modifications [%] in stressed
MSLN-scFc formulations determined via peptide mapping

| Domain | Degradation tpye | Degradation site | G40MSuT-low | K60RTrT-low | K70LTrT-low |
|---|---|---|---|---|---|
| Single chain Fc | oxidation | M530 | 4.3 | 4.0 | 5.4 |
| | oxidation | M706 | 2.5 | 2.1 | 3.7 |
| | deamidation | N603 | 5.6 | 7.0 | 7.5 |
| | Sum of degrdations: | | 22.6 | 42.0 | 65.7 |

Example 5

CD33cc-scF5 BiTE antibody construct was purified using Protein A, cation exchange (CEX), and hydroxyapatite (HA) chromatography. The HA eluate was then preformulated using ultrafiltration/diafiltration (UFDF). Final formulation was achieved by spiking with concentrated excipient stock solutions. An overview on tested formulations is provided by Table 8.

TABLE 8

Overview on tested formulations

| Designation | Formulation composition |
|---|---|
| G40MSuT-low | 10 mM glutamate<br>4% (w/v) Mannitol, 2% (w/v) Sucrose<br>0.01% (w/v) PS 80<br>pH 4.0<br>1.0 mg/mL CD33CC-scFc |
| G40MSuT-high | 10 mM glutamate<br>4% (w/v) Mannitol, 2% (w/v) Sucrose<br>0.01% (w/v) PS 80<br>pH 4.0<br>5.0 mg/mL CD33CC-scFc |
| K60TrT-low | 20 mM potassium phosphate<br>150 mM L-Arginine HCl<br>6% (w/v) Trehalose *2 $H_2O$<br>0.01% (w/v) PS 80<br>pH 6.0<br>1.0 mg/mL CD33CC-scFc |
| K60TrT-high | 20 mM potassium phosphate<br>150 mM L-Arqinine HCl<br>6% (w/v) Trehalose *2 $H_2O$<br>0.01% (w/v) PS 80<br>pH 6.0<br>5.0 mg/mL CD33CC-scFc |
| K70LTrT-low | 20 mM potassium phosphate<br>75 mM Lysine hydrochloride<br>4% (w/V) Trehalose dihydrate<br>0.01% (w/V) PS 80<br>pH 7.0<br>1.0 mg/mL CD33CC-scFc |
| K70LTrT-high | 20 mM potassium phosphate<br>75 mM Lysine hydrochloride<br>4% (w/V) Trehalose dihydrate<br>0.01% (w/V) PS 80<br>pH 7.0<br>5.0 mg/mL CD33CC-scFc |

Above formulations were filled to 1.3 mL in 2R type I glass vials which were closed with butyl rubber stoppers and aluminum flip off seals. The formulations were stored at −20, 2-8, 25, and 37° C. for up to four weeks. Samples were pulled at designated time points. Additionally samples were subjected to five consecutive freeze thaw cycles (20° C.→−50° C.→20° C. at 0.3 K/min, one hour hold at target temperatures). Samples were analyzed by size-exclusion ultra-high performance chromatography (SE-UPLC) and peptide mapping (only for none stressed samples and sample stored at 37° C.).

Figure 10:
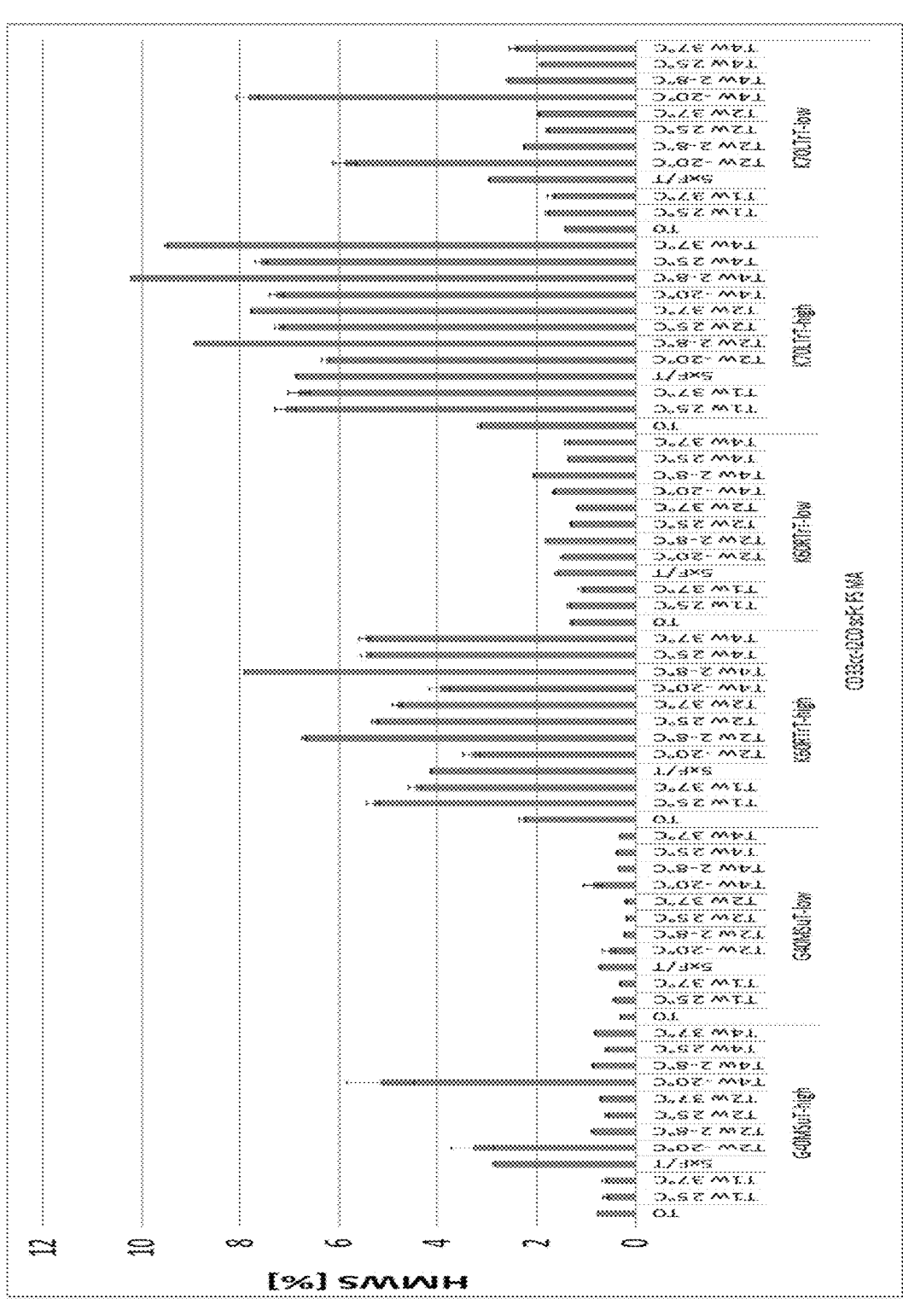
FIG. 10: Overview on percentaged content of high molecular weight species (HMWS) in CD33cc-scFc preparations determined by size exclusion ultra-high performance chromatography (SE-UPLC) in function of formulation.

SE-UPLC was performed on an Aquity H-Class UPLC system (Waters) using an Acquity UPLC BEH200 SEC 150 mm column (Waters). Column temperature was set to 25° C. Separation of size variants was achieved by applying an isocratic method with a flow rate of 0.4 mL/min. The mobile phase was composed of 100 mM sodium phosphate, 250 mM NaCl pH 6.8. The run time totals 6.0 minutes. Samples were held at 8° C. within the autosampler until analysis. A total amount of 3 μg protein was injected. In order to avoid carry over an intermediate injection with 40% ACN was performed after each sample. Detection was based on fluorescence (excitation at 280 nm, emission at 325 nm). Peak integration was performed using Empower® software. Relative area under the curve of HMWS was reported (FIG. 10).

The abundance of chemical modifications upon heat stress (incubation at 37° C.) was monitored by peptide mapping. Protein samples were enzymatically digested and the resulting peptides were separated using reversed phase chromatography. The column eluate was directly injected into the ion source of a mass spectrometer for identification and quantitation of the peptides.

In order to achieve maximum coverage, two separate enzyme digests were performed: once with trypsin and once with chymotrypsin. In each case, the proteins were denatured with guanidinum chloride and then reduced with dithiothreitol (DTT). After incubation in DTT, tree cysteine residues were alkylated by the addition of iodoacetic acid. Samples were then buffer exchanged into 50 mM Tris (hydroxymethyl)aminomethane pH 7.8 for digestion. Trypsin and chymotrypsin were added to separate reaction tubes at a ratio of 1:10 (sample:enzyme) each. Samples were digested for 30 min at 37° C. and the reaction was quenched by adding trifluoroacetic acid.

A load of 5 μg of each digest was separately injected onto a Zorbax SB-C18 (Agilent #859700-902) reversed phase column equilibrated in 0.1% (V/V) formic acid (FA). A 156 minute gradient of up to 90% acetonitrile containing 0.1% FA was used to elute the peptides directly into the electrospray ion source of a Q-Exactive™ Plus mass spectrometer with advanced quadrupole technology (Thermo Scientific). Data was collected in data dependent mode using a top 12 method in which a full scan (resolution 70 000; scan range 200-2000 m/z) was followed by high energy collision dissociation (HCD) of the 12 most abundant ions (resolution 17 500).

Peptides were identified based on accurate mass and tandem mass spectrum using in-house software. Identifications were manually verified. Relative quantities of modified and unmodified peptides were calculated based on ion abundance using Pinpoint software (Thermo Scientific).

Percentages of chemical modifications of the complement determining regions (CDRs) and of the half-life extending portion are given by Table 9.

As demonstrated in FIG. 10 the abundance of HMWS is significantly reduced when CD33cc-scFc is formulated at pH 4.0 if compared to formulations at pH 6.0 or 7.0. Table 7 provides an overview of chemical modifications in function of the formulation after storage at 37° C. for two weeks. As outlined by Table 9 CD33cc-scFc is less prone to chemical modifications when formulated at pH 4.0 if compared to pH 6.0 and 7.0.

TABLE 10

Overview on HMWS contents in MSLN-hALB, and -scFc preparations determined Via SE-UPLC after spiking with 25 ppm silicon

| | Construct | | |
|---|---|---|---|
| | hALB | scFc | |
| | | Formulation | |
| | K60RTrT | K60RTrT | G40MSuT |
| | Δ % HMWS (compared to unspiked control) | | |
| 25 ppm spike | 1.0 | 1.0 | 0.2 |

TABLE 9

Overview on chemical modifications [%] in stressed CD33cc-scFc formulations determined via peptide mapping

| Domain | Degradation tpye | Degradation site | G40MSuT-low | K60RTrT-low | K70LTrT-low |
|---|---|---|---|---|---|
| Target | oxidation | M34 | 1.7 | 1.0 | 1.6 |
| binder | isomerization | D103 | 7.3 | 5.8 | 6.1 |
| CD3 | oxidation | M290 | 1.3 | 0.8 | 1.4 |
| binder | deamidation | N359 | 0.9 | 7.0 | 23.2 |
| | deamidation | N362 | 0.3 | 3.1 | 9.0 |
| Single | isomerization | D510 | 2.3 | 2.3 | 1.8 |
| chain Fc | oxidation | M541 | 4.7 | 4.2 | 7.2 |
| | deamidation | N614 | 4.5 | 7.4 | 7.7 |
| | deamidation | N673 | 0.5 | 1.1 | 4.5 |
| | oxidation | M717 | 3.0 | 2.1 | 4.5 |
| Sum of degradations: | | | 26.5 | 34.8 | 67.0 |

Example 6

Preformulated drug substances containing purified MSLN-hALB, MSLN-hFc, and MSLN-scFc respectively were buffer exchanged via ultrafiltration/diafiltration using membranes with a molecular weight cut-off (MWCO) of 10 kDa. Final formulation was achieved by adding concentrated stock solutions. Resulting formulations for each construct are K60RTrT composed of 20 mM potassium phosphate, 150 mM L-arginine hydrochloride, 6% (w/V) trehalose dihydrate, 0.01% (w/V) polysorbate 80 at pH 6.0 and G40MSuT composed of 10 mM glutamate, 4% (w/V) mannitol, 2% (w/V) sucrose, 0.01% (w/V) polysorbate 80 at pH 4.0. MSLN-hALB was formulated in K60RTrT and MSLN-scFc was formulated in K60RTrT and G40MSuT. The protein concentration totaled 1.0 mg/mL. 1950 µL of each test solution was spiked with 50 µL of a 1000 ppm silicon standard solution (Specpure from AlfaAesar, Art.No. 38717) resulting in a 25 ppm spike. An unspiked test solution served as control sample. The spiked test solution as well as the control sample were filled into 3cc type I glass vials and were incubated at 37° C. for 24 hours. All samples were analyzed by SE-UPLC according to the method described in Example 4 in order to quantify the amount of HMWS (Table 10). When formulated in K60RTrT, MSLN-hALB and -scFc showed similar increases in HMWS upon silicon spiking. For the scFc construct it could be shown that this increase could be reduced by lowering the formulation pH to 4.0. According to preliminary experiments, this approach was not feasible for MLSN-hALB since it revealed to undergo fragmentation at formulation pH values of 5.0 and below.

For the scFc construct it could be shown that an increase in undesired high molecular weight species could be reduced by lowering the formulation pH to 4.0. According to preliminary experiments, this approach was not feasible for MLSN-hALB since it revealed to undergo fragmentation at formulation pH values of 5.0 and below. Hence, the found beneficial formulation is especially suitable for antibody constructs according to the present invention, such as scFc as third domain.

Example 7

An EGFRvIII targeting non-HLE (half-life extended) BiTE® antibody construct (BiTE® A) exempt of a half-life extending moiety was formulated in 20 mM citric acid monohydrate, 100 mM L-Arginine monohydrochlorid at pH 4.8. Fractions of this solution were spiked with 0, 100, and 200 mM sodium chloride using a 4M stock solution. The concentration of each fraction was adjusted to 0.8 mg BiTE A per mL. The final solutions were aliquoted to 2.5 mL in ready-to-use 10R type I glass vials which were closed with butyl rubber stoppers and aluminum flip off seals. These solutions were stored at 30° C. for 12 weeks and stability was assessed using different analytical methods.

SE-UPLC was performed on an ACQUITY UPLC H-Class Bio System (Waters, Milford, MA, USA), consisting of Bio Sample Manager-FTN, Bio Quaternary Solvent Manager, and photo diode array (PDA) detector in order to determine protein concentration. Chromatographic separation was carried out using an Acquity UPLC Protein BEH 200 SEC column (packed 1.7 µm, 4.6×150 mm) (Waters, Milford, MA, USA). Column temperature was maintained at 25° C. 100 µL of each sample solution were filled to Glass Screw Neck Vials with PTFE/silicone septum (Waters, Milford, MA, USA). Autosampler was temperature controlled at 8° C.

Samples were measured in duplicates with 3 µg/sample loaded onto the column, corresponding to an injection volume of 3.8 µL at a protein concentration of about 0.8 mg/mL per run. Sample elution was performed under isocratic conditions at a flow rate of 0.4 mL/min using a mobile phase of 100 mM sodium phosphate buffer, pH 6.8 with additional 250 mM sodium chloride buffer. The running buffer was automatically premixed by the system with 500 mM monobasic sodium phosphate loaded onto channel A, 500 mM dibasic sodium phosphate onto channel B, 1 M sodium chloride onto channel C and HPLC grade water onto channel D. In between the sample runs, 10 µL of 40% acetonitrile were injected. At the beginning, the middle and the end of each analysis a protein standard was measured to ensure system suitability. Run time was set to 6 minutes. Eluted samples were detected by means UV absorption was determined at a wavelength of 280 nm. Acquisition and integration of chromatograms were performed using Empower Software (Waters, Milford, MA, USA). Chromatograms were analyzed regarding the area under the curve (AUC) for concentration determination of the sample. Values are given as mean values of independent sample triplicates with corresponding standard deviation.

Protein concentration was calculated using the following equation:

$$c = \frac{\frac{AUC}{1000} * \frac{Flow\ rate}{60}}{\varepsilon * Flow\ path * Injection\ volume}$$

Equation: Calculation of Sample Concentration in Mg/mL from Area Under the Curve (AUC) Values in mAU*s. Parameters are Outlined in Table 11.

TABLE 11

| Parameters of SE-UPLC method for calculation of sample concentration in mg/mL. | |
| --- | --- |
| Parameter | Value |
| Injection volume [mL] | 0.0038 |
| Flow rate [mL/min] | 0.4 |
| Flow path [cm] | 0.5 |
| Extinction coefficient $\varepsilon$ [AU mg$^{-1}$ cm$^{-1}$ mL] | 2.0000 |

Protein concentration of BiTE® A preparations as a function of formulation and storage time is given in Table 12. While protein concentration remained constant over time in absence of sodium chloride, significant protein losses were observed in salt containing preparations. Protein losses were most pronounced in formulations with 200 mM sodium chloride.

TABLE 12

| Protein concentration as a function of formulation and storage time | | |
| --- | --- | --- |
| NaCl [mM] | Storage Time | Concentration[mg/mL] |
| 0 | T0 | 0.80 ± 0.01 |
| | T4 w | 0.78 ± 0.01 |
| | T8 w | 0.78 ± 0.01 |
| | T12 w | 0.76 ± 0.02 |

TABLE 12-continued

| Protein concentration as a function of formulation and storage time | | |
| --- | --- | --- |
| NaCl [mM] | Storage Time | Concentration[mg/mL] |
| 100 | T0 | 0.84 ± 0.01 |
| | T4 w | 0.80 ± 0.00 |
| | T8 w | 0.75 ± 0.01 |
| | T12 w | 0.70 ± 0.00 |
| 200 | T0 | 0.79 ± 0.01 |
| | T4 w | 0.66 ± 0.01 |
| | T8 w | 0.55 ± 0.00 |
| | T12 w | 0.47 ± 0.00 |

Light obscuration was applied to measure the amount of subvisible particles larger than 10 and 25 µm within BiTE® A preparations. Light obscuration measurements were performed on a HIAC 9703+ Liquid Particle Counting System (Beckmann Coulter, Brea, CA, USA) equipped with HRLD 150 sensor. Data acquisition and analysis were conducted using the corresponding PharmSpec 3 Software. Prior to sample analysis, system suitability was verified by measurement of EZY™-Cal Particle size standard 5 µm (Thermo Fisher Scientific, Waltham, MA, USA) and EZY™-Cal Particle size standard 15 µm (Thermo Fisher Scientific, Waltham, MA, USA). For each sample, four measurements of 0.2 mL sample volume were performed at a flow rate of 10 mL/min. As the first run was discarded, particle concentration was given as the mean from the last three measurements. Prior to sample measurement and in between blank tests were performed. Particle concentration of particle free water was determined to guarantee a maximal amount of 10 particles/mL≥2 µm and 1 particle/mL≥10 µm. Subvisible particle concentrations for particles larger than 10 and 25 µm are given as mean values of independent triplicates.

Table 13 outlines subvisible particle counts for BiTE® A containing preparations as a function of formulation and storage time. Subvisible particle counts were lowest in absence of sodium chloride and only marginally change over time. The addition of sodium chloride resulted in comparable initial particle counts. However, the amount of subvisible particles significantly increased over time in presence of salt. This demonstrates that colloidal stability of preparations containing is improved in absence of sodium chloride.

TABLE 13

| Subvisible particle counts per mL as function of formulation and storage time | | | |
| --- | --- | --- | --- |
| NaCl [mM] | Storage Time | ≥10 µm | ≥25 µm |
| 0 | T0 | 1288 | 59 |
| | T4 w | 1466 | 62 |
| | T8 w | 1894 | 108 |
| | T12 w | 2383 | 61 |
| 100 | T0 | 1540 | 83 |
| | T4 w | 4708 | 258 |
| | T8 w | 6206 | 550 |
| | T12 w | 6139 | 811 |
| 200 | T0 | 1541 | 53 |
| | T4 w | 7594 | 933 |
| | T8 w | 7778 | 1133 |
| | T12 w | 5233 | 972 |

BiTE® A containing preparations were thermally analyzed by nano differential scanning calorimetry (nanoDSF). Unfolding and aggregation behavior of differently formulated BiTE® A preparations were monitored using the Prometheus NT.48 instrument (NanoTemper Technologies, Munich, Germany) and the corresponding PRThermControl Software (NanoTemper Technologies, Munich, Germany). For analysis of protein unfolding temperature Tm and detection of aggregation temperature Tagg, 10 μL per sample were filled to Prometheus NT.48 standard capillaries (NanoTemper Technologies, Munich, Germany) by capillary forces and placed in the instrument. Samples were measured in triplicates. Temperature ramp was defined from 20° C. to 95° C., with a heating rate of 1° C./min.

Data analysis was performed using the Prometheus PRThermControl software (NanoTemper Technologies, Munich, Germany). In case of thermal unfolding experiments fluorescence ratio (F350 nm/F330 nm) respectively its first derivative was plotted against the temperature. For aggregation detection, scattered light intensity respectively its first derivative was plotted against the temperature.

Protein unfolding temperature ($T_m$) and aggregation temperature ($T_{agg}$) are given in Table 14 as average values with standard deviation calculated from triplicates. It was demonstrated that unfolding ($T_m$) and protein aggregation ($T_{agg}$) occurred at higher temperatures in absence of sodium chloride. This indicates enhanced conformational and colloidal stability of formulation exempt of salt.

TABLE 14

Characterisation of thermal unfolding and aggregation behavior with nano-DSF as a function of formulation

| NaCl [mM] | $T_m 1$ [° C.] | $T_{agg}$ [° C.] |
|---|---|---|
| 0 | 52.9 ± 0.0 | 52.5 ± 0.1 |
| 100 | 51.7 ± 0.0 | 50.6 ± 0.0 |
| 200 | 51.0 ± 0.0 | 49.3 ± 0.1 |

Example 8

Two BCMA targeting BiTE® antibody constructs with (BiTE® F) and without (BiTE® E) an additional cys-clamp in the domain directed against BCMA and containing a single-chain Fc domain at the C-terminal end were formulated in 10 mM L-glutamic acid, 9% (w/v) sucrose at pH 4.8. Fractions of this solution were spiked with 0, 100, and 200 mM sodium chloride using a 4M stock solution. The concentration of each fraction was adjusted to 0.8 mg BiTE® per mL. The final solutions were aliquoted to 2.5 mL in ready-to-use 1 OR type I glass vials which were closed with butyl rubber stoppers and aluminum flip off seals. These solutions were stored at 30° C. for 12 weeks and stability was assessed using different analytical methods.

SE-UPLC was performed as described in Example 7. Detection was carried out by measuring fluorescence emission intensity at 325 nm using an excitation wavelength of 280 nm. The relative area under the curve (AUC) attributable to low molecular weight species (LMWS). As shown in Table 15 the formation of LMWS over time is less pronounced in absence of sodium chloride and indicates an improved stability of salt free preparations.

TABLE 15

Percentaged amount of LMWS in BiTE ®E and BiTE ® F preparation as function of formulation and storage time

| | Storage | LMWS [%] | |
|---|---|---|---|
| NaCl [mM] | Time | BiTE ® E | BiTE ® F |
| 0 | T0 | 0.0 ± 0.0 | 0.0 ± 0.0 |
| | T4 w | 2.5 ± 0.0 | 2.6 ± 0.0 |
| | T8 w | 3.1 ± 0.0 | 3.3 ± 0.1 |
| | T12 w | 4.0 ± 0.1 | 4.3 ± 0.1 |
| 100 | T0 | 0.0 ± 0.0 | 0.0 ± 0.0 |
| | T4 w | 2.8 ± 0.0 | 3.0 ± 0.0 |
| | T8 w | 3.8 ± 0.1 | 4.0 ± 0.0 |
| | T12 w | 5.0 ± 0.0 | 5.4 ± 0.0 |
| 200 | T0 | 0.0 ± 0.0 | 0.0 ± 0.0 |
| | T4 w | 2.9 ± 0.0 | 3.1 ± 0.1 |
| | T8 w | 4.1 ± 0.1 | 4.3 ± 0.0 |
| | T12 w | 5.4 ± 0.1 | 5.7 ± 0.0 |

Light obscuration was performed as described in Example 7. The abundance of subvisible particles in BiTE® E and BiTE® F preparations as a function of formulation and storage is given in Table 16. Subvisible particles were less pronounced in absence of sodium chloride independent of storage time if compared to preparations containing salt. This indicates an improved colloidal stability of BiTE® E and BiTE® F in formulations exempt of salt.

TABLE 16

Subvisible particle counts per mL as function of formulation and storage time

| | Storage | ≥10 μm | | ≥25 μm | |
|---|---|---|---|---|---|
| NaCl [mM] | Time | BiTE ® E | BiTE ® F | BiTE ® E | BiTE ® F |
| 0 | T0 | 19 | 26 | 1 | 3 |
| | T4 w | 72 | 74 | 5 | 7 |
| | T8 w | 60 | 26 | 6 | 2 |
| | T12 w | 101 | 63 | 9 | 8 |
| 100 | T0 | 18 | 25 | 1 | 3 |
| | T4 w | 662 | 587 | 38 | 50 |
| | T8 w | 150 | 288 | 9 | 20 |
| | T12 w | 937 | 699 | 61 | 42 |
| 200 | T0 | 205 | 33 | 19 | 3 |
| | T4 w | 735 | 1971 | 2137 | 186 |
| | T8 w | 266 | 493 | 859 | 48 |
| | T12 w | 1381 | 572 | 3701 | 45 |

BiTE® E and BiTE® F preparations were thermally analyzed by nano differential scanning calorimetry (nanoDSF) using the method described under Example 7. Protein unfolding temperature ($T_m$) and aggregation temperature ($T_{agg}$) are given in Table 17 as average values with standard deviation calculated from triplicates. It was demonstrated that unfolding ($T_m$) and occurred at higher temperatures in presence of 200 mM NaCl if compared to preparations containing 0 or 100 mM sodium chloride. Protein aggregation was not detected for salt free preparation in the tested temperature range. In contrast, protein aggregation was observed for preparations containing sodium chloride. Aggregation temperature decreased with higher salt concentrations. Above findings indicate enhanced conformational and colloidal stability of formulation exempt of salt.

TABLE 17

| Characterisation of thermal unfolding and aggregation behaviour with nano-DSF as a function of formulation | | | | |
|---|---|---|---|---|
| | $T_m$ [° C.] | | $T_{agg}$ [° C.] | |
| NaCl [mM] | BiTE ® E | BiTE ® F | BiTE ® E | BiTE ® F |
| 0 | 58.2 ± 0.1 | 58.2 ± 0.1 | n.d. | n.d. |
| 100 | 58.2 ± 0.0 | 58.2 ± 0.0 | 77.1 ± 0.4 | 76.9 ± 0.1 |
| 200 | 57.6 ± 0.0 | 57.6 ± 0.0 | 68.4 ± 0.6 | 71.2 ± 0.1 | n.d. = not detected

Lengthy table referenced here

US12617853-20260505-T00001

Please refer to the end of the specification for access instructions.

Lengthy table referenced here

US12617853-20260505-T00002

Please refer to the end of the specification for access instructions.

Lengthy table referenced here

US12617853-20260505-T00003

Please refer to the end of the specification for access instructions.

LENGTHY TABLES

The patent contains a lengthy table section. A copy of the table is available in electronic form from the USPTO web site (https://seqdata.uspto.gov/docdetail?docId=US12617853B2). An electronic copy of the table will also be available from the USPTO upon request and payment of the fee set forth in 37 CFR 1.19(b)(3).

SEQUENCE LISTING

The patent contains a lengthy sequence listing. A copy of the sequence listing is available in electronic form from the USPTO web site (https://seqdata.uspto.gov/docdetail?docId=US12617853B2). An electronic copy of the sequence listing will also be available from the USPTO upon request and payment of the fee set forth in 37 CFR 1.19(b)(3).

The invention claimed is:

1. A liquid pharmaceutical composition comprising (a) an antibody construct comprising at least:

a first domain comprising an Fv fragment having the VL and VH domains of a single arm of an antibody which binds to a target cell surface antigen, wherein the target cell surface antigen is a tumor antigen selected from MSLN, DLL3, FLT3, BCMA, PSMA, CD33, and CD19, and wherein the first domain has an isoelectric point (pI) in the range of 4 to 9.5;

a second domain comprising an Fv fragment having the VL and VH domains of a single arm of an antibody which binds to an extracellular epitope of CD3 of the human and/or *Macaca* CD3 epsilon (CD3ε) chain, wherein the VL domain comprises an amino acid sequence comprising at least 90% sequence identity to the amino acid sequence of SEQ ID NO: 13 and the VH domain comprises an amino acid sequence comprising at least 85% sequence identity to the amino acid sequence of SEQ ID NO: 14, and wherein the second domain has a pI in the range of 8.5 to 9.5; and a third domain comprising two polypeptide monomers, each monomer comprising a hinge, a CH2 domain and a CH3 domain, wherein each of said polypeptide monomers of the third domain comprises an amino acid sequence that is at least 90% identical to a sequence selected from the group consisting of: SEQ ID NOs: 17-24, wherein said two polypeptide monomers are fused to each other via a peptide linker, and wherein the third domain has a pI in the range of 5.5 to 7.5;

(b) at least one buffer agent selected from the group consisting of: acetate, glutamate, citrate, succinate, tartrate, maleate, and phosphate, or any combination thereof, wherein the at least one buffer agent is present at a concentration in the range of 5 to 100 mM;

(c) at least one saccharide selected from the group consisting of: sucrose, trehalose, mannitol, and sorbitol, wherein the at least one saccharide is present at a concentration in the range of 1 to 15% m/V; and (d) at least one surfactant selected from the group consisting of: polysorbate 20, polysorbate 40, polysorbate 60, polysorbate 80, and poloxamer 188, wherein the at least one surfactant is present at a concentration in the range of 0.004 to 0.5% m/V;

wherein the composition does not comprise sodium chloride, and wherein the pH of the pharmaceutical composition is in the range of 4.0 to 5.0.

2. The composition of claim 1, wherein the antibody construct is a single chain antibody construct.

3. The composition of claim 1, wherein each of said polypeptide monomers of the third domain comprises the amino acid sequence of any one of SEQ ID NOs: 17-24.

4. The composition of claim 1, wherein the antibody construct comprises in an amino to carboxyl order:

(a) the first domain;

(b) a peptide linker having an amino acid sequence selected from the group consisting of SEQ ID NOs: 1-3;

(c) the second domain;

(d) a peptide linker having an amino acid sequence selected from the group consisting of SEQ ID NOs: 1, 2, 3, 9, 10, 11 and 12;

(e) the first polypeptide monomer of the third domain;

(f) a peptide linker having an amino acid sequence selected from the group consisting of SEQ ID NOs: 5, 6, 7 and 8; and (g) the second polypeptide monomer of the third domain.

5. The composition of claim 1, wherein the pH of the composition is 4.2.

6. The composition of claim 1, having an osmolarity in the range of 150 to 500 mOsm.

7. The composition of claim 1, further comprising an excipient selected from the group consisting of:

one or more polyols; and one or more amino acids.

8. The composition of claim 7, wherein the excipient is present in the concentration range of 0.1 to 15% m/V.

9. The composition of claim 1, wherein the buffer agent is 10 mM acetate or glutamate, wherein the saccharide is 9% m/V sucrose, wherein the surfactant is 0.01% m/V polysorbate 80, and wherein the pH of the liquid pharmaceutical composition is 4.2.

10. The composition of claim 1, wherein the antibody construct is present at a concentration in the range of 0.1 to 8 mg/ml.

11. A solid pharmaceutical composition, obtained by lyophilizing the composition of claim 1.

12. A method for therapeutically treating or ameliorating a proliferative disease, an immunological disease or a viral disease comprising administering an effective amount of the composition of claim 1 to a subject in need thereof.

13. The method of claim 12, wherein the composition is administrated parenterally.

14. The method of claim 12, wherein the composition is administered (i) 1, 2, 3, 4, 5, 6 or 7 times per week, (ii) 1, 2, 3, 4, 5 or 6 times every two weeks, (iii) 1 or 2 times per month, (iv) 1 or 2 times every two months, or (v) 1 time per week.

15. The pharmaceutical composition of claim 1, wherein the second domain comprises a single chain antibody fragment (scFv) comprising an amino acid sequence comprising at least 85% sequence identity to the amino acid sequence of SEQ ID NO: 15.

16. A liquid pharmaceutical composition comprising (a) an antibody construct comprising at least:

a first domain comprising an amino acid sequence selected from SEQ ID NOs: 202 and 1409, and wherein the first domain has an isoelectric point (pI) in the range of 4 to 9.5;

a second domain comprising an Fv fragment having the VL and VH domains of a single arm of an antibody which binds to an extracellular epitope of CD3 of the human and/or *Macaca* CD3 epsilon (CD3c) chain, wherein the VL domain comprises an amino acid sequence comprising at least 90% sequence identity to the amino acid sequence of SEQ ID NO: 13 and the VH domain comprises an amino acid sequence comprising at least 85% sequence identity to the amino acid sequence of SEQ ID NO: 14, and wherein the second domain has a pI in the range of 8.5 to 9.5; and a third domain comprising two polypeptide monomers, each monomer comprising a hinge, a CH2 domain and a CH3 domain, wherein each of said polypeptide monomers of the third domain comprises an amino acid sequence that is at least 90% identical to a sequence selected from the group consisting of: SEQ ID NOs: 17-24, wherein said two polypeptide monomers are fused to each other via a peptide linker, and wherein the third domain has a pI in the range of 5.5 to 7.5;

(b) at least one buffer agent selected from the group consisting of: acetate, glutamate, citrate, succinate, tartrate, maleate, and phosphate, or any combination thereof, wherein the at least one buffer agent is present at a concentration in the range of 5 to 100 mM;

(c) at least one saccharide selected from the group consisting of: sucrose, trehalose, mannitol, and sorbitol, wherein the at least one saccharide is present at a concentration in the range of 1 to 15% m/V; and (d) at least one surfactant selected from the group consisting of: polysorbate 20, polysorbate 40, polysorbate 60, polysorbate 80, and poloxamer 188, wherein the at least one surfactant is present at a concentration in the range of 0.004 to 0.5% m/V;

wherein the composition does not comprise sodium chloride, and wherein the pH of the pharmaceutical composition is in the range of 4.0 to 5.0.

17. A liquid pharmaceutical composition comprising (a) an antibody construct comprising an amino acid sequence selected from SEQ ID NOs: 205 and 1411;

(b) at least one buffer agent selected from the group consisting of: acetate, glutamate, citrate, succinate, tartrate, maleate, and phosphate, or any combination thereof, wherein the at least one buffer agent is present at a concentration in the range of 5 to 100 mM;

(c) at least one saccharide selected from the group consisting of: sucrose, trehalose, mannitol, and sorbitol, wherein the at least one saccharide is present at a concentration in the range of 1 to 15% m/V; and (d) at least one surfactant selected from the group consisting of: polysorbate 20, polysorbate 40, polysorbate 60, polysorbate 80, and poloxamer 188, wherein the at least one surfactant is present at a concentration in the range of 0.004 to 0.5% m/V;

wherein the composition does not comprise sodium chloride, and wherein the pH of the pharmaceutical composition is in the range of 4.0 to 5.0.

* * * * *